United States Patent [19]

Janssen et al.

[11] 3,998,834
[45] Dec. 21, 1976

[54] N-(4-PIPERIDINYL)-N-PHENYLAMIDES AND -CARBAMATES

[75] Inventors: Paul Adriaan Jan Janssen, Vosselaar; Georges Henri Paul Van Daele, Turnhout, both of Belgium

[73] Assignee: Janssen Pharmaceutica N.V., Beerse, Belgium

[22] Filed: Jan. 13, 1976

[21] Appl. No.: 648,685

Related U.S. Application Data

[63] Continuation-in-part of Ser. No. 558,511, March 14, 1975, abandoned.

[52] U.S. Cl. .................. 260/293.68; 260/293.69; 260/293.77; 424/267
[51] Int. Cl.² ............ C07D 401/12; C07D 417/12; C07D 405/12; C07D 211/58
[58] Field of Search ............... 260/293.68, 293.69, 260/293.77

[56] References Cited

UNITED STATES PATENTS 3,164,600  1/1965  Janssen et al. ............... 260/293.77

FOREIGN PATENTS OR APPLICATIONS 1,517,670  2/1968  France .................. 260/293.77
1,517,671  2/1968  France .................. 260/293.77

OTHER PUBLICATIONS

Riley et al., "J. Pharm. Sci." vol. 62, pp. 983–986 (1973).
Casy et al. "J. Pharm. Pharmac." vol. 21, pp. 434–440 (1969).

*Primary Examiner*—Henry R. Jiles
*Assistant Examiner*—Robert T. Bond
*Attorney, Agent, or Firm*—Salvatore R. Conte

[57] ABSTRACT

Novel N-(4-piperidinyl)-N-phenylamides and -carbamates having very potent analgesic activity, methods of preparing same and useful intermediates therefor.

17 Claims, No Drawings

N-(4-PIPERIDINYL)-N-PHENYLAMIDES AND -CARBAMATES

CROSS-REFERENCE TO RELATED APPLICATIONS

This is a continuation-in-part of our copending application, Ser. No. 558,511, filed Mar. 14, 1975, now abandoned.

BACKGROUND OF THE INVENTION

This invention pertains to the field of N-(4-piperidinyl)-N-phenylamides and -carbamates. In the prior art there may be found some N-(4-piperidinyl)-N-phenylamides and -carbamates having analgesic activity. Among other points of difference, the compounds of this invention differ from the prior art compounds by the nature of the $R^1$-substituent, present in the 4-position of the piperidine ring.

The closest prior art may be represented by the following references:
U.S. Pat. No. 3,164,600;
Riley et al., J. Pharm. Sci., 62, 983 (1973); and
Belg. Pat. No. 818.989.

DESCRIPTION OF THE PREFERRED EMBODIMENTS

This invention relates to novel chemical compounds, more particularly to N-(4-piperidinyl)-N-phenylamides and -carbamates represented by the formula

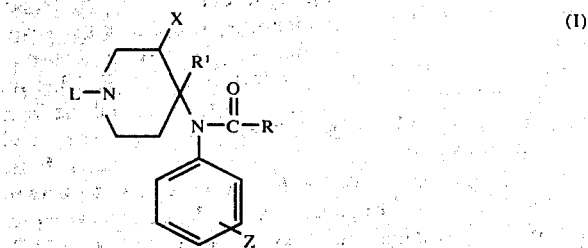

and the pharmaceutically acceptable acid addition salts thereof; wherein

Z is a member selected from the group consisting of hydrogen halo, lower alkyl, lower alkyloxy and trifluoromethyl;

L is a member selected from the group consisting of alkyl having from 3 to about 10 carbon atoms, cycloalkylmethyl, 2-arylethyl, 2-aryl-1-methylethyl, 2-aryl-2-hydroxyethyl, 2-aryl-2-hydroxy-1-methylethyl, 1-(arylcarbonyl)ethyl, 3-arylpropyl, 2-(arylamino)ethyl, 2-aryl-2-(lower alkylcarbonyloxy)ethyl, 2-aryl-2-(lower alkylcarbonyloxy)-1-methylethyl, 2-[aryl(lower alkylcarbonyl)amino]ethyl, 4-phenylcyclohexyl, 2,3-dihydro-1H-inden-2-yl, and lower alkenyl; said "aryl" being a member selected from the group consisting of phenyl, halophenyl, lower alkylphenyl, lower alkyloxyphenyl, (trifluoromethyl)phenyl, nitrophenyl, aminophenyl, naphthalenyl, pyridinyl, 2-furanyl, 2-thienyl, and 1-methyl-1H-pyrrol-2-yl;

X is a member selected from the group consisting of hydrogen and methyl;

R is a member selected from the group consisting of lower alkyl, lower alkyloxy and cycloalkyl; and $R^1$ is a member selected from the group consisting of
a. a carboxylate radical represented by the formula

wherein $R^2$ is a member selected from the group consisting of lower alkyl, lower alkenyl and phenylmethyl;

b. an alkanoyl radical represented by the formula

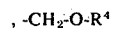

wherein $R^3$ is lower alkyl; and c. an oxymethyl radical represented by the formula

, $-CH_2-O-R^4$ wherein $R^4$ is selected from the group consisting of hydrogen, lower alkyl, phenylmethyl and lower alkylcarbonyl; provided that i. when said $R^2$ is phenylmethyl, or when said $R^4$ is a member selected from the group consisting of phenylmethyl and lower alkylcarbonyl, then said L is selected from the group consisting of alkyl, cycloalkylmethyl, 2-arylethyl, 2-aryl-2-(lower alkylcarbonyloxy)ethyl, 2-aryl-2-(lower alkylcarbonyloxy)-1-methylethyl, 2-aryl-1-methylethyl, 1-(arylcarbonylethyl), 3-arylpropyl, 4-phenylcyclohexyl, 2,3-dihydro-1H-inden-2-yl, and lower alkenyl; and ii. when said $R^4$ is hydrogen then said L is other than 2-[aryl(lower alkylcarbonyl)amino]ethyl.

As used in the foregoing definitions, the term "alkyl" is meant to include straight and branch chained hydrocarbon radicals, having from 3 to about 10 carbon atoms such as, for example, propyl, 1-methylethyl, butyl, 1-methylpropyl, 2-methylpropyl, pentyl, hexyl oxtyl, decyl and the like; the term "lower alkyl" refers to a straight or branch chained hydrocarbon chain having from 1 to 6 carbon atoms such as, for example, methyl, ethyl, propyl, 1-methylethyl, butyl, 1-methylpropyl, pentyl, hexyl and the like; the term "lower alkenyl" refers to an alkenyl radical having from 3 to 6 carbon atoms such as, for example, 2-propen-1-yl, 2-buten-1-yl, 1-methyl-2-propen-1-yl, 2-penten-1-yl and the like; the expression "cycloalkyl" refers to a cyclic alkyl having from 3 to 6 carbon atoms, e.g. cyclopropyl, cyclobutyl, cyclopentyl and cyclohexyl; and the term "halo" is generic to halogens of atomic weight less than 127, i.e., fluoro, chloro, bromo and iodo.

Those compounds of formula (I) which may be represented by the structure

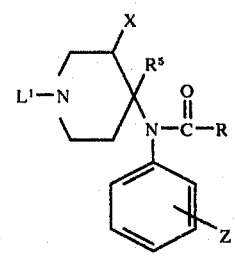

(I-a)

wherein:

R, X and Z are as previously defined;

L¹ is selected from the group consisting of alkyl, cycloalkylmethyl, 2-arylethyl, 2-aryl-1-methylethyl, 2-aryl-2-hydroxyethyl, 2-aryl-2-hydroxy-1-methylethyl, 1-(arylcarbonyl)ethyl, 3-arylpropyl, 2-(arylamino)ethyl, 2-aryl-2-(lower alkylcarbonyloxy)ethyl, 2-aryl-2-(lower alkylcarbonyloxy)-1-methylethyl, 4-phenylcyclohexyl, 2,3-dihydro-1H-inden-2-yl and lower alkenyl, wherein said aryl is other than aminophenyl; and R⁵ is a member selected from the group consisting of:
a. a radical having the formula

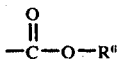

wherein R⁶ is lower alkyl or lower alkenyl;
b. a radical of the formula

wherein R³ is as previously defined; and
c. a radical of the formula

wherein R⁷ is hydrogen or lower alkyl;
may generally be prepared by introducing the L¹-substituent on to the ring nitrogen of an intermediate of the formula

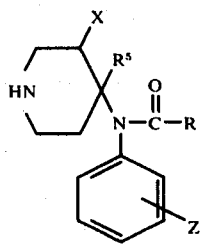

(II)

wherein R, X, Z and R⁵ are as previously defined, by the application of conventional methodologies known in the art. Depending on the nature of the L¹-substituent, the following methods may be utilized therefor.

When L¹ is alkyl, cycloalkylmethyl, 2-arylethyl, 2-aryl-1-methylethyl, 1-(arylcarbonyl)ethyl, 3-arylpropyl, 2-(arylamino)-ethyl, 2-aryl-2-(lower alkylcarbonyloxy)ethyl, 2-aryl-2-(lower alkylcarbonyloxy)-1-methylethyl, 4-phenylcyclohexyl, 2,3-dihydro-1H-inden-2-yl, or lower alkenyl, in which case said L¹ is represented by "L$_a^1$", the introduction of said L$_a^1$ into the intermediate (II) may conveniently be carried out by the reaction of (II) with an appropriate reactive ester L$_a^1$Y, (III), wherein Y is a reactive ester residue, such as, for example, halo, e.g., chloro, bromo or iodo, or another reactive ester residue such as, for example, methanesulfonyl (mesyl), 4-methylbenzenesulfonyl (tosyl) and the like. When L$_a^1$ stands for 2,3-dihydro-1H-inden-2-yl the use of the methanesulfonate or 4-methylbenzenesulfonate is preferred.

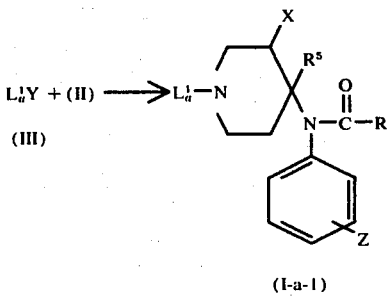

(I-a-1)

The condensation reaction of (II) with (III) is conveniently conducted in an inert organic solvent such as, for example, an aromatic hydrocarbon, e.g., benzene, methylbenzene, dimethylbenzene, and the like; a lower alkanol, e.g., methanol, ethanol, 1-butanol and the like; a ketone, e.g., 4-methyl-2-pentanone and the like; an ether, e.g., 1,4-dioxane, 1,1'-oxybisethane and the like; N,N-dimethylformamide (DMF); nitrobenzene; and the like. The addition of an appropriate base such as, for example, an alkali metal carbonate or hydrogen carbonate, or an organic base such as, for example, N,N-diethylethanamine or N-(1-methylethyl)-2-propanamine may be utilized to pick up the acid that is liberated during the course of the reaction. In some circumstances the addition of an iodide salt, preferably an alkali metal iodide, is appropriate. Somewhat elevated temperatures may be employed to enhance the rate of the reaction.

When L¹ is a 2-aryl-2-hydroxyethyl or 2-aryl-2-hydroxy-1-methylethyl radical, the introduction of said substituent into the intermediate (II), to obtain the compounds (I-a-2), may conveniently be carried out by reacting (II) with an appropriate oxirane of formula (IV) wherein R⁸ is hydrogen or methyl:

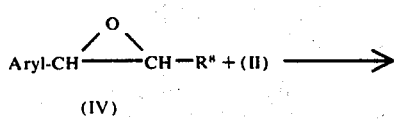

(IV)

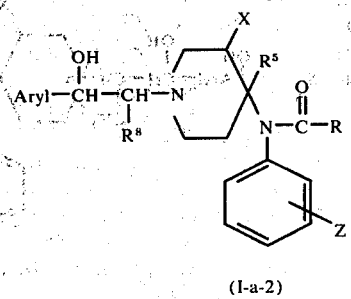

(I-a-2)

The reaction of (II) with (IV) may be carried out in an appropriate organic solvent or in the absence of any solvent.

Suitable solvents which may be employed include, for example, aromatic hydrocarbons such as benzene, methylbenzene, dimethylbenzene and the like; halogenated hydrocarbons such as, for example, trichloromethane, dichloromethane and the like; lower alkanols such as methanol, ethanol, 2-propanol and the like alcohols; and mixtures of such solvents.

When $L^1$ stands for a 4-phenylcyclohexyl- or a 2,3-dihydro-1H-inden-2-yl radical the introduction of said $L^1$ into (II), to obtain respectively the compounds (I-a-3) and (I-a-4), may conveniently be achieved by reacting respectively 4-phenylcyclohexanone or 2,3-dihydro-1H-inden-2-one with (II) with simultaneous catalytic hydrogenation using an appropriate catalyst such as, for example, palladium-on-charcoal and an appropriate solvent such as, for example, a lower alkanol, e.g., methanol or ethanol.

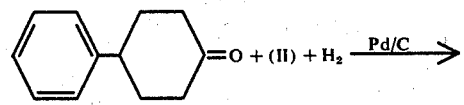

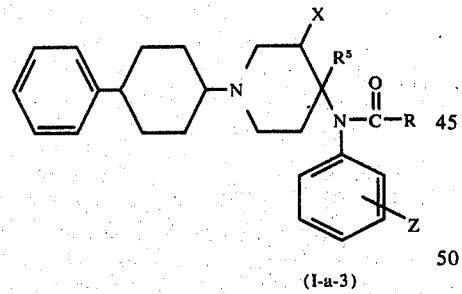

(I-a-3)

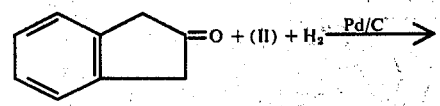

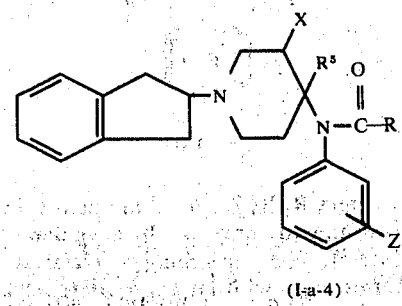

(I-a-4)

The compounds of formula (I) which may be represented by the structure:

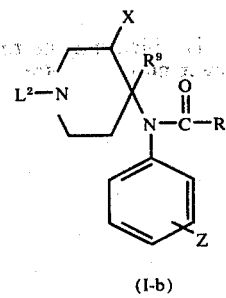

(I-b)

wherein:
R, Z and X are as previously defined;
$L^2$ is a member selected from the group consisting of alkyl, cycloalkylmethyl, 2-arylethyl, 2-aryl-1-methylethyl, 1-(arylcarbonyl)ethyl, 3-arylpropyl, 2-aryl-2-(lower alkylcarbonyloxy)ethyl, 2-aryl-2-(lower alkylcarbonyloxy)-1-methylethyl, 4-phenylcyclohexyl, 2,3-dihydro-1H-inden-2-yl, and lower alkenyl, wherein said aryl is other than aminophenyl; and
$R^9$ is a member selected from the group consisting of:
a. a radical of the formula

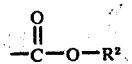

wherein $R^2$ is as previously defined;
b. a radical of the formula

wherein $R^3$ is as previously defined; and
c. a radical of the formula

wherein $R^{10}$ is a lower alkyl- or phenylmethyl radical, may be prepared by acylation of an appropriate 4-piperidinamine of formula (V). Said acylation reaction is conveniently carried out according to known N-acylation procedures, for example, by reacting (V) with an appropriate acyl halide, R—CO—halo, representing respectively a lower alkylcarbonyl halide, a cycloalkylcarbonyl halide or a lower alkyl carbonhalidate, following methodologies generally known in the art. When R stands for lower alkyl or cycloalkyl the acylation may also be carried out with an anhydride derived from the acid RCOOH or with mixed anhydrides of the acid RCOOH with, for example, methanesulfonic acid, 4-methylbenzenesulfonic acid or trifluoromethanesulfonic acid, or with triflamide acylating reagents according to procedures described in the literature, for example, in Tetrahedron Letters, 46, 4607 (1973).

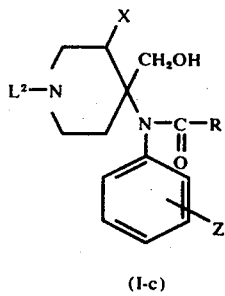

(V)

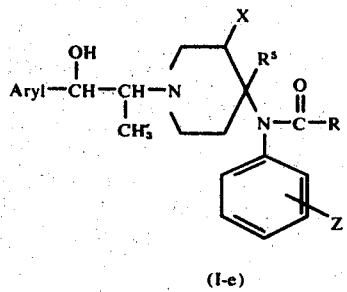

(I-e)

The compounds of formula (I) which may be represented by the structure:

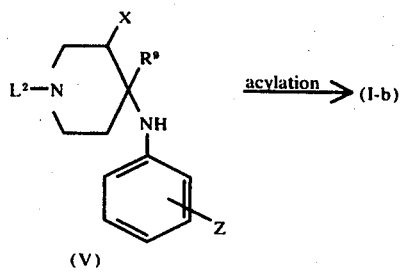

(I-c)

wherein R, X, Z and R⁵ are as previously defined, may alternatively be prepared by the reduction of an appropriate ketone of formula (I-f), wherein X, R, Z and $R^5$ are as previously defined, with an appropriate reducing agent such as, for example, sodium borohydride in an appropriate organic solvent, such as, for example, a lower alkanol.

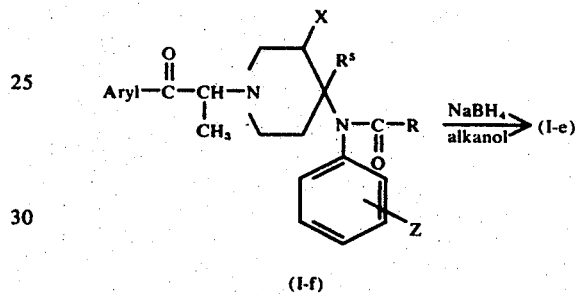

(I-f)

wherein:
R, X, Z and $L^2$ are as previously defined, may alternatively be prepared by catalytic removal of the phenylmethyl group of a phenylmethyl ether of formula (I-d)

Compounds of formula (I) which may be represented by the structure:

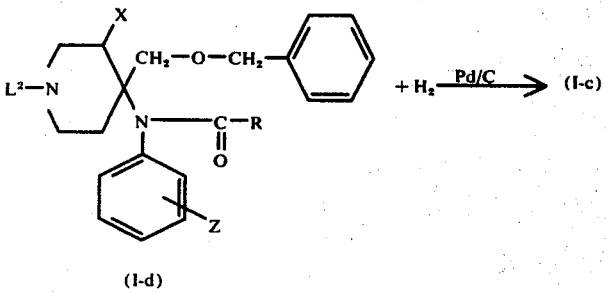

(I-d)

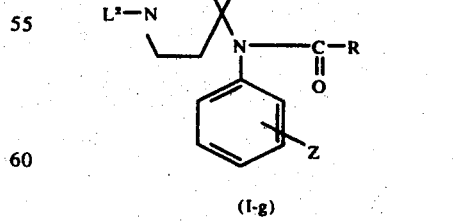

(I-g)

The elimination of the phenylmethyl group may conveniently be carried out by catalytic hydrogenation using an appropriate catalyst such as, for example, palladium-on-charcoal, in an appropriate solvent such as, for example, a lower alkanol.

The compounds of formula (I) which may be represented by the structure:

wherein R, X, Z and $L^2$ are as previously defined; are conveniently prepared by acylation of a compound of formula (I-c) according to classical acylation procedures, e.g., with an appropriate acyl halide or anhydride.

(I-c) —acylation→ (I-g)

The compounds of formula (I-g-1), wherein X, Z and L² are as previously defined and the R¹¹-groups are two identical lower alkyl radicals, may alternatively be prepared by simultaneous O- and N-acylation of an appropriate intermediate of formula (VI), according to generally known procedures, e.g. with an appropriate acyl halide or anhydride.

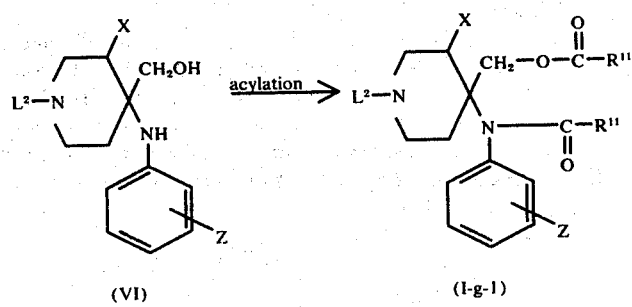

(VI)     (I-g-1)

The compounds of formula (I) wherein the L-substituent has an aminophenyl group within its structure are conveniently prepared starting from the corresponding nitro-substituted analogs by the reduction of said nitro group to an amino group following common nitro-to-amine reduction procedures. Advantageously one may use therefor an appropriate reducing agent such as, for example, iron metal and ammonium chloride, zinc metal and acetic acid, or the reduction may be carried out by catalytic hydrogenation, using a suitable catalyst such as, for example, Raney-nickel, palladium-on-charcoal and the like.

The compounds of formula (I) wherein L stands for 2-aryl-2-(lower alkylcarbonyloxy)ethyl, 2-aryl-2-(lower alkylcarbonyloxy)-1-methylethyl or 2-[aryl(-lower alkylcarbonyl)amino]ethyl may conveniently be prepared by respectively O- or N-acylation of the corresponding compounds of formula (I) wherein L is 2-aryl-2-hydroxyethyl, 2-aryl-2-hydroxy-1-methylethyl or 2-(arylamino)ethyl. Said acylation reaction may be carried out in the usual manner, using, for example, an appropriate halide or anhydride derived from the appropriate lower alkylcarboxylic acid.

The intermediates of formula (II) may generally be prepared by acylating an appropriate piperidine derivative of formula (VII), wherein R⁵, X and Z are as previously defined and P is an appropriate protecting group such as, for example, phenylmethyl or phenylmethoxycarbonyl, with an appropriate acylating agent to introduce the RCO acyl moiety, and thereafter removing the protecting group of the thus obtained (VIII) according to art-known procedures, e.g. by catalytic hydrogenation using palladium-on-charcoal catalyst.

The acylation step may be carried out following the procedures described herebefore for the preparation of the compounds (I-b) starting from (V).

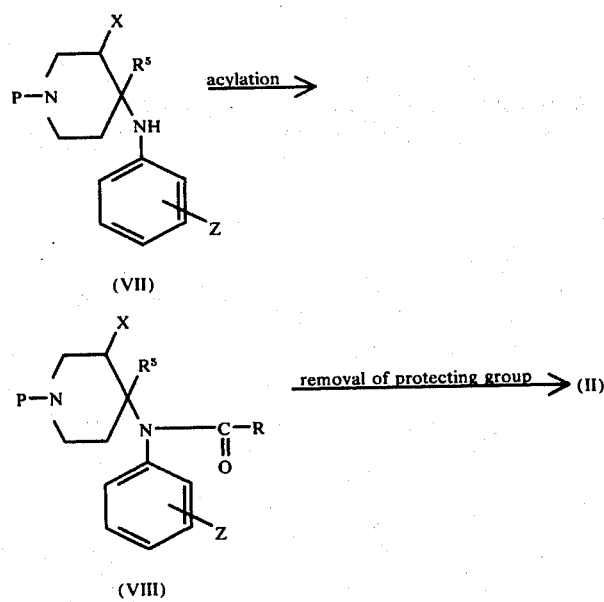

When the acyl group to be introduced is lower alkyloxycarbonyl it is appropriate to start from an intermediate of formula (VII) wherein P stands for phenylmethoxycarbonyl, (VII-a). If desired said (VII-a) may be derived from the corresponding phenylmethyl substituted analog, (VII-b) by replacement of the phenylmethyl group with a phenylmethoxycarbonyl group. This may be done by first eliminating the phenylmethyl group in the usual manner and thereafter introducing the phenylmethoxycarbonyl group by the reaction of the thus obtained (IX) with an appropriate (phenylmethyl)carbonohalidate (X) at elevated temperatures in an appropriate reaction-inert organic solvent such as, for example, trichloromethane, or by directly reacting (VII-b) with (X).

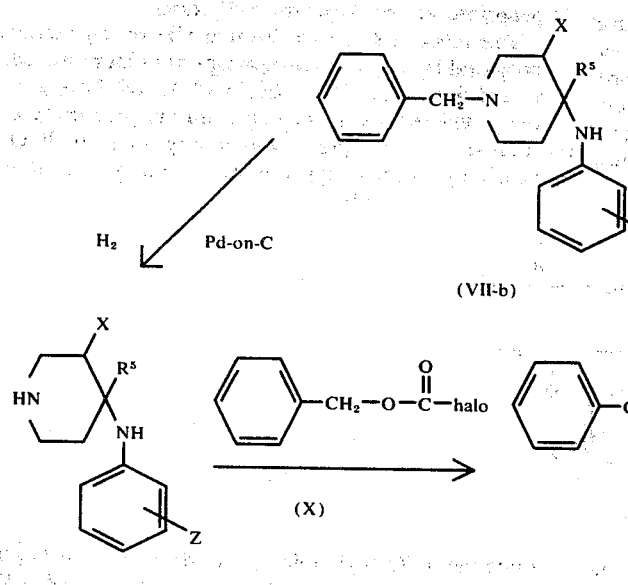
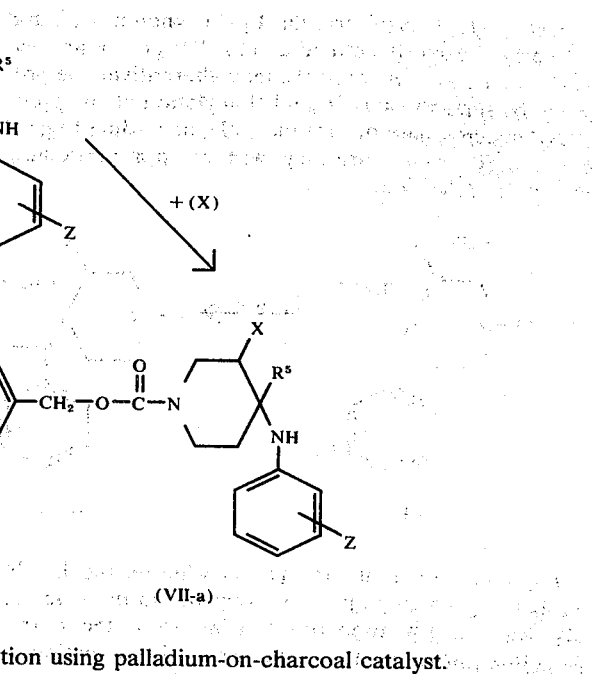

(VII-b)

(IX)

(X)

(VII-a)

In order to prepare intermediates of formula (II) wherein R⁵ is hydroxymethyl, (II-a), it is appropriate to start from a phenylmethyl ether of formula (XI), in which the RCO group is introduced in the usual manner to obtain (XII), whereafter the protecting group P and the phenylmethyl group on the oxymethyl radical are simultaneously eliminated by catalytic hydrogenation using palladium-on-charcoal catalyst.

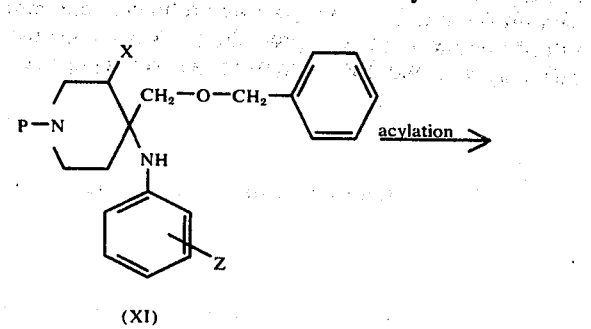

(XI)

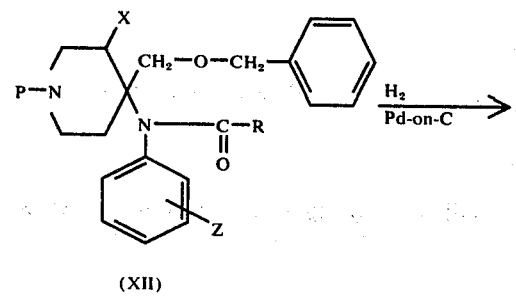

(XII)

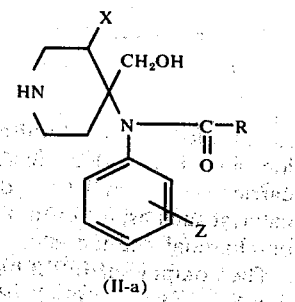

(II-a)

The 4-piperidinecrboxylate intermediates of formula (VII-b), which may be represented by the structure

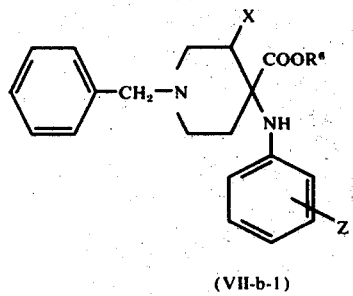

(VII-b-1)

wherein X, Z and $R^6$ are as previously defined, may be prepared by the following sequence of reactions.

A 1-phenylmethyl-4-(phenylamino)piperidine-4-carboxamide of formula (XIII) is hydrolized to obtain the corresponding carboxylic acid (XIV), by the application of known amide-to-acid hydrolysis procedures, for example, by treating (XIII) with a strong acid, e.g. hydrochloric or sulfuric acid, or by alkaline hydrolysis using an appropriate base, e.g. sodium or potassium hydroxide. The thus obtained carboxylic acid (XIV) is in turn converted into a metal salt thereof, preferably the sodium salt (XV), by reaction with alkali, e.g. with sodium hydroxide.

The carboxylic acid (XIV) need not necessarily be isolated or purified, but may be utilized as a crude mixture in the preparation of (XV), or the salt may be obtained directly when alkaline hydrolysis is carried out.

The salt (XV) is then converted into an ester of formula (VII-b-1) by the reaction with an appropriate lower alkyl- or lower alkenyl halide of formula (XVI) in an appropriate solvent such as, for example, hexamethylphosphoric triamide. Alternatively the esters (VII-b-1) may be prepared by converting the acid (XIV) into an acyl halide (XVII) in the usual manner, by the treatment with an appropriate halogenating agent, e.g. with sulfinyl chloride, and reacting said acyl halide with an appropriate lower alkanol or alkenol of formula (XVIII) or simply by reacting the acid with an appropriate alcohol in the presence of an acid.

The foregoing reactions are more clearly illustrated in the following schematic representation.

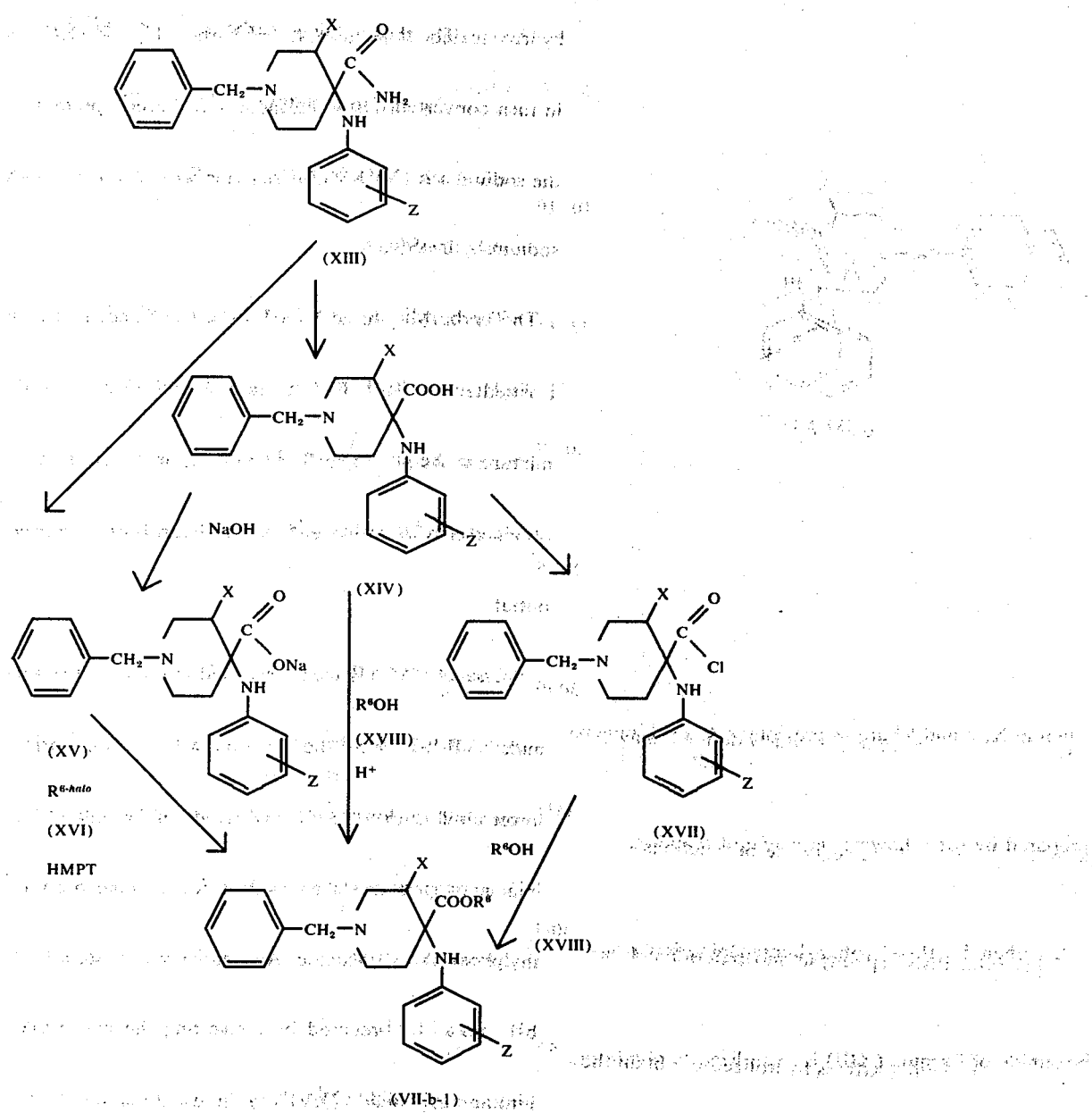

Intermediates of formula (XIII) wherein X is hydrogen and methods of preparing the same, are described in U.S. Pat. Nos. 3,238,216 and 3,161,644. The intermediates of formula (XIII), including those wherein X is a methyl group, may generally be prepared as follows:

A 4-oxo-1-piperidinecarboxylate of formula (XIX), wherein $R^{12}$ stands for lower alkyl or phenylmethyl, is reacted with an appropriate benzenamine (XX) and an alkali metal cyanide, for example, potassium cyanide, in an aqueous organic carboxylic acid, such as acetic acid, or in an aqueous lower alkanol, in the presence of an equivalent of an inorganic acid such as hydrochloric acid, whereby introduction of the nitrile function and of the amine function is effected at the 4-position of the piperidine ring, whereby an intermediate of formula (XXI) is obtained.

The nitrile (XXI) is then converted into the amide (XXII) by acid hydrolysis. Advantageously one may use a strong, aqueous, inorganic acid for this purpose, such as hydrochloric acid, phosphoric acid and, preferably, sulfuric acid.

The carboxylate group of (XXII) is subsequently removed by alkaline hydrolysis or, when $R^{12}$ stands for a phenylmethyl radical by catalytic hydrogenation using, for example, palladium-on-charcoal catalyst.

The thus-obtained intermediate (XXIII) may then be converted into (XIII) by the reaction of (XXIII) with an appropriate reactive ester (XXIV) derived from benzenemethanol, preferably a (halomethyl)benzene. The condensation reaction is conveniently carried out in an appropriate organic solvent such as, for example, N,N-dimethylacetamide (DMA) or N,N-dimethylformamide (DMF) in the presence of an appropriate base, e.g., N,N-diethylethanamine to bind the acid that is liberated during the course of the reaction.

The foregoing reactions may be illustrated by the following reaction scheme:

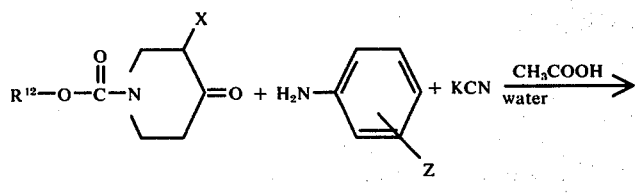

(XIX)    (XX)

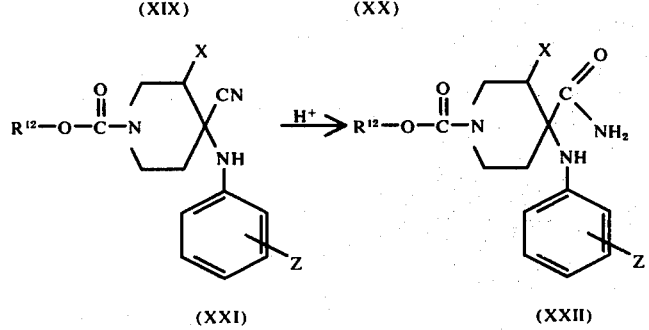

(XXI)    (XXII)

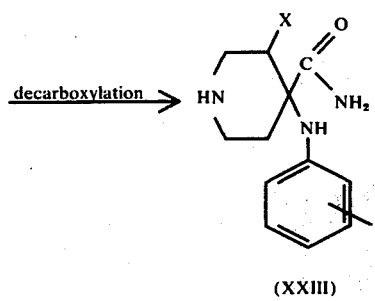

(XXIII)

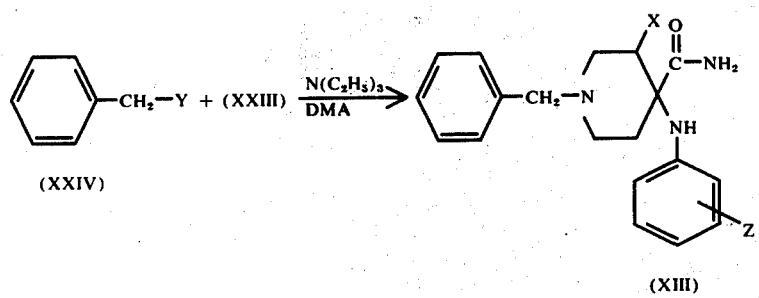

(XXIV)    (XIII)

The 4-(lower alkylcarbonyl)piperidine intermediates of formula (VII-2)

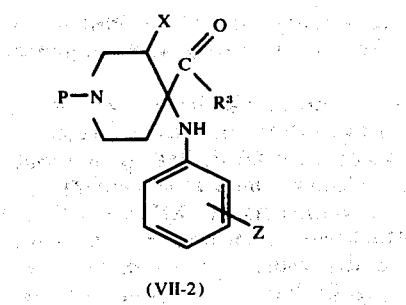

(VII-2)

wherein X, Z and R³ are as previously defined, may be prepared as follows:

A 4-(phenylamino)-4-piperidinecarboxylic acid of formula (XXV) or an alkali metal salt thereof is converted into a 1-piperidinecarboxylate of formula (XXVII) wherein R¹² is lower alkyl or phenylmethyl, by the reaction of (XXV) with an appropriate carbonohalidate of formula (XXVI), preferably under Schotten-Bauman conditions, using aqueous alkali and an appropriate water-immiscible organic solvent such as, for example, tetrahydrofuran, dichloromethane, benzene, methylbenzene, dimethylbenzene and the like solvents.

The thus obtained intermediate of formula (XXVII) is then cyclized with an appropriate cyclizing agent such as carbonic dichloride to obtain an intermediate of formula (XXVIII). The intermediate (XXVIII) is subsequently reacted with a Grignard complex, (XXIX), previously prepared starting from magnesium metal and an appropriate halo-lower alkane, R³-halo, in an appropriate solvent as generally employed in Grignard reactions to obtain respectively a compound of formula (VII-a-2) when R¹² stands for phenylmethyl, or an intermediate of formula (XXX) when R¹² stands for lower alkyl. The phenylmethyl-substituted intermediates of formula (VII-b-2) may be derived from the latter by first hydrolytically eliminating the lower alkylcarbonyl group of (XXX) to obtain (XXXI) and thereafter introducing the phenylmethyl group in the usual manner by the reaction of (XXXI) with an appropriate reactive ester derived from benzenemethanol.
The foregoing reactions may be represented schematically as follows:
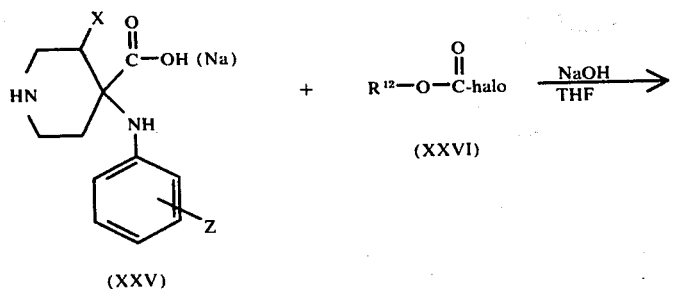
(XXV)    (XXVI)
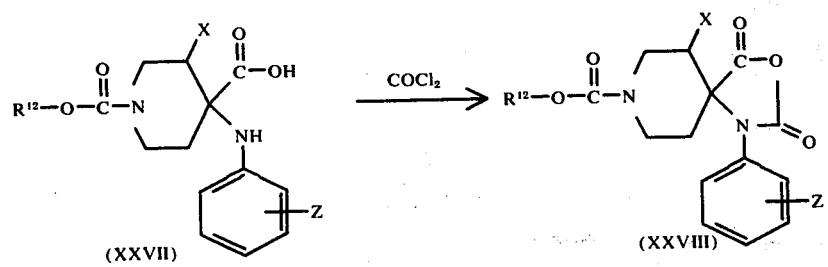
(XXVII)    (XXVIII)
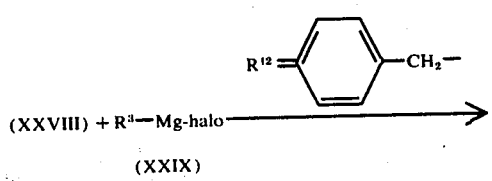
(XXVIII) + R³—Mg-halo ⟶
(XXIX)
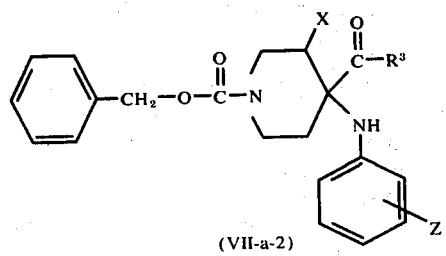
(VII-a-2)
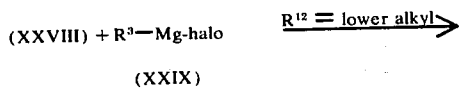
(XXVIII) + R³—Mg-halo $\xrightarrow{R^{12} = \text{lower alkyl}}$
(XXIX)

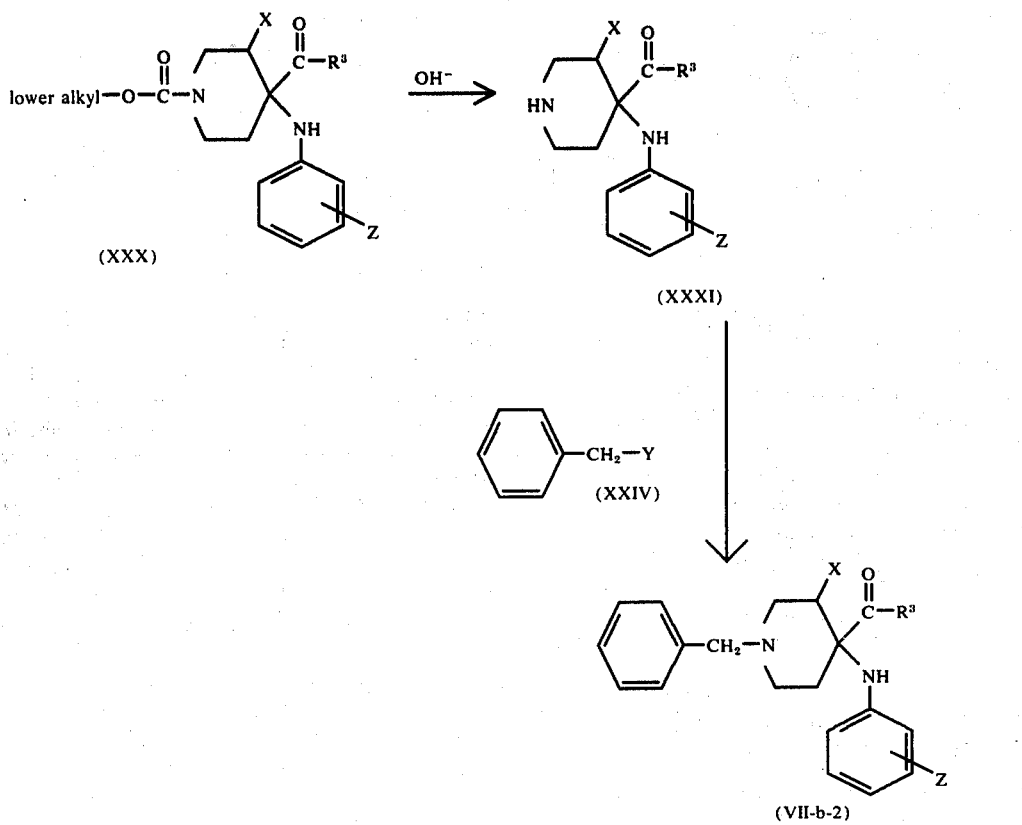

The intermediates of formula (XXV) used as starting material herein may conveniently be prepared by catalytically removing the phenylmethyl group of an intermediate of formula (XIV) according to known procedures as described hereinbefore.

The intermediates of the formula

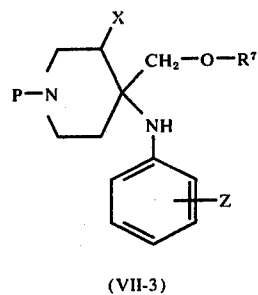

(VII-3)

wherein P, X, Z, and $R^7$ are as previously defined may be prepared as follows:

A 4-piperidinecarboxylic acid ester of formula (VII-b-1) wherein $R^6$ is preferably a lower alkyl radical is reduced with an appropriate reducing agent such as, for example, sodium dihydrobis(2-methoxyethoxy)aluminate (Red-Al) in an appropriate organic solvent such as, for example, benzene, or with lithium borohydride or sodium borohydride in the presence of a lithium salt, to obtain a 4-piperidinemethanol of formula (XXXII).

The intermediates of formula (VII-3) wherein $R^7$ is a lower alkyl radical, (VII-b-3) are conveniently obtained by O-alkylation of (XXXII) with an appropriate alkylating agent.

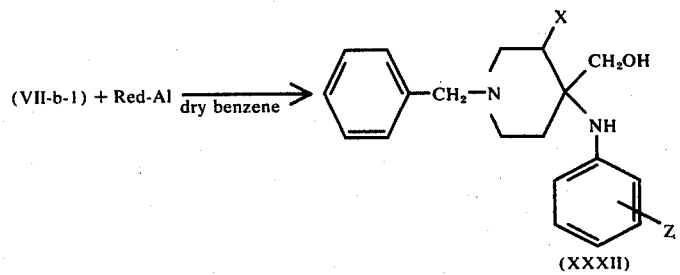

(XXXII) —O-alkylation→ 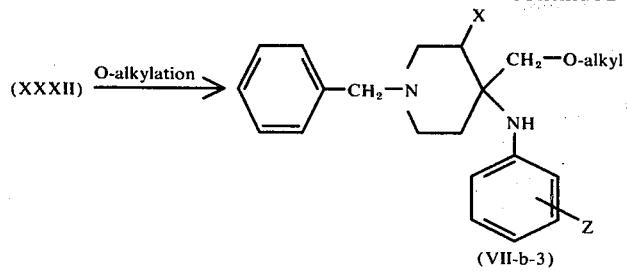

(VII-b-3)

The O-alkylation step may be carried out by the reaction of (XXXII) with an appropriate halo-lower alkane in an appropriate organic solvent such as, for example, hexamethylphosphoric triamide (HMPT), in the presence of a strong metal base such as sodium hydride. Alternatively, the O-alkylation may be carried out by reacting (XXXII) with an alkylating agent such as a halo-lower alkane or a di(lower alkyl) sulfate in a mixture of strong aqueous alkali and an organic solvent such as, for example, benzene, methylbenzene, dimethylbenzene, tetrahydrofuran and the like in the presence of an appropriate quaternary ammonium salt such as N,N,N-triethylbenzenemethanaminium chloride (BTEAC).

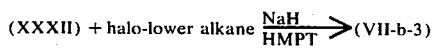

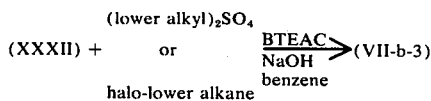

The intermediates of formula (XI), used as starting materials in the preparation of (II-a) are prepared as follows:

An intermediate of formula (XXXII) is converted into a phenylmethyl ether of formula (XI-b), e.g. by the reaction of (XXXII) with an appropriate (halomethyl)-benzene according to known procedures as described hereinbefore. The intermediates of formula (XI) wherein P stands for a phenylmethoxycarbonyl group, (XI-a), may be derived from (XI-b) by treatment of the latter with a (phenylmethyl) carbonohalidate of formula (X) following the same procedure as described hereinbefore for the preparation of the intermediates (VII-a) starting from (VII-b).

The intermediates of formula (V) may conveniently be prepared according to the procedures described hereafter.

The intermediates of formula (V) which may be represented by the formula

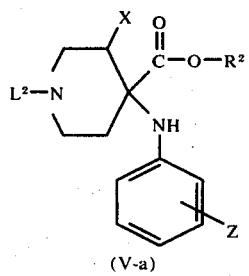

(V-a)

wherein X, Z, $L^2$ and $R^2$ are as previously defined, may be prepared as follows:

When $R^2$ stands for lower alkyl or lower alkenyl, in which case said intermediates are represented by the formula (V-a-1), they may conveniently be obtained by eliminating the phenylmethyl protecting group from an intermediate of formula (VII-b-1) followed by the introduction of the desired $L^2$ into the thus obtained intermediate (XXXIII) following the procedures described hereinbefore for the preparation of the compounds (I-a) starting from (II).

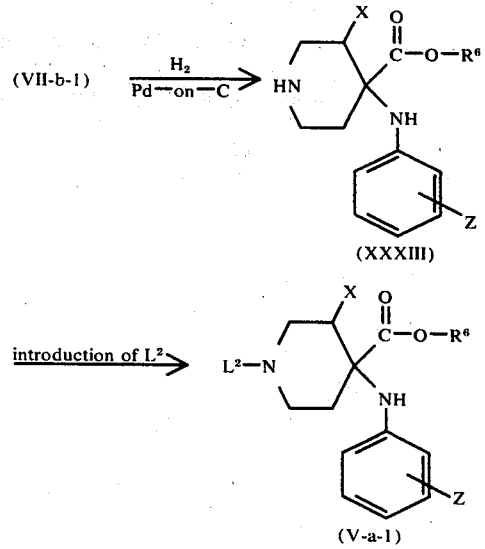

The intermediates of formula (V-a) wherein X, Z and $R^2$ are as previously defined and $L^2$ is a member selected from the group consisting of alkyl, cycloalkylmethyl, 2-arylethyl, 2-aryl-1-methylethyl, 4-phenylcyclohexyl, 2,3-dihydro-1-H-inden-2-yl, and lower alkenyl, wherein said aryl is different from aminophenyl, represented by $L^2_a$, are prepared as follows:

Into a 4-(phenylamino)-4-piperidinecarboxyamide of formula (XXIII) the $L^2_a$-substituent is introduced according to known procedures as previously described. The thus obtained intermediate of formula (XXXIV) is then converted into an alkali metal salt (XXXV) of the corresponding carboxylic acid by alkaline hydrolysis using, for example, potassium hydroxide or sodium hydroxide, preferably in 1,2-ethanediol. From the intermediate (XXXV) or the corresponding free carboxylic acid the desired esters of formula (V-a-2) are obtained by common esterification procedures, e.g., as described hereinbefore for the preparation of the intermediates (VII-a-1).

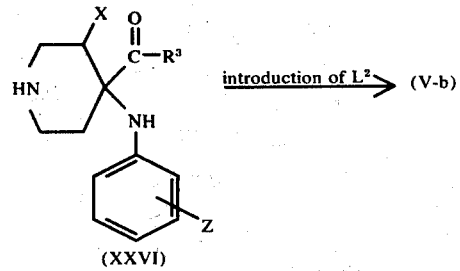

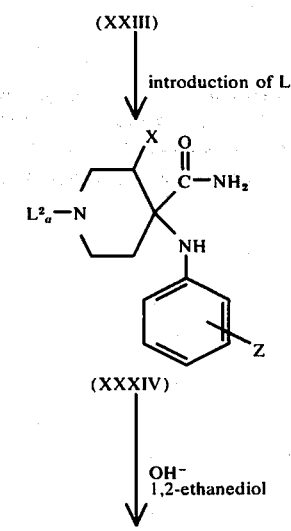

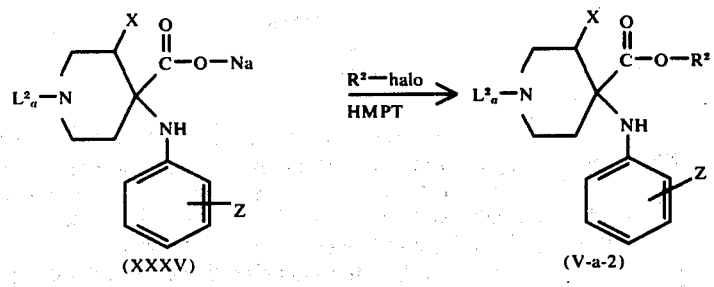

The intermediates of formula (V) in which $R^9$ is a lower alkylcarbonyl radical and which may be represented by the structure:

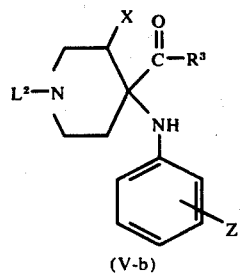

wherein $L^2$, X, Z and $R^3$ have the previously indicated meaning, may be prepared by introducing $L^2$ in the usual manner into an intermediate of formula (XXVI), prepared as described hereinbefore.

The intermediates of formula (V-b-1) wherein aryl, X and Z are as previously defined.

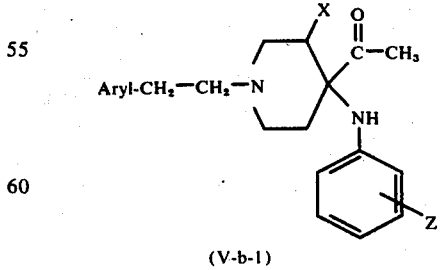

may alternatively be prepared by the reaction of a 4-piperidinecarboxylic acid of formula (XXXVI) with methyl lithium in an appropriate solvent such as, for example, 1,1'-oxybisethane.

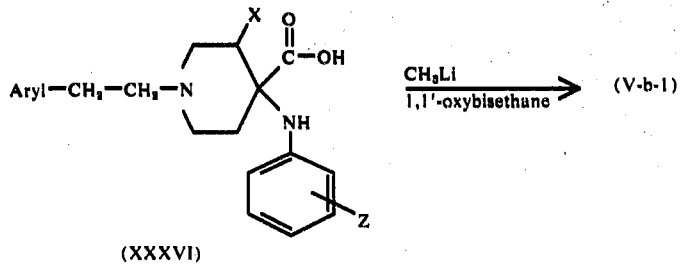

The carboxylic acids (XXXVI) may be prepared by converting an appropriate metal 4-piperidinecarboxylate of formula (XXXV), wherein $L^2_a$ stands for a 2-arylethyl radical, into the free carboxylic acid by the application of common procedures as known in the art.

The free acids may alternatively be obtained by hydrolyzing an appropriate ester thereof or by catalytic elimination of the phenylmethyl group of an appropriate phenylmethyl ester.

The intermediates of formula (V-c)

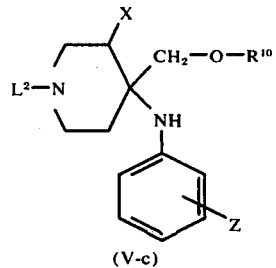

wherein $L^2$, X, Z and $R^{10}$ are as previously defined may be prepared as follows:

Those intermediates of formula (V-c) in which $R^{10}$ stands for a lower alkyl radical, (V-c-1), are conveniently prepared by eliminating the phenylmethyl group of an intermediate of formula (VII-b-3) in the usual manner and thereafter introducing the desired $L^2$ according to the procedures outlined hereinbefore.

The intermediates of formula (V-c), including those wherein $R^{10}$ is phenylmethyl, may in turn be obtained by O-alkylation of an intermediate of formula (VI) with an appropriate halo-lower alkane of (halomethyl)benzene.

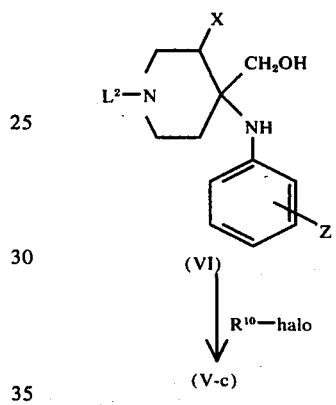

The intermediates of formula (VI) may be prepared by the reduction of an appropriate lower alkyl ester of formula (V-a-1) with an appropriate reducing agent, such as sodium dihydrobis(2-methoxyethoxy)aluminate, lithium borohydride and the like, or alternatively by eliminating the phenylmethyl group of a compound of formula (XXXII) and thereafter introducing $L^2$ in the usual manner.

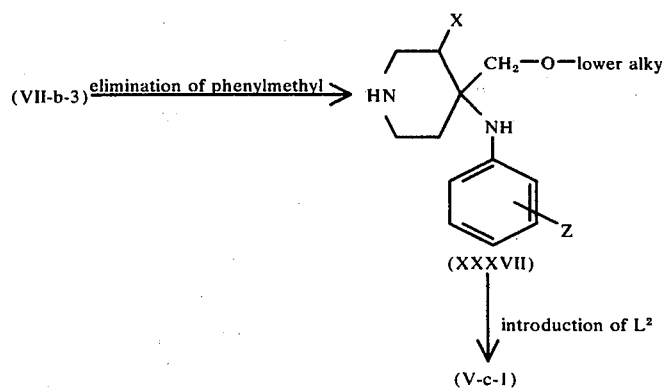

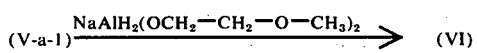

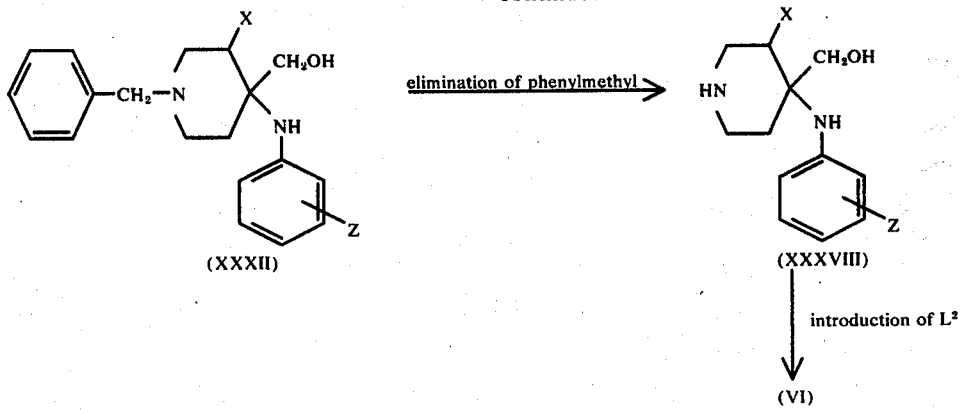

The intermediates of formula (XXXIV) may alternatively be prepared by the following procedure.

Into a piperidineketal of formula (XXXIX), the $L^2_a$-group is introduced in the usual manner as described before for the preparation of the intermediates (XXII) starting from (XIX).

The foregoing reactions are illustrated in the following schematic representation:

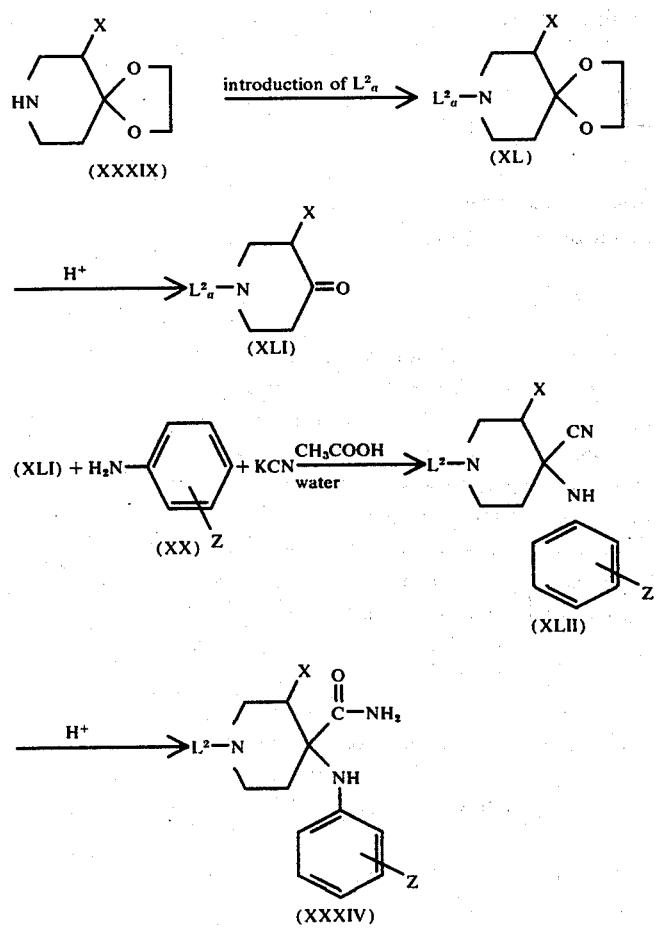

hereinbefore and subsequently the resulting ketal of formula (XL) is converted into a 4-piperidinone of formula (XLI) by treatment with an appropriate strong acid, e.g. hydrochloric acid. The intermediate (XLI) is thereafter reacted with an alkali metal cyanide and a benzenamine (XX) to obtain an intermediate nitrile of formula (XLII) which in turn is hydrolyzed to the desired amide (XXXIV). The latter reactions may be carried out following the procedures described hereinbefore.

It is believed that the compounds of formula (II) are novel and as useful intermediates in the preparation of compounds of formula (I) they constitute an additional feature of this invention.

The compounds of formulas (V) and (VI) are also believed to be novel and as useful intermediates herein they form also part of this invention. Generically, the intermediates (V) and (VI) may be represented by the formula:

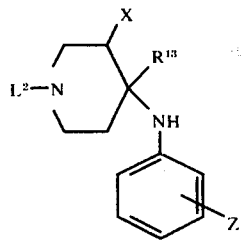

wherein X, Z and L² are as previously defined; and R¹³ is a member selected from the group consisting of:

a. a radical of the formula

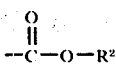

wherein R² is as previously defined;

b. a radical of the formula

wherein R³ is as previously defined; and c. a radical of the formula

wherein R¹⁴ is selected from the group consisting of hydrogen, lower alkyl and phenylmethyl.

The reactive ester compounds of formula (III) as well as the epoxides of formula (IV) are generally known and they may be prepared according to known procedures described in the literature.

The subject compounds may be converted to the therapeutically active non-toxic acid addition salt form by treatment with an appropriate acid, such as, for example, an inorganic acid, such as hydrohalic acid, e.g., hydrochloric, hydrobromic, and the like, and sulfuric acid, nitric acid, phosphoric acid and the like; or an organic acid, such as, for example, acetic, propanoic, hydroxyacetic, α-hydroxypropanoic, 2-oxopropanoic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, benzoic, 3-phenyl-2-propenoic, α-hydroxybenzeneacetic, methanesulfonic, ethanesulfonic, benzenesulfonic, 4-methylbenzenesulfonic, cyclohexanesulfamic, α-hydroxybenzoic, 4-amino-2-hydroxybenzoic and the like acids. Conversely, the salt form can be converted by treatment with alkali into the free base form.

Several of the compounds of formula (I) have one or more asymmetric carbon atoms in their structure and consequently they may exist in the form of different stereochemically optically isomeric forms or mixtures of such forms, e.g. racemates.

When X in formula (I) represents a methyl group there are 2 asymmetric carbon atoms in the piperidine ring while additional asymmetric carbon atoms may also be present in the L-substituent, for example, when L is 2-aryl-1-methylethyl, 2-aryl-2-hydroxyethyl or 2-aryl-2-hydroxy-1-methylethyl.

Stereochemically optically isomeric forms and mixtures of such forms may be obtained separately by the application of methods of resolution known to those skilled in the art such as, for example, selective crystallization, salt formation with optically active acids and counter-current-distribution.

For example, when X is a methyl group, the relative position of said methyl group and of the substituents in the 4-position of the piperidine ring with respect to the plane of the piperidine ring may be cis or trans, according to the rules of nomenclature described in "Naming and Indexing of Chemical Substances for C.A. during the Ninth Collective Period (1972–1976) p. 861."

Compounds of formula (I) having the cis- or trans-configuration, essentially free of the other, may be obtained, for example, by starting their preparation from pure cis- or trans-isomers of the appropriate precursors. When, for example, an intermediate of formula (XXII) in which X stands for methyl is subjected to a selective crystallization, cis- and trans-isomers are easily obtained separately and the thus-obtained pure forms are conveniently used in the further synthesis of compounds of formula (I) having the corresponding configuration. Alternatively, substantially pure forms of the cis- and trans-isomer of compounds of formula (I) may be obtained, substantially free of the other isomer, by separating a mixture of such forms by counter-current-distribution.

Cis- and trans-forms may in turn be further resolved into their optical enantiomers, each essentially free of its optical counterpart, by the application of art-known methodologies, e.g. by salt formation with optically active acids, such as, for example, with optical isomers of 2-{[(4-methylphenyl)sulfonyl]amino}pentanedioic acid. All of the aforementioned isomeric forms of compounds of formula (I) are intended to be within the scope of this invention.

The compounds of formula (I) and the pharmaceutically acceptable acid addition salts thereof are highly potent analgesics, as demonstrated, for example, in experimental animals.

In the following table are listed ED₅₀-values, obtained according to the rat tail withdrawal test described in Arzneimittel-Forschung, 13, 502 (1963) and 21, 862 (1971) upon intravenous (i.v.) administration. Said test is commonly used to demonstrate analgesic activity in the low ED₅₀-values obtained illustrate the potency of the compounds of this invention.

The compounds of formula (I) listed in the following table are not given for the purpose of limiting the invention thereto, but only to exemplify the potent analgesic properties of all the compounds within the scope of formula (I).

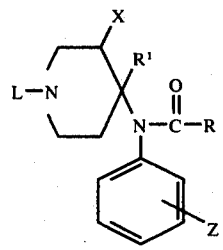

(I)

| L | R¹ | R | X | Z | Salt or base | $ED_{50}$-values in mg/kg i.v. |
|---|---|---|---|---|---|---|
| $nC_3H_7$ | $COOCH_3$ | $C_2H_5$ | H | H | $(COOH)_2$ | 0.03 |
| $iC_3H_7$ | $COOCH_3$ | $C_2H_5$ | H | H | $(COOH)_2$ | 0.06 |
| $nC_4H_9$ | $COOCH_3$ | $C_2H_5$ | H | H | $(COOH)_2$ | 0.03 |
| cyclopropyl-$CH_2$ | $COOCH_3$ | $C_2H_5$ | H | H | $(COOH)_2$ | 0.10 |
| $nC_5H_{11}$ | $COOCH_3$ | $C_2H_5$ | H | H | $(COOH)_2$ | 0.004 |
| $nC_6H_{13}$ | $COOCH_3$ | $C_2H_5$ | H | H | $(COOH)_2$ | 0.004 |
| $nC_7H_{15}$ | $COOCH_3$ | $C_2H_5$ | H | H | $(COOH)_2$ | 0.008 |
| $nC_8H_{17}$ | $COOCH_3$ | $C_2H_5$ | H | H | $(COOH)_2$ | 0.08 |
| phenyl-$CH_2-CH_2$ | $COOCH_3$ | $C_2H_5$ | H | H | $(COOH)_2$ | 0.0006 |
| 2-thienyl-$CH_2-CH_2$ | $COOCH_3$ | $C_2H_5$ | H | H | $(COOH)_2$ | 0.0006 |
| phenyl-$CH(OH)-CH_2$ | $COOCH_3$ | $C_2H_5$ | H | H | $(COOH)_2$ | 0.001 |
| 4-Cl-phenyl-$CH_2-CH_2$ | $COOCH_3$ | $C_2H_5$ | H | H | $(COOH)_2$ | 0.008 |
| 4-$CH_3O$-phenyl-$CH_2-CH_2$ | $COOCH_3$ | $C_2H_5$ | H | H | $(COOH)_2$ | 0.008 |
| 3-$CH_3$-phenyl-$CH_2-CH_2$ | $COOCH_3$ | $C_2H_5$ | H | H | $(COOH)_2$ | 0.003 |
| 4-$CH_3$-phenyl-$CH_2-CH_2$ | $COOCH_3$ | $C_2H_5$ | H | H | HCl | 0.008 |
| phenyl-$CH_2-CH(CH_3)$ | $COOCH_3$ | $C_2H_5$ | H | H | $(COOH)_2$ | 0.0007 |
| phenyl-$CH_2-CH_2-CH_2$ | $COOCH_3$ | $C_2H_5$ | H | H | $(COOH)_2 \cdot 1/2 H_2O$ | 0.015 |
| phenyl-$NH-CH_2-CH_2$ | $COOCH_3$ | $C_2H_5$ | H | H | $(COOH)_2$ | 0.005 |
| 2-$CH_3$-phenyl-$CH_2-CH_2$ | $COOCH_3$ | $C_2H_5$ | H | H | $(COOH)_2$ | 0.002 |
| 3-$CF_3$-phenyl-$CH_2-CH_2$ | $COOCH_3$ | $C_2H_5$ | H | H | $(COOH)_2$ | 0.008 |
| 2-$OCH_3$-phenyl-$CH_2-CH_2$ | $COOCH_3$ | $C_2H_5$ | H | H | $(COOH)_2$ | 0.001 |
| 3-$OCH_3$-phenyl-$CH_2-CH_2$ | $COOCH_3$ | $C_2H_5$ | H | H | $(COOH)_2$ | 0.002 |
| cyclohexyl-phenyl | $COOCH_3$ | $C_2H_5$ | H | H | $(COOH)_2$ | 0.03 |
| indanyl | $COOCH_3$ | $C_2H_5$ | H | H | $(COOH)_2$ $CH_3-CH(OH)-CH_3$ | 0.005 |
| phenyl-$CH_2-CH_2$ | $COOCH_3$ | $C_2H_5$ | $CH_3$ (cis-isomer) | H | $(COOH)_2$ | 0.0006 |

-continued

(I)

| L | R¹ | R | X | Z | Salt or base | ED$_{50}$-values in mg/kg i.v. |
|---|---|---|---|---|---|---|
| Ph-CH$_2$-CH$_2$ | COOCH$_3$ | C$_2$H$_5$ | CH$_3$ (trans-isomer) | H | (COOH)$_2$ | 0.02 |
| Ph-CH$_2$-CH$_2$ | COOCH$_3$ | ▷ | H | H | HCl | 0.0006 |
| Ph-CH$_2$-CH$_2$ | COOCH$_3$ | nC$_3$H$_7$ | H | H | HCl 1/2H$_2$O | 0.001 |
| Ph-CH$_2$-CH$_2$ | COOC$_2$H$_5$ | C$_2$H$_5$ | H | H | (COOH)$_2$ 1/2H$_2$O | 0.008 |
| Ph-CH$_2$-CH$_2$ | COOnC$_3$H$_7$ | C$_2$H$_5$ | H | H | (COOH)$_2$ | 0.08 |
| Ph-CH$_2$-CH$_2$ | COO-iC$_3$H$_7$ | C$_2$H$_5$ | H | H | (COOH)$_2$ | 0.02 |
| Ph-CH$_2$-CH$_2$ | COOCH$_2$-CH=CH$_2$ | C$_2$H$_5$ | H | H | (COOH)$_2$ | 0.015 |
| Ph-CH$_2$-CH$_2$ | COOCH$_2$-Ph | C$_2$H$_5$ | H | H | HCl | 0.05 |
| Ph-CH$_2$-CH(CH$_3$) | COOC$_2$H$_5$ | C$_2$H$_5$ | H | H | (COOH)$_2$ | 0.005 |
| Thienyl-CH$_2$-CH$_2$ | COOC$_2$H$_5$ | C$_2$H$_5$ | H | H | HCl | 0.005 |
| Ph-CH(OH)-CH$_2$ | COOC$_2$H$_5$ | C$_2$H$_5$ | H | H | HCl | 0.015 |
| Ph-CH$_2$-CH$_2$ | COOC$_2$H$_5$ | CH$_3$ | H | H | (COOH)$_2$ | 0.02 |
| Ph-CH$_2$-CH$_2$ | COOC$_2$H$_5$ | nC$_3$H$_7$ | H | H | HCl | 0.005 |
| Ph-CH$_2$-CH$_2$ | COOC$_2$H$_5$ | ▷ | H | H | HCl | 0.007 |
| Thienyl-CH$_2$-CH$_2$ | COO-nC$_3$H$_7$ | C$_2$H$_5$ | H | H | (COOH)$_2$ | 0.08 |
| Ph-CH(OH)-CH$_2$ | COO-nC$_3$H$_7$ | C$_2$H$_5$ | H | H | HCl | 0.08 |
| Ph-CH$_2$-CH$_2$ | COCH$_3$ | C$_2$H$_5$ | H | H | (COOH)$_2$ | 0.0005 |
| Ph-CH$_2$-CH$_2$ | COCH$_3$ | nC$_3$H$_7$ | H | H | (COOH)$_2$ | 0.001 |
| Ph-CH$_2$-CH$_2$ | COCH$_3$ | ▷ | H | H | (COOH)$_2$ | 0.0008 |
| Ph-CH$_2$-CH$_2$ | COC$_2$H$_5$ | C$_2$H$_5$ | H | H | (COOH)$_2$ | 0.00125 |
| Ph-CH$_2$-CH$_2$ | COC$_2$H$_5$ | ▷ | H | H | (COOH)$_2$ | 0.00125 |
| Ph-CH$_2$-CH$_2$ | CO-nC$_4$H$_9$ | C$_2$H$_5$ | H | H | (COOH)$_2$ | <0.04 |

-continued

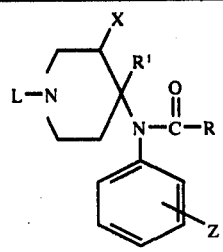
(I)

| L | R¹ | R | X | Z | Salt or base | ED$_{50}$-values in mg/kg i.v. |
|---|---|---|---|---|---|---|
| ![thiophene]-CH$_2$-CH$_2$ | COC$_2$H$_5$ | C$_2$H$_5$ | H | H | (COOH)$_2$ | 0.0008 |
| nC$_3$H$_7$ | CH$_2$-O-CH$_3$ | C$_2$H$_5$ | H | H | HCl | 0.10 |
| CH$_2$=CH-CH$_2$ | CH$_2$-O-CH$_3$ | C$_2$H$_5$ | H | H | HCl | 0.50 |
| nC$_4$H$_9$ | CH$_2$-O-CH$_3$ | C$_2$H$_5$ | H | H | HCl 1/2H$_2$O | 0.08 |
| ![cyclopropyl]-CH$_2$ | CH$_2$-O-CH$_3$ | C$_2$H$_5$ | H | H | (COOH)$_2$ | 0.10 |
| nC$_5$H$_{11}$ | CH$_2$-O-CH$_3$ | C$_2$H$_5$ | H | H | (COOH)$_2$ | 0.02 |
| nC$_6$H$_{13}$ | CH$_2$-O-CH$_3$ | C$_2$H$_5$ | H | H | (COOH)$_2$ | 0.02 |
| nC$_7$H$_{15}$ | CH$_2$-O-CH$_3$ | C$_2$H$_5$ | H | H | (COOH)$_2$ | 0.04 |
| nC$_8$H$_{17}$ | CH$_2$-O-CH$_3$ | C$_2$H$_5$ | H | H | (COOH)$_2$ | 0.25 |
| ![phenyl]-CH$_2$-CH$_2$ | CH$_2$-O-CH$_3$ | C$_2$H$_5$ | H | H | base | 0.0008 |
| F-![phenyl]-CH$_2$-CH$_2$ | CH$_2$-O-CH$_3$ | C$_2$H$_5$ | H | H | (COOH)$_2$ | 0.005 |
| CH$_3$O-![phenyl]-CH$_2$-CH$_2$ | CH$_2$-O-CH$_3$ | C$_2$H$_5$ | H | H | (COOH)$_2$ | 0.04 |
| CH$_3$-![phenyl]-CH$_2$-CH$_2$ | CH$_2$-O-CH$_3$ | C$_2$H$_5$ | H | H | (COOH)$_2$ | 0.02 |
| ![thiophene]-CH$_2$-CH$_2$ | CH$_2$-O-CH$_3$ | C$_2$H$_5$ | H | H | base | 0.0008 |
| ![phenyl]-CH$_2$-CH(CH$_3$) | CH$_2$-O-CH$_3$ | C$_2$H$_5$ | H | H | (COOH)$_2$ | 0.005 |
| ![phenyl]-CH$_2$-CH$_2$-CH$_2$ | CH$_2$-O-CH$_3$ | C$_2$H$_5$ | H | H | (COOH)$_2$ | 0.06 |
| ![phenyl]-CH(OH)-CH(CH$_3$) | CH$_2$-O-CH$_3$ | C$_2$H$_5$ | H | H | base | 0.00125 |
| ![phenyl]-CH(OH)-CH$_2$ | CH$_2$-O-CH$_3$ | C$_2$H$_5$ | H | H | HCl | 0.002 |
| ![phenyl]-CH$_2$-CH$_2$ | CH$_2$-O-CH$_3$ | nC$_3$H$_7$ | H | H | (COOH)$_2$ | 0.0025 |
| ![phenyl]-CH$_2$-CH$_2$ | CH$_2$-O-CH$_3$ | ![cyclopropyl] | H | H | HCl | 0.002 |
| ![phenyl]-CH$_2$-CH$_2$ | CH$_2$OH | C$_2$H$_5$ | H | H | HCl | 0.005 |
| ![phenyl]-CH$_2$-CH$_2$ | CH$_2$-C$_2$H$_5$ | C$_2$H$_5$ | H | H | base | 0.03 |
| ![phenyl]-CH$_2$-CH$_2$ | CH$_2$-O-nC$_3$H$_7$ | C$_2$H$_5$ | H | H | HCl | 0.25 |
| ![phenyl]-CH$_2$-CH$_2$ | CH$_2$-O-CH$_2$-![phenyl] | C$_2$H$_5$ | H | H | HCl | 0.20 |
| ![phenyl]-CH$_2$-CH$_2$ | CH$_2$-O-COC$_2$H$_5$ | C$_2$H$_5$ | H | H | (COOH)$_2$ | 0.04 |
| ![phenyl]-CH$_2$-CH$_2$ | COOCH$_3$ | C$_2$H$_5$ | H | 4-F | (COOH)$_2$ | 0.001 |
| ![phenyl]-CH$_2$-CH$_2$ | COOCH$_3$ | C$_2$H$_5$ | H | 3-CF$_3$ | (COOH)$_2$ | 0.04 |

-continued

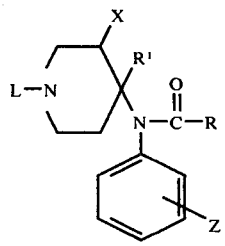
(I)

| L | R¹ | R | X | Z | Salt or base | ED$_{50}$-values in mg/kg i.v. |
|---|---|---|---|---|---|---|
| ⌬—CH₂—CH₂ | COOCH₃ | C₂H₅ | H | 3-OCH₃ | (COOH)₂ | 0.002 |
| ⌬—CH₂—CH₂ | COOCH₃ | C₂H₅ | H | 4-OCH₃ | (COOH)₂ | 0.005 |
| ⌬—CH₂—CH₂ | COOCH₃ | C₂H₅ | H | 4-CH₃ | (COOH)₂ | 0.02 |
| ⌬—NH—CH₂—CH₂ | CH₂OCH₃ | C₂H₅ | H | H | 2 HCl | 0.04 |
| (furan)—CH₂—CH₂ | CH₂OCH₃ | C₂H₅ | H | H | (COOH)₂ | 0.0025 |
| (naphthyl)—CH₂—CH₂ | CH₂OCH₃ | C₂H₅ | H | H | base | 0.01 |
| ⌬—N(CO—C₂H₅)—CH₂—CH₂ | CH₂OCH₃ | C₂H₅ | H | H | (COOH)₂ | 0.02 |
| O₂N—⌬—CH₂—CH₂ | CH₂OCH₃ | C₂H₅ | H | H | base | 0.04 |
| (pyridyl)—CH₂—CH₂ | CH₂OCH₃ | C₂H₅ | H | H | base | 0.005 |
| ⌬—CH(O—CO—C₂H₅)—CH₂ | CH₂OCH₃ | C₂H₅ | H | H | 1 1/2(COOH)₂ | 0.01 |
| H₂N—⌬—CH₂—CH₂ | CH₂OCH₃ | C₂H₅ | H | H | base | 0.02 |
| ⌬—CH₂—CH₂ | —COCH₃ | C₂H₅ | H | 4-CH₃ | base | 0.02 |
| ⌬—CH₂—CH₂ | —COCH₃ | C₂H₅ | H | 4-F | base | 0.00125 |

The following examples are intended to illustrate, and not to limit the scope of the present invention. Unless otherwise stated all parts therein are by weight.

EXAMPLE I

A mixture of 50 parts of 4-N-anilino-1-benzyl-4-carbamoylpiperidine and 600 parts of concentrated hydrochloric acid solution is refluxed for 16 hours. After cooling the reaction mixture is concentrated under diminished pressure to a volume of 400 parts, whereupon a precipitate is formed. It is filtered off, washed with water and acetone and dried, yielding 4-N-anilino-1-benzyl-4-carboxy-piperidine dihydrochloride; mp. 261°–263° C (dec.).

A stirred suspension of 1500 parts of 4-N-anilino-1-benzyl-4-carboxy-piperidine dihydrochloride in 3000 parts of water is alkalized with an excess of a concentrated sodium hydroxide solution. After cooling to room temperature, the precipitated product is filtered off and suspended in 1500 parts of ice-water. The crude product is filtered off and crystallized three times from water, yielding sodium 4-(phenylamino)-1-(phenylmethyl)-4-piperidinecarboxylate; mp. +300° C (dec.).

A mixture of 66.4 parts of sodium 4-(phenylamino)-1-(phenylmethyl)-4-piperidinecarboxylate in 375 parts of hexamethylphosphoric triamide is heated to 70° C. After cooling to 10° C, 31.2 parts of iodomethane are added (slightly exothermic reaction). The whole is stirred for 21 hours at room temperature. The reaction mixture is diluted with 360 parts of methylbenzene. The whole is washed with water and the layers are separated. The aqueous phase is washed with methylbenzene. The combined organic layers are washed successively once with 300 parts of a 10% sodium hydroxide solution and twice with 300 parts of water, dried, filtered and evaporated, yielding methyl 4-(phenylamino)-1(phenylmethyl)-4-piperidinecarboxylate as a residue.

A mixture of 47.2 parts of methyl 4-(phenylamino)-1-(phenylmethyl)-4-piperidinecarboxylate and 130.1 parts of propanoic acid anhydride is stirred and refluxed for 6 hours. The reaction mixture is cooled, poured onto 1000 parts of water and the whole is alkalized with ammonium hydroxide. The product is extracted with 450 parts of trichloromethane. The extract is washed twice with water, dried, filtered and evaporated. The residue is purified by column-chromatography over silica gel using a mixture of trichloromethane and 5% of methanol as eluent. The pure fractions are collected and the eluent is evaporated, yielding methyl 4-[N-(1-oxopropyl)-N-phenylamino]-1-(phenylmethyl)-4-piperidinecarboxylate as a residue.

A mixture of 46.2 parts of methyl 4-[N-(1-oxopropyl)-N-phenylamino]-1-(phenylmethyl)-4-piperidinecarboxylate and 300 parts of acetic acid is hydrogenated at normal pressure and at room temperature with 10 parts of palladium-on-charcoal catalyst. After the calculated amount of hydrogen is taken up, the catalyst is filtered off. The filtrate is evaporated and 300 parts of water are added to the residue. The whole is alkalized with ammonium hydroxide and the product is extracted with trichloromethane. The extract is washed twice with water, dried, filtered and evaporated. The residue is purified by column-chromatography over silica gel using a mixture of trichloromethane and 5% of methanol, saturated with ammonia, as eluent. The pure fractions are collected and the eluent is evaporated. The residue is dissolved in 140 parts of 2,2'-oxybispropane and the solution is stirred with activated charcoal. The latter is filtered off and the filtrate is evaporated. The residue is converted into the hydrochloride salt in 2-propanol and 4-methyl-2-pentanone. The salt is filtered off and crystallized twice from 4-methyl-2-pentanone, yielding methyl 4-[N-(1-oxopropyl)-N-phenylamino]-4-piperidinecarboxylate hydrochloride; mp. 168.7° C.

EXAMPLE II

To a stirred mixture of 11.5 parts of 4-N-anilino-1-benzyl-4-carboxy-piperidine dihydrochloride, 0.24 parts of N,N-dimethylformamide and 14 parts of chlorobenzene are added 2.24 parts of thionyl chloride. After the addition is complete, the whole is first stirred for 2 hours at room temperature and then heated at 90°-95° C for 45 minutes. After cooling there are added 40 parts of 4-N-anilino-1-benzyl-4-chloro-carbonyl-piperidine. The whole is stirred for 24 hours at room temperature. The excess of ethanol is evaporated. The residue is dissolved in dilute hydrochloric acid. This solution is first extracted with toluene and then alkalized with sodium hydroxide, followed by extraction with chloroform. The organic layer is dried over magnesium sulfate, filtered and evaporated. The oily residue is dissolved in 120 parts of diisopropylether and gaseous hydrogen chloride is introduced into the solution. The precipitated hydrochloride is filtered off, boiled in 40 parts of 2-propanol and filtered off again from the hot solution. After drying, crude 4-N-anilino-1-benzyl-4-(ethoxy-carbonyl-piperidine dihydrochloride is obtained. This crop is recrystallized from a mixture of 24 parts ethanol and 24 parts of 2-propanol. After filtering and drying 4-N-anilino-1-benzyl-4-(ethoxy-carbonyl)-piperidine dihydrochloride is obtained; mp. 207.5°-211° C.

A mixture of 101.5 parts of ethyl 4-anilino-1-benzylisonipecotate and 292.8 parts of propanoic acid anhydride is stirred and refluxed for 6 hours. The reaction mixture is poured onto crushed ice and the whole is alkalized with ammonium hydroxide. The product is extracted with trichloromethane. The extract is washed successively with a diluted ammonium hydroxide solution and with water, dried, filtered and evaporated. The residue is converted into the ethanedioate salt in 400 parts of 2-propanol. The salt is filtered off and crystallized three times from 2-propanol, yielding ethyl 4-[N-(1-oxopropyl)-N-phenylamino]-1-(phenylmethyl)-4-piperidinecarboxylate ethanedioate; mp. 196° C.

A mixture of 76 parts of ethyl 4-[N-(1-oxopropyl)-N-phenylamino]-1-(phenylmethyl)-4-piperidinecarboxylate and 250 parts of acetic acid is hydrogenated at 20 lbs./sq. inch and at room temperature with 15 parts of palladium-on-charcoal catalyst 10%. After the calculated amount of hydrogen is taken up, the catalyst is filtered off. The filtrate is evaporated and the residue is dissolved in water. The solution is alkalized with ammonium hydroxide. The product is extracted with dichloromethane. The extract is washed with water, dried, filtered and evaporated. The oily residue is purified by column-chromatography over silica gel, using a mixture of trichloromethane and 10% of methanol as eluent. The pure fractions are collected and the eluent is evaporated. The residue is converted into the ethanedioate salt in 2-propanone. The salt is filtered off and washed with 2-propanone, yielding, after drying, ethyl 4-[N-(1-oxopropyl)-N-phenylamino]-4-piperidinecarboxylate ethanedioate; mp. 206.8° C.

EXAMPLE III 100 parts of sodium-4-(phenylamino)-1-(phenylmethyl)-4-piperidinecarboxylate are dissolved in 565 parts of anhydrous hexamethylphosphoric triamide at 70°-80° C. The solution is cooled to 10° C and 40.6 parts of 1-bromopropane are added dropwise. Upon completion, stirring is continued for 25 hours at room temperature. Then there are added methylbenzene and water. The organic phase is separated, washed successively with water, 10% of sodium hydroxide solution and again with water, dried, filtered and evaporated. The residue is dissolved in hexane and the solution is allowed to stand overnight at room temperature. It is filtered and the filtrate is evaporated. The residue is converted into the ethanedioate salt in 2-propanone. The salt is filtered off and dried, yielding propyl 4-(phenylamino)-1-(phenylmethyl)-4-piperidecarboxylate ethanedioate; mp. 192.2° C.

260 parts of propanoic acid anhydride are added dropwise to 93 parts of propyl 4-(phenylamino)-1-(phenylmethyl)-4-piperidinecarboxylate while cooling in a water-bath. Upon completion, the whole is stirred and refluxed for 6 hours. After cooling, the reaction mixture is poured onto water, alkalized with ammonium hydroxide and the product is extracted with trichloromethane. The extract is washed with water, dried, filtered and evaporated. The residue is dissolved in petroleumether. The solution is filtered and the filtrate is evaporated. The oily residue is converted into the ethanedioate salt in 2-propanone. The salt is filtered off and crystallized from a mixture of 2-propanone and ethanol (10:1 by volume), yielding propyl 4-[N-(1-oxopropyl)-N-phenylamino]-1-(phenylmethyl)-4-piperidinecarboxylate ethanedioate; mp. 169.7° C.

A mixture of 93 parts of propyl 4-[N-(1-oxopropyl)-N-phenylamino]-1-(phenylmethyl)-4-piperidinecarboxylate and 160 parts of butanol is hydrogenated at normal pressure and at room temperature with 10 parts of palladium-on-charcoal catalyst 10%. After the calculated amount of hydrogen is taken up, the catalyst is filtered off and the filtrate is evaporated. The oily residue is purified by column-chromatography over silicagel using a mixture of trichloromethane and 5% of methanol, saturated with gaseous ammonia, as eluent. The pure fractions are collected and the eluent is evaporated. The residue is converted into the hydrochloride salt in 1,1′-oxybisethane, yielding propyl 4-[N-(1-oxopropyl)-N-phenylamino]-4-piperidinecarboxylate hydrochloride; mp. 173.3° C.

EXAMPLE IV

A mixture of 21 parts of 4-N-(N-acetyl-anilino)-1-benzyl-4-(ethoxy-carbonyl)-piperidine, 100 parts of ethanol, 6 parts of a concentrate hydrochloric acid solution and 10 parts of distilled water is hydrogenated at normal pressure and at a temperature of 40° C, in the presence of 4 parts palladium-on-charcoal catalyst. After the calculated amount of hydrogen is taken up, hydrogenation is stopped. The charcoal is filtered off and the filtrate is evaporated. The semi-solid is dissolved in water. The aqueous solution is alkalized with ammonium hydroxide and extracted with toluene. The organic layer is dried over magnesium sulfate, filtered and evaporated. The oily residue is dissolved in 40 parts of diisopropylether. After cooling to 0° C, 10.5 parts of 4-N-(N-acetyl-anilino)-4-(ethoxycarbonyl)-pipéridine are obtained; mp. 72.4°–73.8° C.

EXAMPLE V

A mixture of 19 parts of 4-N-anilino-1-benzyl-4-carboxypiperidine dihydrochloride, 14.4 parts of sulfuric acid and 64 parts of ethanol is stirred and refluxed for 16 hours. The solvent is decanted. The residue is dissolved in water. The aqueous solution is alkalized with ammonium hyroxide and extracted with a mixture of toluene and diisopropylether. The combined organic layers are dried over magnesium sulfate, filtered and evaporated. The oily residue is dissolved in 200 parts diisopropylether and gaseous hydrogen chloride is introduced into the solution. The precipitated hydrochloride is filtered off, washed with 2-propanol, filtered off again and dried, yielding 11.5 parts of 4-N-anilin0-1-benzyl-4-(ethoxy-carbonyl)-piperidine dihydrochloride; mp. 212°–214.4° C.

To a stirred and refluxing solution of 101.4 parts of ethyl 4-anilino-1-benzyl-4-piperidinecarboxylate in 640 parts of dry benzene is added dropwise a solution of 172 parts of sodium dihydro-bis(2-methoxyethoxy)aluminate 70% solution in benzene, in 160 parts of dry benzene. Upon completion, stirring is continued for 2h. 30 at 80° C. The reaction mixture is cooled, poured onto ice-water, alkalized with sodium hydroxide solution and the product is extracted with benzene. The extract is washed twice with water, dried, filtered and evaporated. The residue is converted into the hydrochloride salt in 2-propanol and ether. The salt is filtered off, boiled in 2-propanol and after cooling, the product is filtered off. It is boiled once more in acetonitrile and the salt is filtered off again after cooling. The free base is liberated in the conventional manner. After extraction with ether, the latter is washed with water, dried and evaporated, yielding 4-anilino-1-benzyl-4-piperidinemethanol as an oily residue.

To a stirred mixture of 11 parts of 4-anilino-1-benzyl-4-piperidinemethanol and 60 parts of hexamethylphosphoric triamide is added portionwise 1 part of sodium hydride dispersion 78% at room temperature. After stirring for two hours at room temperature, there are added dropwise 4.8 parts of iodomethane. Upon completion, stirring at room temperature is continued overnight. The reaction mixture is poured onto water and the product is extracted with benzene. The extract is washed with water, dried, filtered and evaporated. The oily residue is purified by column-chromatography over silicagel using a mixture of trichloromethane and 3% of methanol, saturated with gaseous ammonia, as eluent. The pure fractions are collected and the eluent is evaporated. The oily residue is converted into the hydrochloride salt in 1,1′-oxybisethane and 2-propanol. The salt is filtered off and dried, yielding 4-(methoxymethyl)-N-phenyl-1-(phenylmethyl)-4-piperidinamine dihydrochloride; mp. 240.5° C.

A mixture of 7 parts of 4-(methoxymethyl)-N-phenyl-1-(phenylmethyl)-4-piperidinamine and 15 parts of propanoic acid anhydride is stirred and refluxed for 6 hours. After cooling, the reaction mixture is poured onto ice-water and alkalized with ammonium hydroxide. The product is extracted with trichloromethane. The extract is washed with water, dried, filtered and evaporated. The oily residue is converted into the ethanedioate salt in 1,1′-oxybisethane and 2-propanol. The sticky salt is triturated in 2-propanone. The product is filtered off and crystallized from 96 parts of acetonitrile, yielding N-[4-(methoxymethyl)-1-(phenylmethyl)-4-piperidinyl]-N-phenylpropanamide ethanedioate; mp. 191.2° C.

A mixture of 52 parts of N-[4-(methoxymethyl)-1-(phenylmethyl)-4-piperidinyl]-N-phenylpropanamide and 200 parts of acetic acid is hydrogenated at normal pressure and at room temperature with 3 parts of palladium-on-charcoal catalyst 10%. After the calculated amount of hydrogen is taken up, the catalyst is filtered off and the filtrate is evaporated. The residue is taken up in water, cooled and alkalized with ammonium hydroxide. The product is extracted with trichloromethane. The extract is washed with water, dried, filtered and evaporated, yielding N-[4-(methoxymethyl)-4-piperidinyl]-N-phenylpropanamide as an oily residue.

EXAMPLE VI

To a stirred mixture of 45 parts of 4-anilino-1-benzyl-4-piperidinemethanol and 240 parts of hexamethylphosphoric triamide are added portionwise 4.2 parts of sodium hydride dispersion 78% and the whole is stirred for 2 hours at room temperature. Then there are added dropwise 21.5 parts of iodoethane (exothermic reaction). The reaction mixture is poured onto water and the product is extracted with benzene. The extract is washed thoroughly with water, dried, filtered and evaporated. The oily residue is purified by column-chromatography over silicagel using a mixture of trichloromethane and 5% of methanol saturated with ammonia, as eluent. The pure fractions are collected and the eluent is evaporated. The residue is converted into the hyrochloride salt in 1,1′-oxybisethane. The salt is filtered off, dried and crystallized from 2-propanol and a few drops of ethanol. The product is filtered off and dried, yielding 4-(ethoxymethyl)-N-phenyl-1-(phenylmethyl)-4-piperidinamine dihydrochloride; mp. 238.4° C.

A mixture of 17.5 parts of 4-(ethoxymethyl)-N-phenyl-1-(phenylmethyl)-4-piperidinamine and 36 parts of propionic acid anhydride is stirred and refluxed for 6 hours. The reaction mixture is poured onto ice-water and the whole is basified with ammonium hydroxide. The product is extracted with trichloromethane. The extract is washed with water, dried, filtered and evaporated. The residue is converted into the ethanedioate salt in 2-propanone. The salt is filtered off and crystallized from 2-propanol (135 parts). The product is filtered off and dried, yielding N-[4-(ethoxymethyl)-1-(phenylmethyl)-4-piperidinyl]-N-phenylpropanamide ethanedioate; mp. 181.2° C.

A mixture of 14.4 parts of N-[4-(ethoxymethyl)-1-(phenylmethyl)-4-piperidinyl]-N-phenylpropanamide and 200 parts of acetic acid is hydrogenated at normal pressure and at room temperature with 2 parts of palladium-on-charcoal catalyst 10%. After the calculated amount of hydrogen is taken up, the catalyst is filtered off and the filtrate is evaporated. The residue is taken up in water, cooled and basified with ammonium hydroxide. The product is extracted with trichloromethane. The extract is washed with water, dried, filtered and evaporated, yielding N-[4-(ethoxymethyl)-4-piperidinyl]-N-phenylpropanamide as an oily residue.

EXAMPLE VII

To a stirred mixture of 60 parts of 4-anilino-1-benzyl-4-piperidinemethanol and 320 parts of hexamethylphosphoric triamide are added portionwise 5.5 parts of sodium hydride dispersion 78% at room temperature. After stirring for 2 hours, there are added dropwise 30.8 parts of 1-iodopropane. Upon completion, stirring at room temperature is continued overnight. The reaction mixture is poured onto water and the product is extracted with benzene. The extract is washed with water, dried, filtered and evaporated. The oily residue is purified by column-chromatography over silica gel using a mixture of trichloromethane and 4% of methanol, saturated with ammonia, as eluent. The pure fractions are collected and the eluent is evaporated. The oily residue is converted into the hyrochloride salt in 1,1'-oxybisethane and 2-propanol. The salt is filtered off and crystallized from 2-propanol. The product is filtered off and dried, yieldling N-phenyl-1-(phenylmethyl)-4-(propoxymethyl)-4-piperidinamine dihydrochloride; mp. 220.2° C.

A mixture of 13.1 parts of N-phenyl-1-(phenylmethyl)-4-(propoxymethyl)-4-piperidinamine and 20 parts of propionic acid anhydride is stirred and refluxed for 6 hours. After cooling, the reaction mixture is poured onto ice-water and the whole is alkalized with ammonium hydroxide. The product is extracted with trichloromethane. The extract is washed with water, dried, filtered and evaporated. The oily residue is converted into the ethanedioate salt in 2-propanone and 2-propanol. The salt is filtered off and crystallized from acetonitrile, yielding N-phenyl-N-[1-(phenylmethyl)-4-(propoxymethyl)-4-piperidinyl]propanamide ethanedioate; mp. 180.3° C.

A mixture of 12 parts of N-phenyl-N-[1-(phenylmethyl)-4-(propoxymethyl)-4-piperidinyl]propanamide and 200 parts of acetic acid is hydrogenated at 20 lbs/sq. inch and at room temperature with 3 parts of palladium-on-charcoal catalyst 10%. After the calculated amount of hydrogen is taken up, the catalyst is filtered off. The filtrate is evaporated. The oily residue is dissolved in water and the solution is alkalized with ammonium hydroxide. The product is extracted with trichloromethane. The extract is washed with water, dried, filtered and evaporated. The oily residue is converted into the ethanedioate salt in 2-propanone. The salt is filtered off and crystallized twice: first from acetonitrile and then from 2-propanol, yielding N-phenyl-N-[4-(propoxymethyl)-4-piperidinyl]propanamide ethanedioate; mp. 180° C.

EXAMPLE VIII

A solution of 16.9 parts of ethyl 4-anilino-1-benzylisonipecotate in 150 parts of acetic acid is hydrogenated at normal pressure and at a temperature of 45° C with 1.5 parts of palladium-on-charcoal 10%. After the calculated amount of hydrogen is taken up, the reaction mixture is allowed to cool to room temperature, the catalyst is filtered off and the filtrate is evaporated. The oily residue is taken up in water, alkalized with ammonium hydroxide and the product is extracted with chloroform. The extract is washed with water, dried, filtered and evaporated. The oily residue solidifies on triturating in petroleumether. The product is filtered off and crystallized from acetonitrile, yielding ethyl 4-anilinoisonipecotate; mp. 121.8° C.

A mixture of 28.7 parts of (2-bromoethyl)benzene, 34.7 parts of ethyl 4-anilinoisonipecotate, 25 parts of N,N-diethylethanamine and 162 parts of N,N-dimethylacetamide is stirred for 2h. 30 at 75°–80° C. The reaction mixture is poured onto 1000 parts of water and the product is extracted three times with 210 parts of 1,1'-oxybisethane. The combined extracts are washed twice with 200 parts of water, dried, filtered and evaporated. The residue is purified by column-chromatography over silica gel using a mixture of trichloromethane and 2% of methanol as eluent. The pure fractions are collected and the eluent is evaporated. The oily residue is crystallized from 2,2'-oxybispropane, yielding ethyl 4-(phenylamino)-1-(2-phenylethyl)-4-piperidinecarboxylate; mp. 65° C.

EXAMPLE IX

To a mixture of 102 parts of 4-oxo-1-(2-phenylethyl)-piperidine, 47 parts of aniline and 350 parts of acetic acid is added dropwise a solution of 36 parts of potassium cyanide in 100 parts of water, at a temperature between 35°–45° C (exothermic reaction). After the addition is complete, the cooling-bath is removed and the whole is stirred for 20 hours at room temperature. The reaction mixture is poured into 650 parts of ammonium hydroxide and 500 parts of crushed ice are added. The mixture is extracted with chloroform. The organic extract is dried over potassium carbonate, filtered and evaporated. The residue (solid) is triturated in diisopropylether. After keeping at room temperature, 4-anilino-4-cyano-1-(2-phenylethyl)-piperidine is obtained; mp. 120°–121° C.

To 4500 parts of sulfonic acid are added portionwise 710 parts of 4-(phenylamino)-1-(2-phenylethyl)-4-piperidinecarbonitrile, while keeping the temperature below 25° C. Upon completion, stirring is continued overnight at room temperature. The reaction mixture is poured onto a mixture of 10.000 parts of crushed ice and 3600 parts of ammonium hydroxide. The product is extracted with trichloromethane (7500 parts). The extract is dried, filtered and evaporated. The residue is stirred in 140 parts of 2,2'-oxybispropane. The product is filtered off and dried, yielding 4-(phenylamino)-1-(2-phenylethyl)-4-piperidinecarboxamide; mp. 182.5° C.

A mixture of 105 parts of 4-(phenylamino)-1-(2-phenylethyl)-4-piperidinecarboxamide, 53.7 parts of potassium hydroxide and 275 parts of 1,2-ethanediol is stirred and refluxed for 20 hours. After cooling, the reaction mixture is poured onto 1000 parts of water and the whole is filtered over hyflo. The filtrate is strongly acidified with hydrochloric acid solution till the formed precipitate enters solution. The solution is strongly alkalized with a concentrated sodium hydroxide solution (exothermic reaction) and filtered warm. The sodium salt is allowed to crystallize from the filtrate. It is filtered off and recrystallized from water, yielding 4-(phenylamino)-1-(2-phenylethyl)-4-piperidinecarboxylic acid, sodium salt; mp. + 300° C (dec.).

A solution of 62.3 parts of 4-(phenylamino)-1-(2-phenylethyl)-4-piperidinecarboxylic acid, sodium salt in 28.4 parts of iodomethane is stirred and heated to 100° C. After cooling to 10° C, there are added dropwise 340 parts of hexamethylphosphoric triamide (slightly exothermic reaction). Upon completion, stirring is continued for 24 hours at room temperature. The reaction mixture is poured onto water (800 parts) and the product is extracted with methylbenzene. The extract is washed with water, dried, filtered and evaporated. The oily residue solidifies on triturating in 2,2'-oxybispropane. The product is filtered off and crystallized from 2,2'-oxybispropane, yielding methyl 4-(phenylamino)-1-(2-phenylethyl)-4-piperidinecarboxylate; mp. 94.9° C.

EXAMPLE X

A mixture of 10.4 parts of 4-(phenylamino)-1-(2-phenylethyl)-4-piperidinecarboxylic acid, sodium salt and 75 parts of hexamethylphosphoric triamide is stirred at 110° C for a while. It is cooled to 20° C and 3.7 parts of 2-bromopropane is added dropwise. After stirring for 4 hours, another 0.37 parts of 2-bromopropane is added dropwise. Upon completion, stirring is continued over week-end at room temperature. The reaction mixture is poured onto 150 parts of water and the product is extracted with methylbenzene. The extract is washed with water, dried, filtered and evaporated. The oily residue is dissolved in 1,1'-oxybisethane. The solution is stirred with activated charcoal. The latter is filtered off and the filtrate is evaporated. The oily residue is crystallized from hexane. The product is filtered off and recrystallized from hexane, yielding 1-methylethyl 4-(phenylamino)-1-(2-phenylethyl)-4-piperidinecarboxylate; mp. 78.5° C.

EXAMPLE XI

A mixture of 10.4 parts of 4-(phenylamino)-1-(2-phenylethyl)-4-piperidinecarboxylic acid, sodium salt and 75 parts of hexamethylphosphoric triamide is stirred and heated to 110° C for a while. After cooling to 20° C, 3.63 parts of 3-bromo-1-propene are added dropwise. Upon completion, stirring is continued for 20 hours at room temperature. The reaction mixture is poured onto 150 parts of water and the product is extracted with methylbenzene. The extract is washed with water, filtered and evaporated. The oily residue is purified by column-chromatography over silica gel using a mixture of trichloromethane and 5% of methanol as eluent. The pure fractions are collected and the eluent is evaporated. The oily residue is crystallized from hexane, yielding 2-propenyl 4-(phenylamino)-1-(2-phenylethyl)-4-piperidinecarboxylate; mp. 57.2° C.

EXAMPLE XII 10.4 parts of 4-(phenylamino)-1-(2-phenylethyl)-4-piperidinecarboxylic acid, sodium salt are dissolved in 75 parts of hexamethylphosphoric triamide while heating to 110° C. After cooling to 20° C, 3.4 parts of (chloromethyl)benzene are added dropwise. Upon completion, stirring is continued for 18 hours at room temperature. The reaction mixture is poured onto 300 parts of water and the product is extracted with methylbenzene. The extract is washed with water, dried, filtered and evaporated. The residue is crystallized from 2,2'-oxybispropane, yielding phenylmethyl 4-(phenylamino)-1-(2-phenylethyl)-4-piperidinecarboxylate; mp. 76.7° C.

EXAMPLE XIII

To a stirred suspension of 58.5 parts of 4-(phenylamino)-1-(2-phenylethyl)-4-piperidinecarboxylic acid, sodium salt in 300 parts of hexamethylphosphoric triamide are added dropwise 29.2 parts of iodoethane at room temperature (slightly exothermic reaction: the temperature rises to 34° C). Upon completion, stirring is continued at room temperature for 48 hours. The reaction mixture is poured onto 1000 parts of water and the product is extracted with methylbenzene. The extract is washed with water, dried, filtered and evaporated. The residue is crystallized twice: first from petroleumether and then from 35 parts of 2,2'-oxybispropane, yielding 45.2 parts of ethyl 4-(phenylamino)-1-(2-phenylethyl)-4-piperidinecarboxylate; mp. 65.4° C.

EXAMPLE XIV

To 300 parts of glacial acetic acid are added dropwise 86 parts of methyl 3-methyl-4-oxo-1-piperidinecarboxylate and 51.12 parts of aniline while keeping the temperature below 30° C. Then there is added dropwise a solution of 39 parts of potassium cyanide in a minimum quantity of water (temperature is kept below 25° C). Upon completion, the whole is stirred at room temperature over week-end. The precipitated product is filtered off, suspended in water and alkalized (slightly). The product is filtered off again and dried, yielding methyl 4-anilino-4-cyano-3-pipecoline-1-carboxylate; mp. 96.4°–129.2° C (dec.).

To 920 parts of concentrated sulfuric acid solution are added portionwise (quickly) 250 parts of methyl 4-anilino-4-cyano-3-pipecoline-1-carboxylate while cooling with ice-water to keep the temperature below 25° C. Upon completion, the whole is stirred first for 5 hours at 50° C and further overnight at room temperature. The reaction mixture is poured onto crushed ice and alkalized with ammonium hydroxide (temperature <30° C). The product is extracted with trichloromethane. The extract is washed successively with a diluted ammonium hydroxide solution and with water, dried, filtered and evaporated. The oily residue is crystallized from 20 parts of 2-propanol, yielding 85 parts of a mixture of cis and trans isomers. It is filtered off and set aside. The filtrate is evaporated. The residue is purified by column-chromatography over silica gel using successively trichloromethane, a mixture of trichloromethane and 2% of methanol and a mixture of trichloromethane and 5% of methanol as eluent. The thus-obtained fractions are collected and discarded. The fraction, collected after elution with a mixture of trichloromethane and 10% of methanol, is evaporated. The residue is crystallized from acetonitrile, yielding a first fraction of cis methyl 4-(aminocarbonyl)-3-methyl-4-(phenylamino)-1-piperidinecarboxylate; mp. 180° C. The mixture of cis and trans isomers, which was set aside (see above), is recrystallized from 640 parts of 2-propanol. The precipitate, trans methyl 4-anilino-4-carbamoyl-3-pipecoline-1-carboxylate, is filtered off. The filtrate is evaporated and the residue is crystallized from acetonitrile, yielding a second fraction of cis methyl 4-(aminocarbonyl)-3-methyl-4-(phenylamino)-1-piperidinecarboxylate; mp. 178.3° C.

A mixture of 30.6 parts of cis methyl 4-(aminocarbonyl)-3-methyl-4-(phenylamino)-1-piperidinecarboxylate, 58.8 parts of potassium hydroxide and 270 parts of 2-propanol is stirred and refluxed for 4 hours. The reaction mixture is evaporated and 400 parts of water are added to the residue. The mixture is further evaporated to remove all traces of 2-propanol. The precipitated product is filtered off and shaken with 3000 parts of trichloromethane. The undissolved product is filtered off and dried, yielding a first fraction of cis 3-methyl-4-(phenylamino)-4-piperidinecarboxamide; mp. 220° C. The mother-liquor is washed with water, dried, filtered and evaporated in vacuo, yielding a second fraction of cis 3-methyl-4-(phenylamino)-4-piperidinecarboxamide; mp. ±220° C.

A mixture of 20.5 parts of (2-bromoethyl)benzene, 23.3 parts of cis 3-methyl-4-(phenylamino)-4-piperidinecarboxamide, 17.5 parts of N,N-diethylethanamine and 105 parts of dimethylacetamide is stirred for 4h. 30 at 75° C. The reaction mixture is cooled and poured onto 750 parts of water. The formed precipitate is filtered off and dissolved in trichloromethane. The solution is washed twice with water, dried, filtered and evaporated. The residue is suspended in 2,2'-oxybispropane. The crude product is filtered off and purified by column-chromatography over silica gel using a mixture of trichloromethane and 5% of methanol as eluent. The pure fractions are collected and the eluent is evaporated, yielding cis 3-methyl-4-(phenylamino)-1-(2-phenylethyl)-4-piperidinecarboxamide; mp. 187.8° C.

A mixture of 17.5 parts of cis 3-methyl-4-(phenylamino)-1-(2-phenylethyl)-4-piperidinecarboxamide, 14.3 parts of potassium hydroxide and 74 parts of 1,2-ethanediol is stirred and refluxed for 40 hours in an oil-bath at 220°-230° C. The reaction mixture is cooled and poured onto 430 parts of water. The mixture is filtered and the filtrate is acidified with a concentrated hydrochloric acid solution. The whole is alkalized strongly with a concentrated sodium hydroxide solution. The formed oil is separated and dissolved in water. The solution is strongly alkalized with a concentrated sodium hydroxide solution, whereupon an oil is precipitated. The aqueous phase and the oil are washed with 1,1'-oxybisethane. The aqueous phase is separated and further saturated with a concentrated sodium hydroxide solution. The precipitated product is filtered off, washed on the filter with 2-propanone and 1,1'-oxybisethane, and dried in vacuo at 80° C, yielding cis 3-methyl-4-(phenylamino)-1-(2-phenylethyl)-4-piperidinecarboxylic acid sodium salt, hydrate.

12.8 parts of cis 3-methyl-4-(phenylamino)-1-(2-phenylethyl)-4-piperidinecarboxylic acid sodium salt are dissolved in 87 parts of hexamethylphosphoric triamide at 60°-70° C. The solution is cooled in ice-water till a temperature of 16° C. Then there are added dropwise 2.43 parts of iodomethane (exothermic reaction: temperature rises to 24° C). Upon completion, stirring is continued for 24 hours at room temperature. The reaction mixture is poured onto 200 parts of water and the product is extracted twice with methylbenzene. The combined extracts are washed a few times with water, dried, filtered and evaporated, yielding cis methyl 3-methyl-4-(phenylamino)-1-(2-phenylethyl)-4-piperidinecarboxylate; mp. 100.4° C.

EXAMPLE XV 13.7 parts of methyl 4-anilino-4-cyano-3-pipecoline-1-carboxylate are added dropwise to 54 parts of a concentrated sulfuric acid (exothermic reaction:temperature rises to about 45° C). Upon completion, the mixture is stirred first for 5 hours at about 50° C and further overnight at room temperature. Crushed ice (300 parts) is added. The mixture is alkalized with sodium hydroxide solution and the product is extracted with chloroform. The organic layer is dried, filtered and evaporated. The residue is crystallized from 2-propanol, yielding trans methyl 4-anilino-4-carbamoyl-3-pipecoline-1-carboxylate; mp. 134° C.

A mixture of 47.2 parts of trans methyl 4-anilino-4-carbamoyl-3-pipecoline-1-carboxylate, 89.6 parts of potassium hydroxide and 410 parts of 2-propanol is stirred and refluxed for 3 hours. The reaction mixture is allowed to cool to room temperature overnight. The formed precipitate is filtered off and discarded. The filtrate is evaporated. The residue is dissolved in 400 parts of water. The resulting solution is evaporated till a precipitate is formed. After cooling, the precipitate is filtered off and dissolved in trichloromethane. The solution is washed with water, dried, filtered and evaporated, yielding trans 3-methyl-4-(phenylamino-4-piperidinecarboxamide; mp. 188° C.

A mixture of 19.4 parts of (2-bromoethyl)benzene, 22.5 parts of trans 3-methyl-4-(phenylamino)-4-piperidinecarboxamide, 14.4 parts of N,N-diethylethanamine and 135 parts of N,N-dimethylacetamide is stirred for 4 hours at 70° C. The reaction mixture is allowed to cool to room temperature, poured onto 750 parts of water and the product is extracted with trichloromethane. The extract is washed three times with water, dried, filtered and evaporated in vacuo. The residue is purified by column-chromatography over silica gel using a mixture of trichloromethane and 5% of methanol as eluent. The pure fractions are collected and the eluent is evaporated, yielding trans 3-methyl-4-(phenylamino)-1-(2-phenylethyl)-4-piperidinecarboxamide; mp. 156.6° C.

A mixture of 5.4 parts of trans 3-methyl-4-(phenylamino)-1-(2-phenylethyl)-4-piperidinecarboxamide, 2.7 parts of potassium hydroxide and 13.75 parts of 1,2-ethanediol is stirred and heated in an oil-bath at 220°-230° C for 25 hours. The reaction mixture is cooled and poured onto 125 parts of water. The whole is filtered, the filtrate is acidified with a hydrochloric acid solution and extracted with trichloromethane. The aqueous phase is separated and alkalized with a concentrated sodium hydroxide solution. The formed precipitate is filtered off, washed with 2-propanol and 1,1'-oxybispropane and crystallized from a mixture of 20 parts of ethanol and 3 parts of water, yielding trans 3-methyl-4-(phenylamino)-1-(2-phenylethyl)-4-piperidinecarboxylic acid sodium salt. hydrate; mp. 253°–254° C.

To a stirred and cooled (10° C) solution of 5.6 parts of trans 3-methyl-4-(phenylamino)-1-(2-phenylethyl)-4-piperidinecarboxylic acid sodium salt in 38 parts of hexamethylphosphoric triamide is added 1 part of iodomethane. Stirring is continued first for 15 minutes while still cooling in a water-bath and further for 20 hours at room temperature. The reaction mixture is poured onto 100 parts of water and the product is extracted twice with benzene. The combined extracts are washed three times with water, dried, filtered and evaporated. The residue is purified by column-chromatography over silica gel using a mixture of benzene and 1% of methanol as eluent. The pure fractions are collected and the eluent is evaporated, yielding trans - methyl 3-methyl-4-(phenylamino)-1-(2-phenylethyl)-4-piperidinecarboxylate as a residue.

EXAMPLE XVI

A mixture of 60 parts of phenylmethyl 4-(phenylamino)-1-(2-phenylethyl)-4-piperidinecarboxylate and 320 parts of methanol is hydrogenated at normal pressure and at room temperature with 10 parts of palladium-on-charcoal catalyst 10%. Upon the addition of a concentrated ammonium hydroxide solution, the precipitate, which is formed during the hydrogenation, is dissolved. The catalyst is filtered off and the filtrate is concentrated. Methanol is added and the whole is concentrated again. After cooling to room temperature the product is filtered off and dried in vacuo at 120° C, yielding 43.7 parts of 4-(phenylamino-1-(2-phenylethyl)-4-piperidinecarboxylic acid; mp. 268° C.

To start the reaction, a small amount of a solution of 78.1 parts of iodomethane in 70 parts of dry 1,1'-oxybisethane is dropped to a stirred solution of 6.9 parts of lithium in 70 parts of dry 1,1'-oxybisethane. After the addition of 70 parts of dry 1,1'-oxybisethane, the remainder of the solution is added dropwise at reflux temperature. Stirring at reflux is continued for 30 minutes. Then there were added portionwise 16.2 parts of 4-(phenylamino)-1-(2-phenylethyl)-4-piperidinecarboxylic acid (a violent reaction occurs whereby reflux temperature is maintained). Upon completion, stirring at reflux is continued for 1h. 30. The reaction mixture is decomposed by the dropwise addition of 300 parts of water. The organic phase is separated, washed with water, dried, filtered and evaporated. The residue is purified by column-chromatography over silica gel using a mixture of trichloromethane and 5% of methanol as eluent. The first fraction is collected and the eluent is evaporated. The residue is crystallized from 14 parts of 2,2'-oxybispropane, yielding 1-[4-(phenylamino)-1-(2-phenylethyl)-4-piperidinyl]ethanone; mp. 100.6° C.

EXAMPLE XVII

To a stirred and cooled (−5° C) suspension of 16.2 parts of 4-(phenylamino)-1-(2-phenylethyl)-4-piperidinecarboxylic acid in 525 parts of dry 1,1'-oxybisethane, are added dropwise 228.5 parts of 1-lithiumbutane solution 20% in hexane at 0° C. Upon completion, stirring is continued for 3 hours at 0° C. The reaction mixture is decomposed by addition of 300 parts of water. The organic phase is separated, washed with water, dried, filtered and evaporated. The oily residue is purified by column-chromatography over silica gel using a mixture of trichloromethane and 2.5% of methanol as eluent. The pure fractions are collected and the eluent is evaporated. The oil residue is dissolved in 2,2'-oxybispropane and the solution is stirred with activated charcoal. The latter is filtered off and the filtrate is evaporated. The residue is crystallized from petroleum-ether, yielding 1-[4-(phenylamino)-1-(2-phenylethyl)-4-piperidinyl]-1-pentanone; mp. 71.3° C.

EXAMPLE XVIII

A suspension of 76.6 parts of 1-benzyl-4-anilinoisonipecotic acid dihydrochloride in water is alkalized with sodium hydroxide solution. The whole is filtered and the filtrate is allowed to crystallize. The product is filtered off and triturated in ice-water. It is filtered off again and washed successively with methanol and diisopropylether, and dried. The fraction is further hydrogenated in 400 parts of water and 10 parts of palladium-on-charcoal catalyst 5%. After the calculated amount of hydrogen is taken up, the catalyst is filtered off and the filtrate is evaporated. The residue is evaporated twice more with benzene. The residue is dried, yielding 4-anilinoisonipecotic acid, sodium salt.

To a stirred and cooled (ice-salt bath) mixture of 12.1 parts of 4-anilinoisonipecotic acid, sodium salt, 200 parts of sodium hydroxide solution 1N and 20 parts of tetrahydrofuran are added dropwise 6.45 parts of ethyl chloroformate in 25 parts of tetrahydrofuran over 15 minutes and at a temperature between 2° and 5° C. Upon completion, stirring is continued for 3 hours in the cool-bath. The whole is extracted with ether. The aqueous phase is separated and degassed on a rotavapor without heating. The mixture is acidified with glacial acetic acid, whereupon an oil is separated. The latter is stirred in fresh water and extracted with chloroform. The extract is washed three times with water, dried, filtered and evaporated. The residue is crystallized from a mixture of ethyl acetate and petroleumether, yielding 4-anilino-1-(ethoxycarbonyl-isonipecotic acid; mp. 149°–156° C.

Phosgene gas is introduced through a stirring mixture of 29.2 parts of 4-anilino-1-(ethoxycarbonyl)isonipecotic acid in 240 parts of dioxane; exothermic reaction (temperature rises to 45° C). Stirring is continued for 30 minutes at 45° C. The mixture is heated to reflux and phosgene gas is gently introduced for 2h.30. Then nitrogen gas is introduced for 30 minutes. The reaction mixture is evaporated in a boiling water-bath for 30 minutes. The solid residue is triturated in ether, yielding ethyl 2,4-dioxo-1-phenyl-3-oxa-1,8-diazaspiro[4,5]decane-8-carboxylate; mp. 210.7° C.

A Grignard-complex, ethyl magnesium bromide, is prepared in the conventional manner, starting from 10.57 parts of 1-bromoethane and 2.14 parts of magnesium in 27 parts of dry tetrahydrofuran. This complex is added dropwise to a warm suspension of 25.7 parts of ethyl 2,4-dioxo-1-phenyl-3-oxa-1,8-diazaspiro[4,5]-decane-8-carboxylate in 213 parts of dry tetrahydrofuran: exothermic reaction. Upon completion, stirring is continued for 1 hour at room temperature. After cooling, the reaction mixture is decomposed by dropwise addition of an ammonium chloride solution. The layers are separated and the aqueous phase is extracted with 1,1'-oxybisethane. The combined organic phases are washed with water, dried, filtered and evaporated. The residue is purified by column-chromatography over silica gel using a mixture of trichloromethane and 3% of methanol as eluent. The pure fractions are collected and the eluent is evaporated, yielding ethyl 4-(1-oxopropyl)-4-(phenylamino)-1-piperidinecarboxylate as a residue.

A mixture of 10.2 parts of ethyl 4-(1-oxopropyl)-4-(phenylamino)-1-piperidinecarboxylate, 19.8 parts of potassium hydroxide and 90 parts of 2-propanol is stirred and refluxed for 4 hours. The reaction mixture is evaporated and 200 parts of water are added to the residue. The whole is concentrated to a volume of about 100 parts. The product is extracted with trichloromethane. The extract is washed with water, dried, filtered and evaporated. The residue is purified by column-chromatography over silica gel using a mixture of trichloromethane and 10% of methanol, previously saturated with ammonia, as eluent. The pure fractions are collected and the eluent is evaporated, yielding 1-[4-(phenylamino)-4-piperidinyl]-1-propanone as a residue.

EXAMPLE XIX

To a stirred and cooled mixture of 13 parts of 2-thiopheneethanol and 15.3 parts of triethyl amine in 120 parts of methylene chloride are added dropwise 12.7 parts of mesyl chloride at a temperature of about 0° C. Upon completion, stirring is continued for 30 minutes. The reaction mixture is washed with ice-water. The organic layer is separated, dried, filtered and evaporated. The residue is taken up in an equal volume of diisopropylether and the whole is evaporated again, yielding 2-thiopheneethanol, methanesulfonate ester as a residue.

A mixture of 4.1 parts of 2-thiopheneethanol, methanesulfonate ester, 3.5 parts of 1-[4-(phenylamino)-4-piperidinyl]-1-propanone, 5.3 parts of sodium carbonate and 120 parts of 4-methyl-2-pentanone is stirred and refluxed for 18 hours. After cooling to room temperature, the reaction mixture is poured onto water and the layers are separated. The organic phase is dried, filtered and evaporated. The oily residue is purified by column-chromatography over silica gel using a mixture of trichloromethane and 5% of methanol as eluent. The pure fractions are collected and the eluent is evaporated. The solid residue is crystallized from 2,2'-oxybispropane. The product is filtered off and dried, yielding 1-{4-(phenylamino)-1-[2-(2-thienyl)ethyl]-4-piperidinyl}-1-propanone; mp. 127.1° C.

EXAMPLE XX

To a solution of 32 parts of 4-anilino-1-benzyl-4-piperidinemethanol in 90 parts of benzene are added 0.2 parts of N,N,N-triethylbenzenemethanaminium chloride and 150 parts of sodium hydroxide solution 60%. After stirring vigourously, there are added dropwise 10.9 parts of dimethyl sulfate at a temperature below 30° C. Upon completion, stirring is continued at room temperature, first for 2h.30 and further, after the addition of a second portion of 2.6 parts of dimethyl sulfate, for 1h.30. The reaction mixture is cooled in icewater and 200 parts of water are added. The organic phase is separated and the aqueous phase is extracted with benzene. The combined organic phases are washed with water, dried, filtered and evaporated. The residue is purified by column-chromatography over silica gel using a mixture of trichloromethane and 3% of methanol, saturated with ammonia, as eluent. The pure fractions are collected and the eluent is evaporated, yielding 4-(methoxymethyl)-N-phenyl-1-(phenylmethyl)-4-piperidinamine as a residue.

A mixture of 10 parts of 4-(methoxymethyl)-N-phenyl-1-(phenylmethyl)-4-piperidinamine and 200 parts of acetic acid is hydrogenated at normal pressure and at room temperature with 2 parts of palladium-on-charcoal catalyst 10%. After the calculated amount of hydrogen is taken up, the catalyst is filtered off and the filtrate is evaporated. The oily residue is dissolved in water, cooled and alkalized with ammonium hydroxide. The product is extracted with trichloromethane. The extract is washed with water, dried, filtered and evaporated. The oily residue is purified by column-chromatography over silica gel using a mixture of trichloromethane and 10% of methanol, saturated with gaseous ammonia, as eluent. The pure fractions are collected and the eluent is evaporated, yielding 4-(methoxymethyl)-N-phenyl-4-piperidinamine as an oily residue.

A mixture of 2 parts of 2-bromoethylbenzene, 2.2 parts of 4-(methoxymethyl)-N-phenyl-4-piperidinamine, 0.1 parts of potassium iodide, 1.6 parts of sodium carbonate and 48 parts of 4-methyl-2-pentanone is stirred and refluxed over week-end with water-separator. The reaction mixture is poured onto water and the organic layer is separated, washed with water, dried, filtered and evaporated. The oily residue is converted into the hydrochloride salt in 1,1'-oxybisethane and 2-propanol. The salt is filtered off, crystallized from 1,1'-oxybisethane (activated charcoal), filtered off again and dried in vacuo, yielding 4-(methoxymethyl)-N-phenyl-1-(2-phenylethyl)-4-piperidinamine dihydrochloride; mp. 221.4° C.

EXAMPLE XXI

To a stirred and gently refluxing solution of 43 parts of ethyl 4-(phenylamino)-1-(2-phenylethyl)-4-piperidinecarboxylate in 288 parts of dry benzene is added dropwise a solution of 33.9 parts of sodium dihydro-bis(2-methoxyethoxy)aluminate 70% in 72 parts of dry benzene without heating. Upon completion, stirring is continued for 3 hours at reflux. The reaction mixture is allowed to cool to room temperature overnight and poured onto 1000 parts of ice-water. The resulting emulsion is decomposed by the addition of a concentrated sodium hydroxide solution. The organic layer is separated and filtered over hyflo. The filter-cake is washed thoroughly with benzene. The filtrate is dried, filtered and evaporated. The residue is crystallized from 385 parts of 2,2'-oxybispropane. The crude solid product is filtered off and recrystallized from 2-propanol, yielding 4-(phenylamino)-1-(2-phenylethyl)-4-piperidinemethanol; mp. 96.7° C.

To a stirred solution of 15.5 parts of 4-(phenylamino)-1-(2-phenylethyl)-4-piperidinemethanol in 67.5 parts of benzene are added successively 112.5 parts of sodium hydroxide solution 60% and 0.1 parts of N,N,N-triethylbenzenemethanaminium chloride. Then there are added dropwise 6.3 parts of dimethyl sulfate at a temperature below 32° C and while stirring vigorously. The whole is stirred for 1 hour at room temperature. Another 6.4 parts of dimethyl sulfate are added in two separate portions while after each addition the mixture is stirred at room temperature for respectively 3 and 2 hours. The reaction mixture is poured onto water and the product is extracted with benzene. The extract is washed with water, dried, filtered and evaporated. The residue is purified by column-chromatography over silica gel using a mixture of trichloromethane and 5% of methanol as eluent. The pure fractions are collected and the eluent is evaporated. The residue is converted into the hydrochloride salt in 1,1'-oxybisethane and 2-propanol. The salt is filtered off and crystallized from ethanol, yielding 4-(methoxymethyl)-N-phenyl-1-(2-phenylethyl)-4-piperidinamine dihydrochloride; mp. 229.8° C.

EXAMPLE XXII

To a stirred solution of 24.83 parts of 4-(phenylamino)-1-(2-phenylethyl)-4-piperidinemethanol in 128 parts of hexamethylphosphoric triamide are added portionwise 2.2 parts of sodium hydride dispersion 78% at a temperature below 30° C. The whole is stirred at room temperature for 1h.20. Then there are added dropwise 9.11 parts of (chloromethyl)benzene at a temperature below 30° C. Upon completion, stirring is continued for 18 hours at room temperature. The reaction mixture is poured onto 400 parts of water and the product is extracted with benzene. The extract is washed four times with water, dried, filtered and evaporated. The residue is purified by column-chromatography over silica gel, using a mixture of trichloromethane and 5% of methanol as eluent. The pure fractions are collected and the eluent is evaporated. The residue is converted into the ethanedioate salt in 2-propanol. The salt is filtered off and crystallized from 20 parts of 2-propanol. It is filtered off again and dried, yielding N-phenyl-1-(2-phenylethyl)-4-(phenylmethoxymethyl)-4-piperidinamine ethanedioate; mp. 159.6° C.

EXAMPLE XXIII

A solution of 2.7 parts of (2-bromoethyl)benzene), 3.1 parts of 1-[4-(phenylamino)-4-piperidinyl]-1-propanone and 2.6 parts of N,N-diethylethanamine in 18 parts of N,N-dimethylacetamide is stirred for 4h. 30 at 80° C. The reaction mixture is poured onto 100 parts of water and the product is extracted with benzene. The extract is washed with water, dried, filtered and evaporated. The oily residue is purified by column-chromatography over silica gel using a mixture of trichloromethane and 5% of methanol as eluent. The pure fractions are collected and the eluent is evaporated. The oily residue is crystallized from 2,2'-oxybispropane, yielding 1-[4-(phenylamino)-1-(2-phenylethyl)-4-piperidinyl]-1-propanone; mp. 105.6° C.

EXAMPLE XXIV

A mixture of 100 parts of 4-[N-(3-methoxyphenyl)amino]-1-(phenylmethyl)-4-piperidinecarboxamide, 49.5 parts of potassium hydroxide and 974 parts of 1,2-ethanediol is stirred and refluxed for 24 hours. After cooling, the reaction mixture is poured onto 1500 parts of water and acidified with a concentrated hydrochloric acid solution. The whole is strongly alkalized with a sodium hydroxide solution and the layers are separated. The aqueous phase is concentrated, whereupon the product is separated as an oil. The supernatant aqueous phase is decanted and the residual oil is taken up in a sodium hydroxide solution. The precipitated product is filtered off and dissolved in water. The solution is acidified with acetic acid till pH = 6. The precipitated product is filtered off and warmed in ethanol. It is filtered off again, washed with ethanol and 2,2'-oxybispropane and dissolved in boiling N,N-dimethylformamide. The solution is filtered and the product is allowed to crystallized from the filtrate. It is filtered off, washed successively with N,N-dimethylformamide, water and ethanol, and dried, yielding 4-[N-(3-methoxyphenyl)amino]-1-(phenylmethyl)-4-piperidinecarboxylic acid; mp. 211.1° C.

To a stirred solution of 98 parts of 4-[N-(3-methoxyphenyl)-amino]-1-phenylmethyl)-4-piperidinecarboxylic acid in 660 parts of dry hexamethylphosphoric triamide are added portionwise 9.7 parts of sodium hydride dispersion 78%: exothermic reaction (temperature rises to 40° C). The solution is stirred for 2 hours and after cooling to room temperature, 45 parts of iodomethane are added dropwise. Upon completion, stirring is continued overnight at room temperature. 360 Parts of methylbenzene are added and the mixture is washed with water. The organic phase is separated, washed successively with a solution hydroxide solution 10% and water, dried, filtered and evaporated. The oily residue is converted into the ethanedioate salt in 2-propanol. The salt is filtered off and crystallized from ethanol, yielding methyl 4-[N-(3-methoxyphenyl)amino]-1-(phenylmethyl)-4-piperidinecarboxylate ethanedioate; mp. 182.5° C.

A mixture of 60 parts of methyl 4-[N-(3-methoxyphenyl)amino]-1-(phenylmethyl)-4-piperidinecarboxylate and 400 parts of ethanol is hydrogenated at normal pressure and at room temperature with 10 parts of palladium-on-charcoal catalyst 10%. After the calculated amount of hydrogen is taken up, the catalyst is filtered off and the filtrate is evaporated. The residue is purified by column-chromatography over silica gel using a mixture of trichloromethane and 10% of methanol, previously saturated with gaseous ammonia, as eluent. The pure fractions are collected and the eluent is evaporated, yielding methyl 4-[N-(3-methoxyphenyl)amino]-4-piperidinecarboxylate as an oily residue.

A mixture of 2.66 parts of 3-bromo-1-propene, 6.1 parts of methyl 4-[N-(3-methoxyphenyl)amino]-4-piperidinecarboxylate, 3.2 parts of sodium carbonate, 0.1 parts of potassium iodide and 100 parts of 4-methyl-2-pentanone is stirred and refluxed for 10 hours. The reaction mixture is cooled overnight to room temperature and poured onto water. The layers are separated and the organic phase is washed with water, dried, filtered and evaporated. The oily residue is purified by column-chromatography over silica gel using a mixture of trichloromethane and 6% of methanol as eluent. The pure fractions are collected and the eluent is evaporated, yielding methyl 4-[(3-methoxyphenyl)amino]-1-(2-propenyl)-4-piperidinecarboxylate as an oily residue.

EXAMPLE XXV

A mixture of 4.1 parts of (2-bromoethyl)benzene, 6.1 parts of methyl 4-[N-(3-methoxyphenyl)amino]-4-piperidinecarboxylate, 3.6 parts of N,N-diethylethanamine and 67.5 parts of N,N-dimethylacetamide is stirred and heated at 70°–80° C for 9 hours. The reaction mixture is allowed to cool to room temperature overnight and poured onto water. The product is extracted with methylbenzene. The extract is washed with water, dried, filtered and evaporated. The oily residue is purified by column-chromatography over silica gel using a mixture of trichloromethane and 6% of methanol as eluent. The pure fractions are collected and the eluent is evaporated. The oily residue is converted into the ethanedioate salt in 2-propanol. The salt is filtered off and crystallized from a mixture of 2-propanol and a small amount of ethanol, yielding, after drying, methyl 4-[N-(3-methoxyphenyl)amino]-1-(2-phenylethyl)-4-piperidinecarboxylate ethanedioate; mp. 184.7° C.

EXAMPLE XXVI

A mixture of 150 parts of 4-[N-(-4-fluorophenyl)-amino]-1-piperidinecarboxamide, 77.5 parts of potassium hydroxide and 660 parts of 1,2-ethanediol is stirred and refluxed for 28 hours. The reaction mixture is poured onto water and the whole is acidified with acetic acid till pH = ±6. The precipitated product is filtered off and crystallized from N,N-dimethylformamide. It is filtered off again and recrystallized from N,N-dimethylformamide, yielding, after drying, 4-[(4-fluorophenyl)amino]-1-(phenylmethyl)-4-piperidinecarboxylic acid; mp. 258.7° C.

70 Parts of 4-[(4-fluorophenyl)amino]-1-(phenylmethyl)-4-piperidinecarboxylic acid are dissolved in 450 parts of dry hexamethylphosphoric triamide at 120° C. This solution is cooled to room temperature and 6 parts of sodium hydride dispersion 78% are added portionwise at a temperature below 30° C. After stirring for 1.50 hours at room temperature, there are added dropwise 32.5 parts of iodomethane at a temperature below 15° C. Upon completion, stirring is continued for 28 hours at room temperature. The reaction mixture is poured onto 800 parts of water and the product is extracted with methylbenzene. The extract is washed successively with water, a 10% sodium hydroxide solution and again twice with water, dried, filtered and evaporated. The residue is purified by column-chromatography over silica gel using a mixture of trichloromethane and 5% of methanol as eluent. The pure fractions are collected and the eluent is evaporated. The oily residue is converted into the ethanedioate salt in 2-propanol. The salt is filtered off and crystallized from 2-propanol, yielding methyl 4-[(4-fluorophenyl)-amino]-1-(phenylmethyl)-4-piperidinecarboxylate ethanedioate; mp. 168.6° C.

A mixture of 53 parts of methyl 4-[(4-fluorophenyl)-amino]-1-(phenylmethyl)-4-piperidinecarboxylate and 400 parts of methanol is hydrogenated at normal pressure and at room temperature with 10 parts of palladium-charcoal catalyst 10%. After the calculated amount of hydrogen is taken up, the catalyst is filtered off and the filtrate is evaporated. The residue is purified by column-chromatography over silica gel using a mixture of trichloromethane and 15% of methanol, previously saturated with gaseous ammonia, as eluent. The pure fractions are collected and the eluent is evaporated. The oily residue solidifies on scratching in hexane. The product is filtered off and dried, yielding methyl 4-[(4-fluorophenyl)amino]-4-piperidinecarboxylate; mp. 83.7° C.

A mixture of 5.5 parts of (2-bromoethyl)benzene, 6.33 parts of methyl 4-[(4-fluorophenyl)amino]-4-piperidinecarboxylate, 3 parts of N,N-diethylethanamine and 45 parts of N,N-dimethylacetamide is stirred and heated for 20 hours at 70°–80° C. The reaction mixture is poured onto 600 parts of water and the product is extracted with 1,1'-oxybisethane. The extract is dried, filtered and evaporated. The oily residue is purified by column-chromatography over silica gel using a mixture of trichloromethane and 5% of methanol as eluent. The pure fractions are collected and the eluent is evaporated. The oily residue is converted into the ethanedioate salt in 2-propanol. The salt is filtered off and crystallized from 4-methyl-2-pentanone, yielding, after drying, methyl 4-[(4-fluoro-phenyl)amino]-1-(2-phenylethyl)-4-piperidinecarboxylate ethanedioate; mp. 204.3° C.

EXAMPLE XXVII

A mixture of 150 parts of 1-benzyl-4-carbamoyl-4-N-(4-methoxy-anilino)-piperidine, 74 parts of potassium hydroxide and 660 parts of 1,2-ethanediol is stirred and refluxed for 28 hours. The reaction mixture is poured onto 600 parts of water and the whole is adjusted to pH = ±6 with acetic acid. The precipitated product is filtered off and crystallized from N,N-dimethylformamide. It is filtered off again, stirred in 2-propanone, filtered off and recrystallized from N,N-dimethylformamide, yielding, after drying, 4-[(4-methoxyphenyl)amino]-1-(phenylmethyl)-4-piperidinecarboxylic acid; mp. 250° C.

55 Parts of 4-[(4-methoxyphenyl)amino]-1-(phenylmethyl)-4-piperidinecarboxylic acid are dissolved in 400 parts of dry hexamethylphosphoric triamide at 95° C. The solution is cooled to 15° C and 4.8 parts of sodium hydride dispersion 78% are added. After stirring for 2 hours at room temperature, 26.5 parts of iodomethane are added dropwise at a temperature below 20° C. Upon completion, stirring is continued for 24 hours at room temperature. The reaction mixture is poured onto 600 parts of water and the product is extracted with methylbenzene. The extract is washed once with a sodium hydroxide solution 10% and twice with water, dried, filtered and evaporated. The residue is converted into the ethanedioate salt in 2-propanol. The salt is filtered off and crystallized from 2-propanol, yielding methyl 4-[(4-methoxyphenyl)amino]-1-(phenylmethyl)-4-piperidinecarboxylate ethanedioate; mp. 177°–185° C.

A mixture of 22 parts of methyl 4-[(4-methoxy-phenyl)amino]-1-(phenylmethyl)-4-piperidinecarboxylate and 240 parts of methanol is hydrogenated at normal pressure and at room temperature with 5 parts of palladium-on-charcoal catalyst 10%. After the calculated amount of hydrogen is taken up, the catalyst is filtered off and the filtrate is evaporated. The oily residue is purified by column-chromatography over silica gel using a mixture of trichloromethane and 15% of methanol, previously saturated with gaseous ammonia, as eluent. The pure fractions are collected and the eluent is evaporated. The oily residue is dissolved in 1,1'-oxybisethane and the solution is treated with activated charcoal. The latter is filtered off and the filtrate is evaporated. The oily residue is converted into the hydrochloride salt in 1,1'-oxybisethane and 2-propanol. The salt is precipitated as an oil. The supernatant phase is decanted and the residual oil solidifies on triturating in 1,1'-oxybisethane. The product is filtered off and crystallized twice from a mixture of 2-propanol and a small amount of methanol, yielding, after drying, methyl 4-[(4-methoxyphenyl)amino]-4-piperidinecarboxylate dihydrochloride; mp. 183.7° C.

A mixture of 6.8 parts of (2-bromoethyl)benzene, 9 parts of methyl 4-[(4-methoxyphenyl)amino]-4-piperidinecarboxylate, 6.3 parts of N,N-diethylethanamine and 90 parts of N,N-dimethylacetamide is stirred for 5 hours at 70°–80° C. The reaction mixture is cooled to room temperature and poured onto water. The product is extracted with benzene. The extract is washed with water, dried, filtered and evaporated. The oily residue is purified by column-chromatography over silica gel using a mixture of trichloromethane and 6% of methanol as eluent. The pure fractions are collected and the eluent is evaporated. The oily residue is converted into the hydrochloride salt in 1,1'-oxybisethane and 2-propanol. The salt precipitates as an oil. The supernatant phase is decanted and the residual oil solidifies on triturating in 1,1'-oxybisethane. The product is filtered off and crystallized from a mixture of 2-propanol and a small amount of methanol, yielding, after drying, methyl 4-[(4-methoxyphenyl)amino]-1-(2-phenylethyl)-4-piperidinecarboxylate dihydrochloride; mp. 186.9° C.

EXAMPLE XXVIII

A mixture of 100 parts of 1-(ethoxy-carbonyl)-4-carbamoyl)-4-(4-methyl-anilino)-piperidine, 184.8 parts of potassium hydroxide and 800 parts of 2-propanol is stirred and refluxed for 3 hours. After cooling, the reaction mixture is filtered and the filtrate is evaporated till almost dry. After the addition of 400 parts of water, evaporation is continued till the product is precipitated. After cooling, it is filtered off and suspended in trichloromethane. The undissolved product is filtered off (the filtrate is set aside) and crystallized twice from water. It is filtered off again, washed with 2,2'-oxybispropane and dried, yielding a first crude fraction of 20 parts. The trichloromethanefiltrate (see above) is washed with water, dried, filtered and evaporated. The solid residue is crystallized from acetonitrile, yielding a second fraction of 26 parts (crude product). The combined crude crops (respectively 20 and 26 parts) are recrystallized from water, yielding 4-[N-(4-methylphenyl)amino]-4-piperidinecarboxamide; mp. 180.4° C.

A mixture of 33.35 parts of (2-bromoethyl)benzene, 35 parts of 4-[N-(4-methylphenyl)amino]-4-piperidinecarboxamide, 20 parts of N,N-diethylethanamine and 225 parts of N,N-dimethylacetamide is stirred for 4 hours at 70°–80° C. The reaction mixture is poured onto water and the product is extracted with trichloromethane. The extract is washed with water, dried, filtered and evaporated. The oily residue is poured onto water, whereupon the product is precipitated. It is filtered off and suspended twice in water. The product is filtered off again, washed with 2,2'-oxybispropane and dried, yielding 4-[N-(4-methylphenyl)amino]-1-(2-phenylethyl)-4-piperidinecarboxamide; mp. 163.1° C.

A mixture of 40 parts of 4-[N-(4-methylphenyl)amino]-1-(2-phenylethyl)-4-piperidinecarboxamide, 27.5 parts of potassium hydroxide and 330 parts of 1,2-ethanediol is stirred and refluxed for 28 hours. The reaction mixture is allowed to cool to room temperature overnight and poured onto 600 parts of water. The whole is acidified with a hydrochloric acid solution. The oily undissolved product is filtered off and set aside. The filtrate is alkalized with a sodium hydroxide solution 60%. After cooling, the precipitated product is filtered off and suspended in water. After boiling the suspension, the product is precipitated as an oil and 150 parts of trichloromethane are added. The organic phase is separated and evaporated. The solid residue is suspended twice in 160 parts of 2-propanol. The product is filtered off and dried, yielding a first fraction of sodium 4-[N-(4-methylphenyl)amino]-1-(2-phenylethyl)-4-piperidinecarboxylate hemihydrate; mp.>300° C. The oily product (see above) is boiled in trichloromethane. The organic phase is separated and evaporated. The solid residue is suspended four times in 80 parts of 2-propanol. The product is filtered off and dried, yielding sodium 4-[N-(4-methylphenyl)amino]-1-(2-phenylethyl)-4-piperidinecarboxylate hemihydrate; mp.>300° C.

A mixture of 19 parts of sodium 4-[N-(4-methylphenyl)amino]-1-(2-phenylethyl)-4-piperidinecarboxylate and 200 parts of hexamethylphosphoric triamide is heated to 80° C for a while. After cooling, 12.3 parts of iodomethane are added dropwise at a temperature below 15° C. Upon completion, stirring is continued for 24 hours at room temperature. The reaction mixture is poured onto 600 parts of water and the product is extracted with trichloromethane. The extract is washed twice with water, dried, filtered and evaporated. The oily residue is poured onto 200 parts of water while stirring. The supernatant aqueous phase is decanted and the residual oil is dissolved in trichloromethane. The solution is washed with water, dried, filtered and evaporated. The residue is purified twice by column-chromatography over silica gel using a mixture of trichloromethane and 7% of methanol as eluent. The pure fractions are collected and the eluent is evaporated. The oily residue is suspended in 2,2'-oxybispropane. The product is filtered off and dried, yielding methyl 4-(4-methylphenylamino)-1-(2-phenylethyl)-4-piperidinecarboxylate; mp. 94.5° C.

EXAMPLE XXIX

A mixture of 100 parts of 4-[(4-methylphenyl)amino]-1-(phenylmethyl)-4-piperidinecarboxamide, 52.2 parts of potassium hydroxide and 638 parts of 1,2-ethanediol is stirred and refluxed for 25 hours. After cooling, 1200 parts of water are added and the whole is acidified with a concentrated hydrochloric acid solution. The acid aqueous phase is alkalized with a sodium hydroxide solution 60%: exothermic reaction. After cooling, the precipitated crude product is filtered off and dissolved in water. This solution is acidified with acetic acid (pH about 6.5) and the product is filtered off. It is crystallized from N,N-dimethylformamide, filtered off again, washed with 2-propanone and dried, yielding 4-[(4-methylphenyl)amino]-1-(phenylmethyl)-4-piperidinecarboxylic acid; mp. 270° C.

51 Parts of 4-[(4-methylphenyl)amino]-1-(phenylmethyl)-4-piperidinecarboxylic acid are dissolved in 260 parts of hexamethylphosphoric triamide at 90° C. The solution is cooled to 22° C and 5 parts of sodium hydride dispersion 78% are added portionwise (slightly exothermic reaction: temperature rises to 30° C). After stirring for 1.50 hours at room temperature, 24.5 parts of iodoethane are added dropwise (exothermic reaction: temperature rises to 35° C). Upon completion, stirring is continued for 21.30 hours at room temperature. The reaction mixture is poured onto 600 parts of water and the product is extracted with methylbenzene. The extract is washed twice with water, dried, filtered and evaporated. The residue is converted into the hydrochloride salt in 1,1'-oxybisethane. The salt is filtered off, washed with warm 2-propanone and crystallized from boiling anhydrous ethanol. It is filtered off again, washed with a small amount of 2-propanone and dried, yielding ethyl 4-[(4-methylphenyl)amino]-1-(phenylmethyl)-4-piperidinecarboxylate dihydrochloride; mp. 213.4° C.

A mixture of 37.5 parts of ethyl 4-[(4-methylphenyl)amino]-1-(phenylmethyl)-4-piperidinecarboxylate and 240 parts of ethanol is hydrogenated at normal pressure and at room temperature with 5 parts of palladium-on-charcoal catalyst 10%. After the calculated amount of hydrogen is taken up, the catalyst is filtered off and the filtrate is evaporated. The oily residue is converted into the ethanedioate salt in 2-propanone. The salt is filtered off and dried, yielding ethyl 4-[(4-methylphenyl)amino]-4-piperidinecarboxylate sesquiethanedioate; mp. 168.1° C.

A mixture of 5.55 parts of (2-bromoethyl)benzene, 7 parts of ethyl 4-[(4-methylphenyl)amino]-4-piperidinecarboxylate, 3.5 parts of N,N-diethylethanamine and 108 parts of N,N-dimethylacetamide is stirred and heated for 24.50 hours in an oil-bath at 70°–80° C. The reaction mixture is cooled and poured onto water. The organic phase is separated and extracted with methylbenzene. The extract is washed with water, dried, filtered and evaporated. The oily residue is converted into the hydrochloride salt in 2-propanone and 1,1'-oxybisethane. The salt is filtered off and crystallized from 2-propanone, yielding ethyl 4-[(4-methylphenyl)amino]-1-(2-phenylethyl)-4-piperidinecarboxylate dihydrochloride; mp. 187.6° C.

EXAMPLE XXX

A solution of 378.5 parts of 1-(phenylmethyl)-4-piperidinone and 362.5 parts of 3-(trifluoromethyl)benzenamine in 1500 parts of acetic acid is stirred for 1 hour at room temperature: exothermic reaction (temperature rises to 40° C). After cooling, there are added 262.7 parts of potassium cyanide and the whole is stirred for 4 days at room temperature. The reaction mixture is poured onto a mixture of crushed ice and ammonium hyroxide and the product is extracted with trichloromethane. The extract is washed with a diluted ammonium hydroxide solution, dried, filtered and evaporated. The residue is crystallized from a mixture of 2,2'-oxybispropane and petroleum-ether (2:1 by volume), yielding 1-(phenylmethyl)-4-{[3-(trifluoromethyl)phenyl]amino}-4-piperidinecarbonitrile; mp. 96° C.

To 1656 parts of concentrated sulfuric acid are added portionwise 249.5 parts of 1-(phenylmethyl)-4-{[3-trifluoromethyl)phenyl]amino}-4-piperidinecarbonitrile. Upon completion, stirring is continued overnight at room temperature. The reaction mixture is poured onto crushed ice and while cooling, the whole is alkalized with ammonium hydroxide. Upon stirring vigorously, the product precipitates. The supernatant aqueous phase is decanted and the residual solid product is dissolved in trichloromethane. The solution is shaken with ammonium hydroxide. The organic phase is washed with water, dried, filtered and evaporated. The solid residue is stirred in 2,2'-oxybispropane. The product is filtered off, washed with hexane and dried in vacuo, yielding 1-(phenylmethyl)-4-{[3-(trifluoromethyl)phenyl]amino}-4-piperidinecarboxamide; mp. 179.3° C.

To 792 parts of concentrated hydrochloric acid solution are added 100 parts of 1-(phenylmethyl)-4-{[3-(trifluoromethyl)phenyl]amino}-4-piperidinecarboxamide. The whole is heated to reflux temperature while stirring. 230 Parts of water are added followed by the addition of anti-foam. Stirring at reflux is continued for 3.50 h. After cooling to room temperature, the reaction mixture is poured into a vessel and 200 parts of water are added. The whole is strongly alkalized with sodium hydroxide while stirring vigorously: a precipitate is formed. The supernatant aqueous phase is decanted and the residual precipitate is dissolved in water. The resulting solution is cooled and acidified with acetic acid (pH = about 7), whereupon the product is precipitated. It is filtered off and boiled in N,N-dimethylformamide. After cooling, the product is filtered off again, washed successively with ethanol and 2,2'-oxybispropane and dried. The less pure fraction is crystallized from N,N-dimethylformamide. The pure product is filtered off, washed successively with ethanol and with N,N-dimethylformamide, and dried at 140° C, yielding 1-(phenylmethyl)-4-[3-(trifluoromethyl)phenylamino]-4-piperidinecarboxylic acid; mp. 264.3° C.

To a stirred solution of 78 parts of 1-(phenylmethyl)-4-[3-(trifluoromethyl)phenylamino]-4-piperidinecarboxylic acid in 470 parts of dry hexamethylphosphoric triamide are added portionwise 6.3 parts of sodium hydride dispersion 78% (slightly exothermic reaction). After stirring for one hour at room temperature, 29.3 parts of iodomethane are added dropwise. Upon completion, stirring is continued overnight at room temperature. Methylbenzene is added and the whole is washed with water. The organic phase is separated, washed with a sodium hydroxide solution 10% and with water, dried, filtered and evaporated. The oily residue is purified by column-chromatography over silica gel using a mixture of trichloromethane and 3% of methanol as eluent. The pure fractions are collected and the eluent is evaporated. The oily residue is converted into the hydrochloride salt in 1,1'-oxybisethane and 2-propanol. After stirring vigorously, the salt is filtered off and crystallized twice from 4-methyl-2-pentanone, yielding methyl 1-(phenylmethyl)-4-[3-(trifluoromethyl)phenylamino]-4-piperidinecarboxylate; mp. 120.4° C.

A mixture of 61.5 parts of methyl 1-(phenylmethyl)-4-[3-(trifluoromethyl)phenylamino]-4-piperidinecarboxylate and 400 parts of methanol is hydrogenated at normal pressure and at room temperature with 10 parts of palladium-on-charcoal catalyst 10%. After the calculated amount of hydrogen is taken up, the catalyst is filtered off and the filtrate is evaporated. The oily residue is heated in 2,2'-oxybispropane. After cooling, the solid product is filtered off, washed with 2,2'-oxybispropane and dissolved in 1,1'-oxybisethane. The solution is filtered and the filtrate is evaporated. The residue is cooled and triturated in hexane. The product is filtered off and dried, yielding methyl 4-[3-(trifluoromethyl]-4-piperidinecarboxylate; mp. 98.1° C.

A mixture of 4.1 parts of (2-bromoethyl)benzene, 6 parts of methyl 4-[3-(trifluoromethyl)phenylamino]-4-piperidinecarboxylate, 3.6 parts of N,N-diethylethanamine and 67.5 parts of N,N-dimethylacetamide is stirred and heated for 10 hours at 70°–80° C. The reaction mixture is cooled to room temperature and poured onto water. The product is extracted with methylbenzene. The extract is washed with water, dried, filtered and evaporated. The oily residue is purified by column-chromatography over silica gel using a mixture of trichloromethane and 6% of methanol as eluent. The pure fractions are collected and the eluent is evaporated. The oily residue is converted into the hydrochloride salt in 1,1'-oxybisethane and 2-propanol. The salt is filtered off and crystallized from 2-propanol at 0° C, yielding, after drying in vacuo at 110° C, methyl 1-(2-phenylethyl)-4-[3-(trifluoromethyl)phenylamino]-4-piperidinecarboxylate hydrochloride; mp. 210.1° C.

EXAMPLE XXXI

A mixture of 3.34 parts of (2-bromoethyl)benzene, 4.80 parts of propyl 4-[N-(1-oxopropyl)-N-phenylamino]-4-piperidinecarboxylate, 2.02 parts of N,N-diethylethanamine and 81 parts of N,N-dimethylacetamide is stirred and heated for 3 hours at 70°–80° C. The reaction mixture is cooled and poured onto 400 parts of water. The product is extracted with 1,1'-oxybisethane. The extract is washed with water, dried, filtered and evaporated. The oily residue is purified by column-chromatography over silica gel using a mixture of trichloromethane and 15% of methanol as eluent. The pure fractions are collected and the eluent is evaporated. The residue is converted into the ethanedioate salt in 2-propanone, yielding propyl 4-[N-(1-oxopropyl)-N-phenylamino]-1-(2-phenylethyl)-4-piperidinecarboxylate ethanedioate; mp. 215.7° C.

EXAMPLE XXXII

A mixture of 3.1 parts of (2-bromoethyl)benzene, 4.6 parts of ethyl 4-[N-(1-oxopropyl)-N-phenylamino]-4-piperidinecarboxylate, 2.7 parts of N,N-diethylethanamine and 67.5 parts of N,N-dimethylacetamide is stirred for 2 hours at 70° C. The reaction mixture is poured onto 600 parts of water, whereupon an oil is precipitated. The supernatant phase is decanted and discarded. The oily product is dissolved in 210 parts of 1,1'-oxybispropane. The solution is washed twice with water, dried, filtered and evaporated. The residue is converted into the ethanedioate salt in 2-propanol. The salt is filtered off and dried at 120° C, yielding ethyl 4-[N-(1-oxopropyl)-N-phenylamino]-1-(2-phenylethyl)-4-piperidinecarboxylate ethanedioate hemihydrate; mp. 197.1° C.

EXAMPLE XXXIII

A mixture of 3.06 parts of 1-iodopropane, 4.4 parts of methyl 4-[N-(1-oxopropyl)-N-phenylamino]-4-piperidinecarboxylate, 0.2 parts of potassium iodide, 1.75 parts of N,N-diethylethanamine and 63 parts of methylbenzene is stirred and refluxed for 3 hours. Another portion of 1 part of 1-iodopropane is added and stirring at reflux is continued for 3h.40. The reaction mixture is cooled and the precipitate is filtered off. The filtrate is washed with water, dried, filtered and evaporated. The oily residue is dissolved in 1,1'-oxybisethane. The solution is filtered and the filtrate is evaporated. The oily residue is converted into the ethanedioate salt in 2-propanone. The salt is filtered off and dried, yielding methyl 4-[N-(1-oxopropyl)-N-phenylamino]-1-propyl-4-piperidinecarboxylate ethanedioate; mp. 171.2° C.

EXAMPLE XXXIV

A mixture of 3.6 parts of 1-bromohexane, 5.8 parts of methyl 4-[N-(1-oxopropyl)-N-phenylamino]-4-piperidinecarboxylate, 3.5 parts of N,N-diethylethanamine, 0.1 parts of potassium iodide and 45 parts of anhydrous benzene is stirred and refluxed for 18 hours. The reaction mixture is cooled, washed twice with 50 parts of water, dried, filtered and evaporated. The residue is purified by column-chromatography over silica gel using a mixture of trichloromethane and 5% of methanol as eluent. The pure fractions are collected and the eluent is evaporated. The residue is dissolved in 70 parts of 2,2'-oxybispropane. The solution is stirred with activated charcoal. The latter is filtered off and the filtrate is evaporated. The oily residue is converted into the ethanedioate salt in 4-methyl-2-pentanone. The salt is filtered off and dried, yielding methyl 1-hexyl-4-[N-(1-oxopropyl)-N-phenylamino]-4-piperidinecarboxylate ethanedioate; mp. 263.9° C.

EXAMPLE XXXV

Following the procedure of Example XXXIV and using an equivalent amount of an appropriate bromoloweralkane in place of the 1-bromohexane used therein, the following compounds were prepared by carrying out the reaction in the indicated solvent.

Using dry benzene as a solvent were prepared:
methyl 4-[N-(1-oxopropyl)-N-phenylamino]-1-pentyl-4-piperidinecarboxylate ethanedioate; mp. 181.8° C.
methyl 1-butyl-4-[N-(1-oxopropyl)-N-phenylamino]-4-piperidinecarboxylate ethanedioate; mp. 186.7° C; and
methyl 1-(1-methylethyl)-4-[N-(1-oxopropyl)-N-phenylamino]-4-piperidinecarboxylate ethanedioate; mp. 163.2° C;

Using methylbenzene as a solvent were prepared:
methyl 1-octyl-4-[N-(1-oxopropyl)-N-phenylamino]-4-piperidinecarboxylate ethanedioate; mp. 143.7° C; and
methyl 1-heptyl-4-[N-(1-oxopropyl)-N-phenylamino]-4-piperidinecarboxylate ethanedioate; mp. 149.1° C;

EXAMPLE XXXVI

A mixture of 4.5 parts of (bromomethyl)cyclopropane, 4.8 parts of methyl 4-[N-(1-oxopropyl)-N-phenylamino]-4-piperidinecarboxylate, 5 parts of sodium carbonate, 0.3 parts of potassium iodide and 63 parts of methylbenzene is stirred and refluxed for 4h. The reaction mixture is cooled and filtered. The filtrate is washed with water, dried, filtered and evaporated. The oily residue is dissolved in petroleumether. The solution is filtered and the filtrate is evaporated. The oily residue is purified by column-chromatography over silica gel using a mixture of trichloromethane and 10% of methanol as eluent. The pure fractions are collected and the eluent is evaporated. The residue is converted into the ethanedioate salt in 2-propanone. The salt is filtered off and dried, yielding methyl 1-(cyclopropylmethyl)-4-[N-(1-oxopropyl)-N-phenylamino]-4-piperidinecarboxylate ethanedioate; mp. 171.4° C.

EXAMPLE XXXVII

A mixture of 3.5 parts of 1-chloro-4-(2-chloroethyl)benzene, 4.4 parts of methyl 4-[N-(1-oxopropyl)-N-phenylamino]-4-piperidinecarboxylate, 2.1 parts of N,N-diethylethanamine and 63 parts of N,N-dimethylformamide is stirred and heated at 70°–80° C for 8 hours. The reaction mixture is cooled and methylbenzene is added. The whole is filtered and the filtrate is evaporated in vacuo. Water is added to the residue and the product is extracted with trichloromethane. The extract is washed successively with water, a sodium bicarbonate solution and again with water, dried, filtered and evaporated. The residue is purified by column-chromatography over silica gel using a mixture of trichloromethane and 10% of methanol as eluent. The pure fractions are collected and the eluent is evaporated. The residue is converted into the ethanedioate salt in 2-propanone, yielding methyl 1-[2-(4-chlorophenyl)ethyl]-4-[N-(1-oxopropyl)-N-phenylamino]-4-piperidinecarboxylate ethanedioate; mp. 200.5° C.

EXAMPLE XXXVIII

Following the procedure of Example XXXVII and using an equivalent amount of an appropriately substituted (2-chloroethyl)benzene in place of the 1-chloro-4-(2-chloroethyl)benzene used therein, the following compounds were prepared after forming an acid addition salt with an appropriate acid:

methyl 1-[2-(3-methoxyphenyl)ethyl]-4-[N-(1-oxopropyl)-N-phenylamino]-4-piperidinecarboxylate ethanedioate; mp. 169.8° C;

methyl 1-[2-(2-methoxyphenyl)ethyl]-4-[N-(1-oxopropyl)-N-phenylamino]-4-piperidinecarboxylate ethanedioate; mp. 179.2° C;

methyl 4-[N-(1-oxopropyl)-N-phenylamino]-1-{2-[3-(trifluoromethyl)phenyl]ethyl}-4-piperidinecarboxylate ethanedioate; mp. 177.6° C;

methyl 1-[2-(2-methylphenyl)ethyl]-4-[N-(1-oxopropyl)-N-phenylamino]-4-piperidinecarboxylate ethanedioate; mp. 202.9° C;

methyl 1-[2-(3-methylphenyl)ethyl]-4-[N-(1-oxopropyl)-N-phenylamino]-4-piperidinecarboxylate ethanedioate; mp. 184.9° C;

methyl 1-[2-(4-methoxyphenyl)ethyl]-4-[N-(1-oxopropyl)-N-phenylamino]-4-piperidinecarboxylate ethanedioate; mp. 189.2° C; and methyl 1-[2-(4-methylphenyl)ethyl]-4-[N-(1-oxopropyl)-N-phenylamino]-4-piperidinecarboxylate hydrochloride; mp. 202.4° C.

EXAMPLE XXXIX

To a stirred and refluxing mixture of 3 parts of 4-N-(N-acetyl-anilino)-4-(ethoxy-carbonyl)-piperidine, 1.6 parts of sodium carbonate, a few crystals of potassium iodide in 160 parts of 4-methyl-2-pentanone is added dropwise a solution of 2.1 parts of 1-chloro-2-phenylethane in 16 parts of 4-methyl-2-pentanone. After the addition is complete, the whole is stirred and refluxed for 72 hours. After cooling, 100 parts of water are added. The organic layer is separated, dried over magnesium sulfate, filtered and evaporated. The oily residue is dissolved in 20 parts of 2-propanol. This solution is added to a boiling solution of 0.9 parts of oxalic acid dihydrate in 20 parts of 2-propanol and the whole is boiled for 5 minutes. After cooling to room temperature, 4-N-(N-acetylanilino)-4-(ethoxy-carbonyl)-1-(2-phenyl-ethyl)-piperidine oxalate is obtained; mp. 198°–199° C.

EXAMPLE XL

A mixture of 2 parts of 1,3-dihydro-2H-inden-2-one, 4.4 parts of methyl 4-[N-(1-oxopropyl)-N-phenylamino]-4-piperidinecarboxylate and 80 parts of methanol is hydrogenated at normal pressure and at room temperature with 2 parts of palladium-on-charcoal catalyst 10%. After the calculated amount of hydrogen is taken up, the catalyst is filtered off and the filtrate is evaporated. The residue is purified by column-chromatography over silica gel using a mixture of trichloromethane and 5% of methanol as eluent. The pure fractions are collected and the eluent is evaporated. The residue is dissolved in 2,2'-oxybispropane. The solution is stirred with activated charcoal. The latter is filtered off and the filtrate is evaporated. The residue is converted into the ethanedioate salt in 4-methyl-2-pentanone. The salt is filtered off and crystallized from 2-propanol, yielding methyl 1-(2,3-dihydro-1H-inden-2-yl)-4-[N-(1-oxopropyl)-N-phenylamino]-4-piperidinecarboxylate ethanedioate 2-propanolate; mp. 206° C.

EXAMPLE XLI

A mixture of 4.3 parts of 4-phenyl-1-cyclohexanone, 4.3 parts of methyl 4-[N-(1-oxopropyl)-N-phenylamino]-4-piperidinecarboxylate and 80 parts of methanol is hydrogenated at normal pressure and at room temperature with 2 parts of palladium-on-charcoal catalyst 10%. After the calculated amount of hydrogen is taken up, the catalyst is filtered off. The filtrate is evaporated. The oily residue is purified by column-chromatography over silica gel using a mixture of trichloromethane and 7% of methanol as eluent. The pure fractions are collected and the eluent is evaporated. The oily residue is converted into the ethanedioate salt in 2-propanol. After cooling to −20° C, the salt is filtered off and dried, yielding methyl 4-[N-(1-oxopropyl)-N-phenylamino]-1-(4-phenylcyclohexyl)-4-piperidinecarboxylate ethanedioate; mp. 149.2° C.

EXAMPLE XLII

A mixture of 3.6 parts of N-(2-bromoethyl)benzenamine hydrobromide, 2.9 parts of methyl 4-[N-(1-oxopropyl)-N-phenylamino]-4-piperidinecarboxylate, 3 parts of N,N-diethylethanamine and 18 parts of N,N-dimethylacetamide is stirred for 4 hours at 70°–80° C. The reaction mixture is allowed to cool to room temperature, poured onto water and the product is extracted with 1,1'-oxybisethane. The extract is washed with water, dried, filtered and evaporated. The residue is purified by column-chromatography over silica gel using a mixture of trichloromethane and 5% of methanol as eluent. The pure fractions are collected and the eluent is evaporated. The residue is converted into the ethanedioate salt in 2-propanol. The salt is filtered off and suspended in 4-methyl-2-pentanone. The product is filtered off and dried, yielding methyl 4-[N-(1-oxopropyl)-N-phenylamino]-1-[2-(phenylamino)ethyl]-4-piperidinecarboxylate ethanedioate; mp. 189.1° C.

EXAMPLE XLIII

By repeating the procedure of Example XLII and using an equivalent amount of an appropriate bromide in place of the N-(2-bromoethyl)benzamine hydrobromide used therein, the following compounds of formula (I) were obtained:

methyl 4-[N-(1-oxopropyl)-N-phenylamino]-1-(3-phenylpropyl)-4-piperidinecarboxylate ethanedioate hemihydrate; mp. 156.9° C; and methyl 4-[N-(1-oxopropyl)-N-phenylamino]-1-(2-phenylethyl)-4-piperidinecarboxylate ethanedioate; mp. 189.5° C.

EXAMPLE XLIV

A mixture of 3.54 parts of α-methylphenethyl alcohol, methanesulfonate ester, 4.6 parts of ethyl 4-[N-(1-oxopropyl)-N-phenylamino]-4-piperidinecarboxylate, 3.97 parts of sodium carbonate and 160 parts of 4-methyl-2-pentanone is stirred and refluxed for 16 hours. The reaction mixture is cooled and filtered. The filtrate is washed twice with 200 parts of water, dried, filtered and evaporated. The residue is purified by column-chromatography over silica gel using a mixture of trichloromethane and 5% of methanol as eluent. The first fraction is collected and the eluent is evaporated.

The residue is converted into the ethanedioate salt in 2-propanol. The whole is evaporated and the residual salt is crystallized from 80 parts of 4-methyl-2-pentanone. The product is filtered off and dried in vacuo at 120° C, yielding ethyl 1-(1-methyl-2-phenylethyl)-4[N-(1-oxopropyl)-N-phenylamino]-4-piperidinecarboxylate ethanedioate; m.p. 201.8° C.

EXAMPLE XLV

Following the procedure of Example XLIV and using equivalent amounts of the appropriate starting materials, the following compounds are prepared:

ethyl 4-[N-(1-oxopropyl)-N-phenylamino]-1-[2-(2-thienyl)ethyl]-4-piperidinecarboxylate hydrochloride; mp. 210.3° C;

methyl 1-(1-methyl-2-phenylethyl)-4-[N-(1-oxopropyl)-N-phenylamino]-4-piperidinecarboxylate ethanedioate; m.p. 197° C;

methyl 4-[N-(1-oxopropyl)-N-phenylamino]-1-[2-(2-thienyl)ethyl]-4-piperidinecarboxylate ethanedioate; m.p. 201.6° C; and propyl 4-[N-(1-oxopropyl)-N-phenylamino]-1-[2-(2-thienyl)ethyl]-4-piperidinecarboxylate ethanedioate; m.p. 230.2° C.

EXAMPLE XLVI

A mixture of 1.3 parts of 2-phenyloxirane and 3 parts of ethyl 4-[N-(1-oxopropyl)-N-phenylamino]-4-piperidinecarboxylate is stirred for 18 hours at 100° C. The reaction mixture is cooled to room temperature. The oily product is purified by column-chromatography over silica gel using a mixture of trichloromethane and 5% of methanol as eluent. The pure fractions are collected and the eluent is evaporated. The oily residue is converted into the hydrochloride salt in 2,2'-oxybispropane and 2-propanol. The salt is filtered off and crystallized from 4-methyl-2-pentanone, yielding ethyl 1-(2-hydroxy-2-phenylethyl)-4-[N-(1-oxopropyl)-N-phenylamino]-4-piperidinecarboxylate hydrochloride; m.p. 201.9° C.

EXAMPLE XLVII

A mixture of 1.3 parts of 2-phenyloxirane and 2.9 parts of methyl 4-[N-(1-oxopropyl)-N-phenylamino]-4-piperidinecarboxylate is stirred and heated at 100° C for 18 hours. After cooling, the reaction mixture is dissolved in 22.5 parts of trichloromethane. The solution is purified by column-chromatography over silica gel using a mixture of trichloromethane and 5% of methanol as eluent. The pure fractions are collected and the eluent is evaporated. The residue is converted into the ethanedioate salt in 2-propanol. The salt is filtered off and crystallized from 2-propanol at 0° C. The product is filtered off and dried, yielding methyl 1-(2-hydroxy-2-phenylethyl)-4[N-(1-oxopropyl)-N-phenylamino]-4-piperidinecarboxylate ethanedioate; m.p. 194.2° C.

EXAMPLE XLVIII

A mixture of 2.04 parts of 2-phenyloxirane and 4.8 parts of propyl 4-[N-(1-oxopropyl)-N-phenylamino]-4-piperidinecarboxylate is stirred for 22 hours at 100° C. The reaction mixture is cooled to room temperature and the product is extracted with trichloromethane. The extract is dried, filtered and evaporated. The oily residue is purified by column-chromatography over silica gel using a mixture of trichloromethane and 5% of methanol as eluent. The pure fractions are collected and the eluent is evaporated. The oily residue is converted into the hydrochloride salt in 1,1'-oxybisethane. The salt is filtered off, washed with a small amount of 2-propanone and dried, yielding propyl 1-(2-hydroxy-2-phenylethyl)-4-[N-1-oxopropyl)-N-phenylamino]-4-piperidinecarboxylate hydrochloride; m.p. 203° C.

EXAMPLE IL

A mixture of 3.52 parts of cis-methyl 3-methyl-4-(phenylamino)-1-(2-phenylethyl)-4-piperidinecarboxylate and 15 parts of propanoic acid, anhydride is stirred and refluxed for 26h. 30 in an oil-bath at 190° C. The reaction mixture is allowed to cool to room temperature. After standing over week-end at room temperature, it is poured onto 150 parts of water and alkalized with a concentrated ammonium hydroxide solution. The product is extracted twice with 112 parts of trichloromethane. The combined extracts are washed three times with 50 parts of water, dried, filtered and evaporated. The residue is purified by column-chromatography over silica gel using a mixture of trichloromethane and 2% of methanol as eluent. The second fraction is collected and the eluent is evaporated. The residue is converted into the ethanedioate salt in 2-propanol and 2,2'-oxybispropane. The salt is filtered off, washed with 2-propanol and dried in vacuo at 100° C, yielding cis-methyl 3-methyl-4-[N-(1-oxopropyl)-N-phenylamino]-1-(2-phenylethyl)-4-piperidinecarboxylate ethanedioate; mp. 177° C.

EXAMPLE L

A mixture of 2.3 parts of trans-methyl 3-methyl-4-(phenylamino)-1-(2-phenylethyl)-4-piperidinecarboxylate and 10 parts of propanoic acid, anhydride is stirred and refluxed in an oil-bath at 180°–190° C for 24 hours. The reaction mixture is allowed to cool to room temperature, poured onto 100 parts of water and alkalized with a concentrated ammonium hydroxide solution. The product is extracted with trichloromethane. The extract is washed with water, dried, filtered and evaporated. The residue is purified twice by column-chromatography over silica gel using a mixture of trichloromethane and 2% of methanol as eluent. The pure fractions are collected and the eluent is evaporated. The oily residue is converted into the ethanedioate salt in 2-propanol and 2,2'-oxybispropane. The salt is filtered off and crystallized from 2-propanol, yielding trans-methyl 3-methyl-4-[N-(1-oxopropyl)-N-phenylamino]-1-(2-phenylethyl)-4-piperidinecarboxylate ethanedioate; m.p. 161.4° C.

EXAMPLE LI

A mixture of 5.1 parts of methyl 4-(phenylamino)-1-(2-phenylethyl)-4-piperidinecarboxylate and 11 parts of butanoic acid, anhydride is stirred and refluxed for 3 hours. The reaction mixture is cooled to room temperature, poured onto water and alkalized with ammonium hydroxide. The product is extracted with trichloromethane. The extract is washed with water, dried, filtered and evaporated. The oily residue is purified twice by column-chromatography over silica gel using a mixture of trichloromethane and 5% of methanol as eluent. The pure fractions are collected and the eluent is evaporated. The residue is converted into the hydrochloride salt in 2,2'-oxybispropane and 2-propanol. The salt is filtered off and crystallized twice: first from 2-propanone at −20° C and then from 2-propanol. The product is filtered off and dried, yielding methyl 4-[N-(1- oxobutyl)-N-phenylamino]-1-(2-phenylethyl)-4-piperidinecarboxylate hydrochloride hemihydrate; mp. 186.6° C.

EXAMPLE LII

Following the procedure of Example LI and using equivalent amounts of the appropriate starting materials the following compounds of formula (I) in acid addition salt form are prepared:

1-methylethyl 4-[N-(1-oxopropyl)-N-phenylamino]-1-(2-phenylethyl)-4-piperidinecarboxylate ethanedioate; mp. 186.8° C;

2-propenyl 4-[N-(1-oxopropyl)-N-phenylamino]-1-(2-phenylethyl)-4-piperidinecarboxylate ethanedioate; mp. 217.2° C;

phenylmethyl 4-[N-(1-oxopropyl)-N-phenylamino]-1-(2-phenylethyl)-4-piperidinecarboxylate hydrochloride; mp. 188.2° C;

ethyl 4-[N-(1-oxobutyl)-N-phenylamino]-1-(2-phenylethyl)-4-piperidinecarboxylate hydrochloride; mp. 176.4° C;

methyl 4-[N-(4-fluorophenyl)-N-(1-oxopropyl)-amino]-1-(2-phenylethyl)-4-piperidinecarboxylate ethanedioate; mp. 201.1° C;

methyl 4-[N-3-methoxyphenyl)-N-(1-oxopropyl)-amino]-1-(2-propenyl)-4-piperidinecarboxy-ethanedioate; mp. 162° C;

methyl 4-[N-4-methoxyphenyl)-N-(1-oxopropyl)-amino]-1-(2-phenylethyl)-4-piperidinecarboxylate ethanedioate; mp. 171.5° C;

methyl 4-[N-4-methoxyphenyl)-N-(1-oxopropyl)-amino]-1-(2-phenylethyl)-4-piperidinecarboxylate ethanedioate; mp. 189.3° C;

methyl 4-[N-4-methylphenyl)-N-(1-oxopropyl)-amino]-1-(2-phenylethyl)-4-piperidinecarboxylate ethanedioate; mp. 225.7° C;

methyl 4-[N-4-methylphenyl)-N-(1-oxopropyl)-amino]-1-(2-phenylethyl)-4-piperidinecarboxylate ethanedioate; mp. 235.8° C; and methyl 4-{N-(1-oxypropyl)-N-[3-(trifluoromethyl)-phenyl]amino}-1-(2-phenylethyl)-4-piperidinecarboxylate ethanedioate; mp. 196.7° C.

EXAMPLE LIII

A mixture of 3.52 parts of ethyl 4-(phenylamino)-1-(2-phenylethyl)-4-piperidinecarboxylate, 1.25 parts of cyclopropanecarbonyl chloride, 1.8 parts of N,N-diethylethanamine and 45 parts of methylbenzene is stirred and refluxed overnight. The reaction mixture is cooled to room temperature and washed with water. The organic phase is separated, dried, filtered and evaporated. The oily residue is dissolved in 2,2'-oxybispropane and the solution is stirred with activated charcoal. The latter is filtered off and the filtrate is evaporated. The oily residue is converted into the hydrochloride salt in 2,2'-oxybispropane and 2-propanol. The salt is filtered off and crystallized from 4-methyl-2-pentanone, yielding ethyl 4-[N-(cyclopropylcarbonyl)-N-phenylamino]-1-(2-phenylethyl)-4-piperidinecarboxylate hydrochloride; mp. 194.8° C.

EXAMPLE LIV

A mixture of 5.1 parts of methyl 4-(phenylamino)-1-(2-phenylethyl)-4-piperidinecarboxylate, 1.9 parts of cyclopropanecarbonyl chloride, 2.7 parts of N,N-diethylethanamine and 67.5 parts of methylbenzene is stirred and refluxed overnight. The reaction mixture is cooled to room temperature and poured onto water. The product is extracted with methylbenzene. The extract is washed with water, dried, filtered and evaporated. The oily residue is purified by column-chromatography over silica-gel using a mixture of trichloromethane and 3% of methanol as eluent. The pure fractions are collected and the eluent is evaporated. The oily residue is converted into the hydrochloride salt in 2,2'-oxybispropane and 2-propanol. The salt is filtered off and crystallized from 4-methyl-2-pentanone, yielding methyl 4-[N-(cyclopropylcarbonyl)-N-phenylamino]-1-(2-phenylethyl)-4-piperidinecarboxylate hydrochloride; mp. 197.8° C.

EXAMPLE LV

To a stirred mixture of 5.5 parts of N-[4-(methoxymethyl)-4-piperidinyl]-N-phenylpropanamide, 1.33 parts of sodium carbonate, 0.1 parts of potassium iodide and 45 parts of benzene are added 3 parts of 1-bromobutane. The whole is stirred and refluxed for 16 hours. The organic phase is separated, washed with water, dried, filtered and evaporated. The oily residue is purified by column-chromatography over silica gel using a mixture of trichloromethane and 10% of methanol as eluent. The pure fractions are collected and the eluent is evaporated. The oily residue is converted into the hydrochloride salt in 1,1'-oxybisethane and 2-propanol. The salt is filtered off and dried, yielding N-[1-butyl-4-(methoxymethyl)-4-piperidinyl]-N-phenylpropanamide hydrochloride hemihydrate; mp. 150.9° C.

EXAMPLE LVI

To a stirred mixture of 5.5 parts of N-[4-(methoxymethyl)-4-piperidinyl]-N-phenylpropanamide, 1.33 parts of sodium carbonate, 0.1 parts of potassium iodide and 45 parts of methylbenzene are added 4.3 parts of 1-bromooctane. The whole is stirred and refluxed for 9 hours. The reaction mixture is cooled to room temperature and the organic phase is separated. It is dried, filtered and evaporated. The oily residue is purified by column-chromatography over silica gel using a mixture of trichloromethane and 3% of methanol as eluent. The pure fractions are collected and the eluent is evaporated. The residue is converted into the ethanedioate salt in 2-propanol. The salt is filtered off and dried, yielding N-[4-(methoxymethyl)-1-octyl-4-piperidinyl]-N-phenylpropanamide ethanedioate; mp. 162.5° C.

EXAMPLE LVII

Following the procedure of Example LVI and using an equivalent amount of an appropriate bromoloweralkane or bromomethylcyclopropane in place of the 1-bromooctane used therein, the following compounds of formula (I) are obtained:

N-[1-heptyl-4-(methoxymethyl)-4-piperidinyl]-N-phenylpropanamide ethanedioate; mp. 168.1° C;

N-[1-hexyl-4-(methoxymethyl)-4-piperidinyl]-N-phenylpropanamide ethanedioate; mp. 177.6° C;

N-[4-(methoxymethyl)-1-pentyl-4-piperidinyl]-N-phenylpropanamide ethanedioate; mp. 173° C; and N-[1-(cyclopropylmethyl)-4-(methoxymethyl)-4-piperidinyl]-N-phenylpropanamide ethanedioate; mp. 155.2° C.

EXAMPLE LVIII

A mixture of 3.1 parts of 2-bromoethylbenzene, 4.1 parts of N-[4-(methoxymethyl)-4-piperidinyl]-N-phenylpropanamide, 0.1 parts of potassium iodide, 2.4 parts of sodium carbonate and 80 parts of 4-methyl-2-pentanone is stirred and refluxed for 48 hours. The reaction mixture is poured onto water and the whole is shaken thoroughly. The organic phase is separated, washed with water, dried, filtered and evaporated. The oily residue is purified by column-chromatography over silica gel using a mixture of trichloromethane and 5% of methanol as eluent. The pure fractions are collected and the eluent is evaporated. The oily residue solidifies on triturating in n-hexane. The product is filtered off and dried, yielding N-[4-(methoxymethyl)-1-(2-phenylethyl)-4-piperidinyl]-N-phenylpropanamide; mp. 85° C.

EXAMPLE LIX

Following the procedure of Example LVIII and using an equivalent amount of an appropriate bromide in place of the 2-bromoethylbenzene used therein, the following compounds of formula (I) are obtained in free base form or respectively in the form of acid addition salt after the reaction with an appropriate acid:

N-[4-(ethoxymethyl)-1-(2-phenylethyl)-4-piperidinyl]-N-phenylpropanamide; mp. 82.9° C;
N-[4-(methoxymethyl)-1-(3-phenylpropyl)-4-piperidinyl]-N-phenylpropanamide ethanedioate; mp. 203.7° C;
N-phenyl-N-[1-(2-phenylethyl)-4-(propoxymethyl)-4-piperidinyl]-propanamide hydrochloride; mp. 172.9° C; and
N-[4-(methoxymethyl)-1-(2-propenyl)-4-piperidinyl]-N-phenylpropanamide hydrochloride; mp. 209.4° C.

EXAMPLE LX

To a stirred mixture of 5.5 parts of N-[4-(methoxymethyl)-4-piperidinyl]-N-phenylpropanamide, 1.33 parts of sodium carbonate and 45 parts of benzene are added 3.7 parts of 1-iodopropane and the whole is stirred and refluxed for 14 hours. The reaction mixture is cooled to room temperature, washed with water, dried, filtered and evaporated. The oily residue is purified by column-chromatography over silica-gel using a mixture of trichloromethane and 10% of methanol as eluent. The pure fractions are collected and the eluent is evaporated. The oily residue is converted into the hydrochloride salt in 1,1'-oxybisethane and 2-propanol. The salt is filtered off and crystallized from 4-methyl-2-pentanone. The product is filtered off and dried, yielding N-[4-(methoxymethyl)-1-propyl-4-piperidinyl]-N-phenylpropanamide hydrochloride; mp. 224.5° C.

EXAMPLE LXI

A mixture of 4.1 parts of N-[4-(methoxymethyl)-4-piperidinyl]-N-phenylpropanamide, 5.3 parts of sodium carbonate and 120 parts of 4-methyl-2-pentanone is stirred and refluxed with water-separator. Then there are added 4.1 parts of 2-thiopheneethanol, methanesulfonate ester and stirring at reflux is continued for 18 hours. The reaction mixture is cooled, washed twice with water and evaporated. The oily residue is purified by column-chromatography over silica gel, using a mixture of trichloromethane and 5% of methanol as eluent. The first fraction is collected and the eluent is evaporated. The oily residue is converted into the hydrochloride salt in 2,2'-oxybispropane. The free base is liberated again in the conventional manner. After extraction with 2,2'-oxybispropane, the latter is dried, filtered and evaporated. The oily residue solidifies on triturating in petroleum-ether. The solid product is filtered off and crystallized from petroleum-ether at −20° C, yielding, after drying, N-{4-(methoxymethyl)-1-[2-(2-thienyl)ethyl]-4-piperidinyl}-N-phenylpropanamide; mp. 98.6° C.

EXAMPLE LXII

A mixture of 3.54 parts of α-methylphenethyl alcohol, methanesulfonate ester, 4.1 parts of N-[4-(methoxymethyl)-4-piperidinyl]-N-phenylpropanamide, 3.97 parts of sodium carbonate and 160 parts of 4-methyl-2-pentanone is stirred and refluxed for 24 hours with water-separator. After cooling, water is added and the product is extracted with trichloromethane. The extract is washed with water, dried, filtered and evaporated. The residue is purified by column-chromatography over silica gel using a mixture of benzene and 10% of methanol as eluent. The pure fractions are collected and the eluent is evaporated. The residue is converted into the ethanediolate salt in 2-propanol. The salt is filtered off, washed with 2-propanol and dried, yielding N-[4-(methoxymethyl)-1-(1-methyl-2-phenylethyl)-4-piperidinyl]-N-phenylpropanamide ethanedioate; mp. 196.8° C.

EXAMPLE LXIII

A mixture of 3.7 parts of 1-(2-chloroethyl)-4-methoxybenzene, 5.5 parts of N-[4-(methoxymethyl)-4-piperidinyl]-N-phenylpropanamide, 0.1 parts of potassium iodide, 2.52 parts of N,N-diethylethanamine and 45 parts of N,N-dimethylacetamide is stirred for 24 hours at 70° C. The reaction mixture is cooled to room temperature and poured onto water. The product is extracted with benzene. The extract is washed with water, dried, filtered and evaporated. The oily residue is purified by column-chromatography over silica gel using a mixture of trichloromethane and 3% of methanol as eluent. The pure fractions are collected and the eluent is evaporated. The oily residue is converted into the ethanedioate salt in 2-propanol. The salt is filtered off and dried in vacuo, yielding N-{4-(methoxymethyl)-1-[2-(4-methoxyphenyl)ethyl]-4-piperidinyl}-N-phenylpropanamide ethanedioate; mp. 185.3° C.

EXAMPLE LXIV

A mixture of 3.8 parts of 1-(2-chloroethyl)-4-fluorobenzene, 5.5 parts of N-[4-(methoxymethyl)-4-piperidinyl]-N-phenylpropanamide, 2.52 parts of N,N-diethylethanamine and 45 parts of N,N-dimethylacetamide is stirred and heated at 70° C for 24 hours. After cooling to room temperature, the reaction mixture is poured onto water and the product is extracted with benzene. The extract is washed with water, dried, filtered and evaporated. The oily residue is purified by column-chromatography matography over silica gel using a mixture of trichloromethane and 4% of methanol as eluent. The pure fractions are collected and the eluent is evaporated. The residue is converted into the ethanedioate salt in 2-propanol. The salt is filtered off and dried, yielding N-{1-[2-(4-fluorophenyl)ethyl]-4-(methoxymethyl)-4-piperidinyl}-N-phenylpropanamide ethanedioate; mp. 187.4° C.

EXAMPLE LXV

A mixture of 1-(2-chloroethyl)-4-methylbenzene, 5.5 parts of N-[4-(methoxymethyl)-4-piperidinyl]-N-phenylpropanamide, 3.6 parts of N,N-diethylethanamine and 35 parts of N,N-dimethylacetamide is stirred and heated at about 70° C for 26 hours. The reaction mixture is cooled to room temperature, poured onto water and the product is extracted with benzene. The extract is washed with water, dried, filtered and evaporated. The oily residue is purified by column-chromatography over silica gel using a mixture of trichloromethane and 5% of methanol as eluent. The pure fractions are collected and the eluent is evaporated. The oily residue is converted into the ethanedioate salt in 2-propanol. The salt is filtered off and dried, yielding N{4-(methoxymethyl)-1-[2-(4-methylphenyl)ethyl]-4-piperidinyl}-N-phenylpropanamide ethanedioate; mp. 189.9° C.

EXAMPLE LXVI

A mixture of 3.6 parts of 2-bromo-1-phenyl-1-propanone, 4.1 parts of N-[4-(methoxymethyl)-4-piperidinyl]-N-phenylpropanamide, 3.5 parts of N-(1-methylethyl)-2-propanamine and 80 parts of 4-methyl-2-pentanone is stirred and refluxed for 16 hours. The reaction mixture is cooled to room temperature and the precipitate is filtered off. The filtrate is evaporated. The oily residue is purified by column-chromatography over silica gel, using a mixture of trichloromethane and 3% of methanol as eluent. The pure fractions are collected and the eluent is evaporated. The oily residue solidifies on triturating in petroleumether. The product is filtered off and crystallized from 2,2'-oxybispropane. It is filtered off again and dried, yielding N-[1-(1-benzoylethyl)-4-(methoxymethyl)-4-piperidinyl]-N-phenylpropanamide; mp. 123° C.

EXAMPLE LXVII

To a stirred solution of 13.2 parts of N-[1-(1-benzoylethyl)-4-(methoxymethyl)-4-piperidinyl]-N-phenylpropanamide in 164 parts of methanol are added portionwise 1.34 parts of sodium borohydride (slightly exothermic reaction). Upon completion, stirring is continued first for 2 hours at 35° C and further overnight at room temperature. The reaction mixture is evaporated. The residue is taken up in 50 parts of water and the whole is warmed for a while. After cooling, the product is extracted three times with 75 parts of trichloromethane. The combined extracts are washed with water, dried, filtered and evaporated. The oily residue is purified twice by column-chromatography over silica-gel using a mixture of trichloromethane and 3% of methanol as eluent. The pure fractions are collected and the eluent is evaporated. The oily residue is triturated in petroleumether. The product is filtered off, crystallized from 2,2'-oxybispropane and a drop of 4-methyl-2-pentanone, filtered off again and dried at 110° C, yielding N-[1-(2-hydroxy-1-methyl-2-phenylethyl)-4-(methoxymethyl)-4-piperidinyl]-N-phenylpropanamide; mp. 154.2° C.

EXAMPLE LXVIII

A mixture of 2 parts of 2-phenyloxirane and 4.1 parts of N-[4-(methoxymethyl)-4-piperidinyl]-N-phenylpropanamide is stirred and heated at 100° C for 18 hours. After cooling, to room temperature, the reaction mixture is purified by column-chromatography over silica gel using a mixture of trichloromethane and 5% of methanol as eluent. The pure fractions are collected and the eluent is evaporated. The oily residue is converted into the hydrochloride salt in 1,1'-oxybisethane and 2-propanol. The supernatant phase is decanted and the residual salt is crystallized from 2-propanone. The product is filtered off and dried in vacuo, yielding N-[1-(2-hydroxy-2-phenylethyl)-4-(methoxymethyl)-4-piperidinyl]-N-phenylpropanamide hydrochloride; mp. 223.7° C.

EXAMPLE LXIX

A mixture of 3 parts of 4-(methoxymethyl)-N-phenyl-1-(2-phenylethyl)-4-piperidinamine and 5 parts of butanoic acid, anhydride is stirred and refluxed for 8 hours. The reaction mixture is poured onto water and the whole is alkalized with ammonium hydroxide. The product is extracted with trichloromethane. The extract is washed with water, dried, filtered and evaporated. The oily residue is stirred in 1,1'-oxybisethane with activated charcoal. The latter is filtered off and the filtrate is evaporated. The residue is converted into the ethanedioate salt 2-propanol. The salt is filtered off and crystallized from 2-propanone, yielding 1.7 parts of N-[4-(methoxymethyl)-1-(2-phenylethyl)-4-piperidinyl]-N-phenylbutanamide ethanedioate; mp. 174.2° C.

EXAMPLE LXX

To a stirred mixture of 3.25 parts of 4-(methoxymethyl)-N-phenyl-1-(2-phenylethyl)-4-piperidinamine and 36 parts of dry methylbenzene is added a mixture of 1.25 parts of cyclopropanecarbonyl chloride and 9 parts of dry methylbenzene at room temperature. The whole is stirred and refluxed for 3 hours. The reaction mixture is filtered hot and upon cooling, the product is allowed to crystallize from the filtrate. It is filtered off, washed with 2,2'-oxybispropane and dried, yielding N-[4-(methoxymethyl)-1-(2-phenylethyl)-4-piperidinyl]-N-phenylcyclopropanecarboxamide hydrochloride; mp. 178.6° C.

EXAMPLE LXXI 24.4 parts of propanoic acid anhydride are added to 9.96 parts of N-phenyl-1-(2-phenylethyl)-4-(phenylmethoxymethyl)-4-piperidinamine. The whole is stirred for 6 hours at reflux temperature. The reaction mixture is allowed to cool overnight to room temperature, poured onto water and alkalized with ammonium hydroxide. The product is extracted with trichloromethane. The extract is washed with water, dried, filtered and evaporated. The residue is converted into the hydrochloride salt in 2,2'-oxybispropane and 2-propanol (activated charcoal). The salt is filtered off and crystallized from 20 parts of 2-propanone. The product is filtered off and dried, yielding N-phenyl-N-[1-(2-phenylethyl)-4-(phenylmethoxymethyl)-4-piperidinyl]propanamide hydrochloride; mp. 166° C.

EXAMPLE LXXII

A mixture of 5.9 parts of N-phenyl-N-[1-(2-phenylethyl)-4-(phenylmethoxymethyl)-4-piperidinyl]-propanamide hydrochloride and 120 parts of methanol is hydrogenated at normal pressure and at room temperature with 2 parts of palladium-on-charcoal catalyst 10%. After the calculated amount of hydrogen is taken up, the catalyst is filtered off and washed on the filter with methanol. The filtrate is evaporated. The oily residue solidifies on scratching. The solid product is crystallized from 20 parts of 2-propanone at room temperature. It is filtered off and recrystallized from 2-propanol at 0° C, yielding N-[4-(hydroxymethyl)-1-(2- phenylethyl)-4-piperidinyl]-N-phenylpropanamide hydrochloride; mp. 218.4° C.

EXAMPLE LXXIII

A mixture of 4.8 parts of 1-[4-(phenylamino)-1-(2-phenylethyl)-4-piperidinyl]ethanone and 15 parts of propanoic acid, anhydride is stirred for 5 hours at 180° C (oil-bath). Stirring is continued overnight, while meantime the mixture is allowed to reach room temperature. The reaction mixture is poured onto ice-water and the whole is alkalized with a concentrated ammonium hydroxide solution. The product is extracted with benzene. The extract is washed twice with water, dried, filtered and evaporated in vacuo. The residue is dissolved in 1,1'-oxybisethane and the solution is stirred with activated charcoal. The latter is filtered off and the filtrate is evaporated. The residue is converted into the ethanedioate salt in 2-propanol. The salt is filtered off and crystallized from 2-propanol, yielding N-[4-acetyl-1-(2-phenylethyl)-4-piperidinyl]-N-phenylpropanamide ethanedioate; mp. 196.8° C.

EXAMPLE LXXIV

Following the procedure of Example LXXIII and using equivalent amounts of the appropriate starting materials, the following compounds of formula (I) are obtained:

N-[4-(1-oxopentyl)-1-(2-phenylethyl)-4-piperidinyl]-N-phenylpropanamide ethanedioate; mp. 200.8° C;

N-{4-(1-oxopropyl)-1-[2-(2-thienyl)ethyl]-4-piperidinyl}-N-phenylpropanamide ethanedioate; mp. 206° C;

N-[4-acetyl-1-(2-phenylethyl)-4-piperidinyl]-N-phenylbutanamide ethanedioate; mp. 198.9° C;

N-[4-(1-oxopropyl)-1-(2-phenylethyl)-4-piperidinyl]-N-phenylpropanamide ethanedioate; mp. 215.6° C.

EXAMPLE LXXV

A mixture of 4 parts of 1-[4-(phenylamino)-1-(2-phenylethyl)-4-piperidinyl]-1-propanone, 1.35 parts of cyclopropanecarbonyl chloride, 1.47 parts of N,N-diethylethanamine and 45 parts of methylbenzene is stirred and refluxed overnight. After cooling to room temperature, the reaction mixture is poured onto water and the layers are separated. The organic phase is dried, filtered and evaporated. The oily residue is purified by column-chromatography over silica gel using a mixture of trichloromethane and 3% of methanol as eluent. The pure fractions are collected and the eluent is evaporated. The oily residue is converted into the ethanedioate salt in 2-propanol. The salt is filtered off and crystallized from 2-propanol, yielding, after drying, N-[4-(1-oxopropyl)-1-(2-phenylethyl)-4-piperidinyl]-N-phenylcyclopropanecarboxamide ethanedioate; mp. 219.6° C.

EXAMPLE LXXVI

A mixture of 4.83 parts of 1-[4-(phenylamino)-1-(2-phenylethyl)-4-piperidinyl]ethanone, 1.9 parts of cyclopropanecarbonyl chloride, 1.2 parts of N,N-diethylethanamine and 67.5 parts of methylbenzene is stirred and refluxed overnight. The reaction mixture is cooled to room temperature and washed with water. The organic phase is dried, filtered and evaporated. The oily residue is converted into the ethanedioate salt in 2-propanol. The salt is allowed to crystallize overnight at −20° C. It is filtered off and dried, yielding N-[4-acetyl-1-(2-phenylethyl)-4-piperidinyl]-N-phenylcyclopropanecarboxamide ethanedioate; mp. 206.8° C.

EXAMPLE LXXVII

A mixture of 8 parts of 4-(phenylamino)-1-(2-phenylethyl)-4-piperidinemethanol and 35 parts of propanoic acid anhydride is stirred and refluxed for 3 hours. After cooling, the reaction mixture is poured onto 300 parts of ice-water and the whole is alkalized with sodium hydroxide solution. The product is extracted with 1,1'-oxybisethane. The extract is washed with water, dried, filtered and evaporated. The residue is dissolved in 140 parts of 2,2'-oxybispropane and the solution is stirred with activated charcoal. The latter is filtered off and the filtrate is evaporated. The residue is converted into the ethanedioate salt in 2-propanone. The salt is filtered off and dried, yielding N-[4-(hydroxymethyl)-1-(2-phenylethyl)-4-piperidinyl]-N-phenylpropanamide propanoate ethanedioate; mp. 182° C.

EXAMPLE LXXVIII

A mixture of 13 parts of N-[4-(methoxymethyl)-4-piperidinyl]-N-phenylpropanamide, 26.5 parts of sodium carbonate and 280 parts of 4-methyl-2-pentanone is distilled azeotropically to dry. Then there are added 20.5 parts of 2-thiopheneethanol, methanesulfonate ester and the whole is stirred and refluxed for 12 hours. The reaction mixture is washed twice with water and the layers are separated. The organic phase is dried, filtered and evaporated. The oily residue is purified by column-chromatography over silica gel using a mixture of trichloromethane and 5% of methanol as eluent. The pure fractions are collected and the eluent is evaporated. The oily residue is converted into the citrate salt in 2-propanone. The salt is filtered off and dried, yielding N- 4-(methoxymethyl)-1-[2-(2-thienyl)ethyl]-4-piperidinyl -N-phenylpropanamide 2-hydroxy-1,2,3-propanetricarboxylate; mp. 130.8° C.

EXAMPLE LXXIX

A mixture of 6 parts of (2-bromoethyl)benzene, 8.7 parts of methyl 4-[N-(1-phenylamino]-4-piperidinecarboxylate, 5.4 parts of N,N-diethylethanamine and 96 parts of N,N-dimethylacetamide is stirred for 3 hours at 70°–80° C. The reaction mixture is poured onto 400 parts of water and the product is extracted with 1,1'-oxybisethane. The extract is washed twice with water, dried, filtered and evaporated. The oily residue is purified by column-chromatography over silica gel using a mixture of trichloromethane and 5% of methanol as eluent. The pure fractions are collected and the eluent is evaported. The oily residue is converted into the citrate salt in 2-propanol. The salt is filtered off and crystallized from 2-propanol, yielding methyl 4-[N-(1-oxopropyl)-N-phenylamino]-1-(2-phenylethyl)-4-piperidinecarboxylate 2-hydroxy-1,2,3-propanetricarboxylate; m.p. 152.° C.

EXAMPLE LXXX

A mixture of 22.3 parts of sodium carbonate and 560 parts of 4-methyl-2-pentanone is distilled azeotropically to dry for 5 minutes. Then there are added 19.3 parts of N-[4-(methoxymethyl)-4-piperidinyl]-N-phenylpropanamide and 22 parts of 2-thiopheneethanol 4-methylbenzenesulfonate. The whole is stirred and refluxed for 24 hours. The reaction mixture is cooled, filtered and the filtrate is evaporated. The residue is dissolved in 1,1'-oxybisethane and acidified with 2-propanol, previously saturated with gaseous hydrogen chloride. The formed hydrochloride salt is filtered off and the free base is liberated in the conventional manner with a sodium hydroxide solution. The product is extracted with 1,1'-oxybisethane. The extract is dried, filtered and evaporated: the residue solidifies on standing. The solid residue is converted into the citrate salt in 2-propanone and 1,1'-oxybisethane. The salt is filtered off and crystallized from 2-propanone, yielding N-{4-(methoxymethyl)-1-[2-(2-thienyl)ethyl]-4-piperidinyl}-N-phenylpropanamide 2-hydroxy-1,2,3-propanetricarboxylate; m.p. 136.3° C.

EXAMPLE LXXXI

A mixture of 33.8 parts of methyl 4-(phenylamino)-1-(2-phenylethyl)-4-piperidinecarboxylate and 100 parts of propanoic acid anhydride is stirred and refluxed for 6.50 hours. The reaction mixture is allowed to cool overnight to room temperature while stirring and poured onto ice-water. The product is extracted with methylbenzene. The extract is washed with water, dried, filtered and evaporated. The residue is purified twice by column-chromatography over silica gel using a mixture of trichloromethane and 5% of methanol as eluent.

The first fraction is collected and the eluent is evaporated. The residue is converted into the citrate salt in 2-propanol and 1,1'-oxybisethane. The oily salt is triturated in a mixture of 2-propanol and 1,1'-oxybisethane. The solid product is filtered off and crystallized first twice from 2-propanol and then twice from 2-propanone. It is filtered off again and dried in vacuo at 100° C., yielding a first fraction of methyl 4-[N-(1-oxopropyl)-N-phenyl-amino]-1-(2-phenylethyl)-4-piperidinecarboxylate 2-hydroxy-1,2,3-propanetricarboxylate; m.p. 151.9° C.

The second fraction is collected and the eluent is evaporated. The residue is converted into the citrate salt in 2-propanol. The salt is filtered off and crystallized first from 2-propanol and then from 2-propanone, yielding a second fraction of methyl 4-[N-(1-oxopropyl)-N-phenylamino]-1-(2-phenylethyl)-4-piperidinecarboxylate 2-hydroxy-1,2,3-propanetricarboxylate; m.p. 153.4° C.

EXAMPLE LXXXII

A. A warm solution of 1.76 parts of cis-methyl 3-methyl-4-(phenylamino)-1-(2-phenylethyl)-4-piperidinecarboxylate and 1.5 parts of L-(+)-N-[(4-methylphenyl)sulfonyl]glutamic acid in 16 parts of 2-propanone is allowed to crystallize while cooling to room temperature.

The precipitated product is sucked off (the filtrate is set aside), washed with water, dried and crystallized from methanol, yielding cis-(+)-methyl 3-methyl-4-(phenylamino)-1-(2-phenylethyl)-4-piperidinecarboxylate L-(+)-N-[(4-methylphenyl)sulfonyl]-glutamate; $[\alpha]_D^{25} = +29.52°$ (0.5% methanol). From this salt the free base is liberated with sodium hydroxide in water and extracted with trichloromethane. The extract is dried, filtered and evaporated, yielding 0.5 parts (57%) of cis-(+)-methyl 3-methyl-4-(phenylamino)-1-(2-phenylethyl)-4-piperidinecarboxylate; m.p. 112.5° C.; $[\alpha]_D^{25} = +14.3°$ ($c = 0.5$% methanol).

The filtrate (see above) is concentrated to dry. From the residual salt the free base is liberated with sodium hydroxide in water and extracted with trichloromethane. The extract is dried, filtered and evaporated. The residue is converted into the D-(−)-N-[(4-methylphenyl)sulfonyl]glutamate salt in 2-propanone. The salt is sucked off, washed with water, dried, filtered and crystallized from methanol, yielding cis-(−)-methyl 3-methyl-4-(phenylamino)-1-(2-phenylethyl)-4-piperidinecarboxylate D-(−)-N-[(4-methylphenyl)sulfonyl]glutamate; $[\alpha]_D^{25} = -28.83°$ (0.5% methanol). The free base is liberated with sodium hydroxide in water and extracted with trichloromethane. The extract is dried, filtered and evaporated. The residue is crystallized from a mixture of benzene and hexane, yielding 0.5 parts (57%) of cis-(−)-methyl 3-methyl-4-(phenylamino)-1-(2-phenylethyl)-4-piperidinecarboxylate; m.p. 112.5° C.; $[\alpha]_D^{25} = -13.6°$ ($c = 0.5$% methanol).

B. A mixture of 3 parts of cis-(−)-methyl 3-methyl-4-(phenylamino)-1-(2-phenylethyl)-4-piperidinecarboxylate and 10 parts of propanoic acid anhydride is stirred and refluxed for 30 hours. The reaction mixture is cooled and poured onto water. The whole is alkalized with ammonium hydroxide and the product is extracted with methylbenzene. The extract is washed with water, dried, filtered and evaporated. The residue is purified by column-chromatography over silica gel, using a mixture of trichloromethane and 2% of methanol as eluent. The pure fractions are collected and the eluent is evaporated. The residue is converted into the ethanedioate salt in 2-propanol and 2,2'-oxybispropane. The salt is filtered off and dried, yielding 0.7 parts (16.5%) of cis-(+)-methyl 3-methyl-4-[N-(1-oxopropyl)-N-phenylamino]-1-(2-phenylethyl)-4-piperidinecarboxylate ethanedioate; m.p. 177.2° C.; $[\alpha]_D^{25} = +40.4°$ (0.5% $CH_3OH$).

C. A mixture of 3 parts of cis-(+)-methyl 3-methyl-4-(phenylamino)-1-(2-phenylethyl)-4-piperidinecarboxylate and 10 parts of propanoic acid anhydride is stirred and refluxed for 48 hours. The reaction mixture is allowed to cool overnight to room temperature, poured onto water and alkalized with ammonium hydroxide. The product is extracted with methylbenzene. The extract is washed with water, dried, filtered and evaporated in vacuo. The residue is purified by column-chromatography over silica gel, using a mixture of trichloromethane and 2% of methanol as eluent. The pure fractions are collected and the eluent is evaporated. The oily residue is converted into the ethanedioate salt in 2-propanol and 2,2'-oxybispropane: a sticky salt is obtained. The supernatant phase is decanted and the residual salt is crystallized from 2-propanol; yielding 0.9 parts (21.3%) of cis-(−)-methyl 3-methyl-4-[N-(1-oxopropyl)-N-phenylamino]-1-(2-phenylethyl)-4-piperidinecarboxylate ethanedioate; m.p. 176° C; $[\alpha]_D^{25} = -40.3°$ (0.5% $CH_3OH$).

EXAMPLE LXXXIII

A mixture of 60.1 parts of ethyl 4-[(4-methylphenyl)amino]-1-(2-phenylethyl)-4-piperidinecarboxylate, 27.6 parts of potassium hydroxide and 150 parts of 1,2-ethanediol is stirred and refluxed for 3 hours. The reaction mixture is cooled to room temperature and poured onto water. The whole is neutralized with acetic acid. The precipitated product is filtered off and crystallized from N,N-dimethylformamide. The product is filtered off and dried in vacuo, yielding 43.9 parts (79.2%) of 4-[(4-methylphenyl)amino]-1-(2-phenylethyl)-4-piperidinecarboxylic acid; mp. 264.6° C.

To a stirred solution of 17.4 parts of lithium in 140 parts of dry 1,1'-oxybisethane is added dropwise a small amount of a solution of 193.7 parts of iodomethane in 210 parts of dry 1,1'-oxybisethane. After the reaction is started by heating, there are added 420 parts of dry 1,1'-oxybisethane. The remainder of the solution is added dropwise at reflux temperature. Stirring at reflux is continued for 45 minutes. Then there are added portionwise (quickly) 41.8 parts of 4-[(4-methylphenyl)amino]-1-(2-phenylethyl)-4-piperidinecarboxylic acid (exothermic reaction: reflux temperature is maintained). Upon completion, stirring at reflux is continued for 1 hour. The reaction mixture is cooled in an ice-bath and decomposed by the dropwise addition of 1000 parts of water. The organic layer is separated and discarded. The aqueous phase is extracted with 1,1'-oxybisethane. The extract is dried, filtered and evaporated. The solid residue is crystallized from 2,2'-oxybispropane. The product is filtered off and recrystallized from 2,2'-oxybispropane, yielding 26 parts (62.4%) of 1-{4-[(4-methyphenyl)-amino]-1-(2-phenylethyl)-4-piperidinyl} ethanone; mp. 133.7° C.

EXAMPLE LXXXIV 75.7 Parts of 4-[(4-fluorophenyl)amino]-1-(phenylmethyl)-4-piperidinecarboxylic acid are dissolved in 489 parts of dry hexamethylphosphoric triamide while heating at 100° C. After cooling to room temperature, 7.07 parts of sodium hydride dispersion 78% are added portionwise (exothermic reaction:temperature rises to 40° C). After stirring for 2 hours, there are added dropwise 25.2 parts of bromoethane. Upon completion, stirring is continued overnight at room temperature. Methylbenzene is added and the whole is poured onto water. The layers are separated and the aqueous phase is extracted with methylbenzene. The combined organic phases are washed with a sodium hydroxide solution 10% and with water, dried, filtered and evaporated. The oily residue is purified by column-chromatography over silica gel using a mixture of trichloromethane and 5% of methanol as eluent. The pure fractions are collected and the eluent is evaporated. The oily residue is converted into the hydrochloride salt in 1,1'-oxybisethane and 2-propanol. The salt is filtered off and crystallized from ethanol, yielding, after drying, 61.4 parts of ethyl 4-[(4-fluorophenyl)amino]-1-(phenylmethyl)-4-piperidinecarboxylate dihydrochloride; mp. 219.8° C.

A mixture of 65.8 parts of ethyl 4-[(4-fluorophenyl)amino]-1-(phenylmethyl)-4-piperidinecarboxylate and 400 parts of ethanol is hydrogenated at normal pressure and at room temperature with 10 parts of palladium-on-charcoal catalyst 10%. After the calculated amount of hydrogen is taken up, the catalyst is filtered off and the filtrate is evaporated. The oily residue is converted into the hydrochloride salt in 1,1'-oxybisethane and 2-propanol. The salt is filtered off and crystallized from 2-propanol, yielding, after drying, 30 parts of ethyl 4-[(4-fluorophenyl)amino]-4-piperidinecarboxylate dihydrochloride; mp. 187.8° C.

A mixture of 33.7 parts of (2-bromoethyl)benzene, 44 parts of ethyl 4-[(4-fluorophenyl)amino]-4-piperidinecarboxylate, 30 parts of N,N-diethylethanamine and 555 parts of N,N-dimethylacetamide is stirred for 18 hours at 70° C. The reaction mixture is cooled to room temperature and poured onto water. The product is extracted with methylbenzene. The extract is washed with water, dried, filtered and evaporated. The oily residue is purified by column-chromatography over silica gel using a mixture of trichloromethane and 5% of methanol as eluent. The pure fractions are collected and the eluent is evaporated. The oily residue is converted into the hydrochloride salt in 1,1'-oxybisethane and 2-propanol. The salt is filtered off and crystallized from 2-propanol, yielding, after drying, 57.2 parts of ethyl 4-[(4-fluorophenyl)amino]-1-(2-phenylethyl)-4-piperidinecarboxylate dihydrochloride; mp. 185.6° C.

EXAMPLE LXXXV

A mixture of 43 parts of ethyl 4-[(4-fluorophenyl)amino]-1-(2-phenylethyl)-4-piperidinecarboxylate, 19.5 parts of potassium hydroxide and 106.7 parts of 1,2-ethanediol is stirred and refluxed for 3 hours. The reaction mixture is cooled to room temperature and poured onto water. The whole is neutralized with acetic acid (pH=+7). The precipitated product is filtered off and crystallized from N,N-dimethylformamide, yielding, after drying in vacuo, 31.1 parts (78.3%) of 4-[(4-fluorophenyl)amino]-1-(2-phenylethyl)-4-piperidinecarboxylic acid; mp. >260° C.

To start the reaction, a small amount of a solution of 132 parts of iodomethane in 98 parts of dry 1,1'-oxybisethane is dropped to a stirred solution of 11.9 parts of lithium in 98 parts of dry 1,1'-oxybisethane and the whole is heated to reflux. After the addition of 329 parts of dry 1,1'-oxybisethane, the remainder of the solution is added dropwise at reflux temperature. Stirring at reflux is continued for 1.50 hours. Then there are added portionwise 29 parts of 4-[(4-fluorophenyl)amino]-1-(2-phenylethyl)-4-piperidinecarboxylic acid (a violent reaction occurs whereby reflux temperature is maintained). Upon completion, stirring is continued for 1 hour at reflux. The reaction mixture is cooled in an ice-bath and carefully decomposed with 700 parts of water. The organic phase is separated, washed with water, dried, filtered and evaporated. The oily residue is crystallized from 2,2'-oxybispropane, yielding, after drying in vacuo, 15.4 parts (53.4%) of 1-{4-[(4-fluorophenyl)amino]-1-(2-phenylethyl)-4-piperidinyl}ethanone; mp. 119.4° C.

EXAMPLE LXXXVI

A mixture of 32.5 parts of methyl 4-(phenylamino)-1-(phenylmethyl)-4-piperidinecarboxylate and 200 parts of methanol is hydrogenated at normal pressure and at room temperature with 5 parts of palladium-on-charcoal catalyst 10%. After the calculated amount of hydrogen is taken up, the catalyst is filtered off and the filtrate is evaporated. The oily residue solidifies on scratching in 2,2'-oxybispropane. The product is filtered off and dried in vacuo, yielding 20 parts (85%) of methyl 4-(phenylamino)-4-piperidinecarboxylate; mp. 139.1° C.

A mixture of 37 parts of 2-bromopropane, 47.2 parts of methyl 4-(phenylamino)-4-piperidinecarboxylate, 50 parts of sodium carbonate, 1 part of potassium iodide and 800 parts of 4-methyl-2-pentanone is stirred and refluxed for 24 hours. After cooling, water is added and the layers are separated. The organic phase is dried, filtered and evaporated. The residue is converted into the hydrochloride salt in 2,2'-oxybispropane and 2-propanol. The salt is filtered off and crystallized from a mixture of methanol and 2,2'-oxybispropane, yielding 50 parts (74%) of methyl 1-(1-methylethyl)-4-

(phenylamino)-4-piperidinecarboxylate dihydrochloride.hemihydrate; mp. 168.7° C.

EXAMPLE LXXXVII

A mixture of 18.5 parts of 2-bromopropane, 25 parts of ethyl 4-(phenylamino)-4-piperidinecarboxylate, 25 parts of sodium carbonate, 1 part of potassium iodide and 400 parts of 4-methyl-2-pentanone is stirred and refluxed for 60 hours. The reaction mixture is cooled and washed with water. The organic phase is separated, dried, filtered and evaporated. The residue is converted into the hydrochloride salt in 2,2'-oxybispropane and 2-propanol. The salt is filtered off and crystallized from a mixture of ethanol and 2,2'-oxybispropane, yielding 20.9 parts (55%) of ethyl 1-(1-methylethyl)-4-phenylamino)-4-piperidinecarboxylate. dihydrochloride. hydrate; mp. 148.6° C.

EXAMPLE LXXXVIII

A mixture of 10 parts of 2-bromopropane, 9 parts of 4-(methoxymethyl)-N-phenyl-4-piperidinamine, 4.9 parts of N,N-diethylethanamine and 72 parts of N,N-dimethylacetamide is stirred and refluxed for 10.25 hours. After cooling, the formed N,N-diethylethanamine hydrobromide is filtered off and the filtrate is diluted with water. The product is extracted with methylbenzene. The extract is washed thoroughly with water, dried, filtered and evaporated. The residue is purified by column-chromatography over silica gel using a mixture of trichloromethane and methanol (90:10) as eluent. The pure fractions are collected and the eluent is evaporated, yielding 5.7 parts (42.6%) of 4-(methoxymethyl)-1-(1-methylethyl)-N-phenyl-4-piperidinamine as an oily residue.

EXAMPLE LXXXIX

A mixture of 39.5 parts of methyl 4-[N-(3-methoxyphenyl)amino]-1-(2-phenylethyl)-4-piperidinecarboxylate ethanedioate, 18 parts of potassium hydroxide and 90 parts of 1,2-ethanediol is stirred and refluxed for 3 hours. The reaction mixture is cooled to room temperature, poured onto 200 parts of water and acidified with a concentrated hydrochloric acid solution. The whole is strongly alkalized with a sodium hydroxide solution and stirred vigorously for one hour. The precipitated product is filtered off, dissolved in water and the solution is neutralized with acetic acid. The product is filtered off and crystallized from N,N-dimethylformamide, yielding 27.4 parts (72.3%) of 4-[(3-methoxyphenyl)amino]-1-(2-phenylethyl)-4-piperidinecarboxylic acid; mp. 265.1° C.

To start the reaction, a small amount of a solution of 101.4 parts of iodomethane in 81 parts of dry 1,1'-oxybisethane is dropped to a stirred solution of 8.95 parts of lithium in 81 parts of dry 1,1'-oxybisethane. After the addition of 244 parts of dry 1,1'-oxybisethane, the remainder of the solution is added dropwise at reflux temperature. Stirring at reflux is continued for 1 hour. Then there are added portionwise 23 parts of 4-[(3-methoxyphenyl)amino]-1-(2-phenylethyl)-4-piperidinecarboxylic acid (a violent reaction occurs whereby reflux temperature is maintained). Upon completion, stirring at reflux is continued for 1 hour. The reaction mixture is decomposed by the dropwise addition (carefully) of water. The organic phase is separated, washed with water, dried, filtered and evaporated. The oily residue is purified twice by column-chromatography over silica gel using first a mixture of trichloromethane and 6% of methanol and then a mixture of trichloromethane and 4% of methanol is eluent. The pure fractions are collected and the eluent is evaporated. The oily residue is converted into the ethanedioate salt in 2-propanol. The salt is filtered off, dried and crystallized twice from methanol, yielding 3.08 parts (96.5%) of 1-{4-[(3-methoxyphenyl)amino]-1-(2-phenylethyl)-4-piperidinyl}ethanone ethanedioate; mp. 188° C.

EXAMPLE XC

To a stirred solution of 3.7 parts of (phenylmethyl) carbonochloridate and 2.1 parts of N,N-diethylethanamine in 75 parts of trichloromethane is added dropwise a solution of 4.6 parts of methyl 4-(phenylamino)-4-piperidinecarboxylate in 30 parts of trichloromethane (exothermic reaction: cooling with ice-water is necessary to keep the temperature below 25° C). Upon completion, stirring is continued for 5 hours at room temperature. The reaction mixture is washed twice with water, dried filtered and evaporated. The residue is purified by column-chromatography over silica gel using trichloromethane as eluent. The pure fractions are collected and the eluent is evaporated. The residue is crystallized from 2-propanol, yielding 4.2 parts of $O^4$-methyl $O^1$-(phenylmethyl) 4-(phenylamino)-1,4-piperidinedicarboxylate; mp. 105.8° C.

A mixture of 14.8 parts of $O^4$-methyl $O^1$-(phenylmethyl) 4-(phenylamino)-1,4-piperidinedicarboxylate and 203 parts of ethyl carbonochloridate is stirred and refluxed for 24 hours in an oil-bath at 110° C. The reaction mixture is evaporated and the residue is dissolved in trichloromethane. The solution is washed twice with water, dried, filtered and evaporated, yielding 16.2 parts of $O^4$-methyl $O^1$-(phenylmethyl) 4-[(ethoxycarbonyl)phenylamino]-1,4-piperidinedicarboxylate as a residue.

A solution of 16.2 parts of $O^4$-methyl $O^1$-(phenylmethyl) 4-[(ethoxycarbonyl)phenylamino]-1,4-piperidinedicarboxylate in 200 parts of methanol and 20 parts of methanol, previously saturated with ammonia is hydrogenated at normal pressure and at room temperature with 3 parts of palladium-on-charcoal catalyst 10%. After the calculated amount of hydrogen is taken up, the catalyst is filtered off and the filtrate is evaporated, yielding 11.7 parts of methyl 4-[(ethoxycarbonyl)phenylamino]-4-piperidinecarboxylate as an oily residue.

EXAMPLE XCI

A mixture of 2.06 parts of 3-bromo-1-propene, 4.6 parts of ethyl 4-[(1-oxopropyl)phenylamino]-4-piperidinecarboxylate, 2,4 parts of sodium carbonate, 0.1 parts of potassium iodide and 80 parts of 4-methyl-2-pentanone is stirred and refluxed for 5 hours. After cooling to room temperature, the reaction mixture is poured onto water. The organic phase is separated, washed with water, dried, filtered and evapoarated. The oily residue is purified by column-chromatography over silica gel using a mixture of trichloromethane and 5% of methanol as eluent. The pure fractions are collected and the eluent is evaorated. The oily residue is converted into the ethanedioate salt in 2-propanol. The salt is filtered off and crystallized from 8 parts of 2-propanol. The product is filtered off and dried, yielding 3.8 parts of ethyl 4-[(1-oxopropyl)phenylamino]-1-(2-propenyl)-4-piperidinecarboxylate ethanedioate; mp. 152.9° C.

EXAMPLE XCII

To a stirred mixture of 5.5 parts of N-[4-(methoxymethyl)-4-piperidinyl]-N-phenylpropanamide, 1.33 parts of sodium carbonate, 0.1 parts of potassium iodide and 45 parts of benzene are added 4.9 parts of 2-bromopropane. Stirring is continued for 19 hours at reflux. The reaction mixture is cooled to room temperature. The organic phase is separated, washed with water, dried, filtered and evaporated. The oily residue is purified by column-chromatography over silica gel using a mixture of trichloromethane and 10% of methanol as eluent. The pure fractions are collected and the eluent is evaporated. The residue is converted into the hydrochloride salt in 1,1'-oxybisethane and 2-propanol. The salt is filtered off and crystallized from 4-methyl-2-pentanone. The product is filtered off and dried in vacuo, yielding 1.9 parts of N-[4-(methoxymethyl)-1-(1-methylethyl)-4-piperidinyl]-N-phenylpropanamide hydrochloride; mp. 249.2° C.

EXAMPLE XCIII

A mixture of 11 parts of N-(2-bromoethyl)benzenamine hydrobromide, 8.3 parts of N-[4-(methoxymethyl)-4-piperidinyl]-N-phenylpropanamide, 9.1 parts of N,N-diethylethanamine and 54 parts of N,N-dimethylacetamide is stirred and heated for 2 hours at 70°-80° C. The reaction mixture is cooled to room temperature, poured onto water and the product is extracted with benzene. The extract is washed with water, dried, filtered and evaporated. The oily residue is purified twice by column-chromatography over silica gel using a mixture of trichloromethane and 6% of methanol as eluent. The pure fractions are collected and the eluent is evaporated. The oily residue is converted into the hydrochloride salt in 1,1'-oxybisethane and 2-propanol. The salt is filtered off and crystallized from 2-propanol. The product is filtered off and dried, yielding 5.3 parts of N-{4-(methoxymethyl)-1-[2-(phenylamino)ethyl]-4-piperidinyl}-N-phenylpropanamide dihydrochloride; mp. 192.4° C.

EXAMPLE XCIV

To a stirred and refluxing mixture of 9.5 parts of sodium carbonate and 240 parts of 4-methyl-2-pentanone are added 8.3 parts of N-[4-(methoxymethyl)-4-piperidinyl]-N-phenylpropanamide and 9.6 parts of [2-(2-furanyl)ethyl] 4-methylbenzenesulfonate (water-separator). The whole is stirred and refluxed for 21 hours. The reaction mixture is cooled to room temperature and poured onto water. The organic phase is separated, washed with water, dried, filtered and evaporated. The oily residue is purified by column-chromatography over silica gel using a mixture of trichloromethane and 7% of methanol as eluent. The pure fractions are collected and the eluent is evaporated. The residue is converted into the ethanedioate salt in 2-propanol. The salt is filtered off and crystallized from 2-propanol, yielding 5.4 parts (39.1%) of N-{1-[2-(2-furanyl)ethyl]-4-(methoxymethyl)-4-piperidinyl}-N-phenylpropanamide ethanedioate; mp. 178.6° C.

EXAMPLE XCV

A mixture of 6.4 parts of sodium carbonate and 120 parts of 4-methyl-2-pentanone is stirred and refluxed with water-separator. Then there are added 4.1 parts of N-[4-(methoxymethyl)-4-piperidinyl]-N-phenylpropanamide and 5.5 parts of [2-(1-naphthalenyl)ethyl]4-methylbenzenesulfonate and the whole is stirred and refluxed for 20 hours. The reaction mixture is cooled to room temperature and poured onto water. The organic phase is separated, washed with water, dried, filtered and evaporated. The oily residue is purified by column-chromatography over silica gel using a mixture of trichloromethane and 7% of methanol as eluent. The pure fractions are collected and the eluent is evaporated. The oily residue solidifies on triturating in hexane. The product is filtered off and crystallized from a small amount of 2,2'-oxybispropane, yielding 2.8 parts (43.4%) of N-{4-(methoxymethyl)-1-[2-(1-naphthalenyl)ethyl]-4-piperidinyl}-N-phenylpropanamide; mp. 109.8° C.

EXAMPLE XCVI

A mixture of 20 parts of 1-(2-bromoethyl)-4-nitrobenzene, 21.8 parts of N-[4-(methoxymethyl)-4-piperidinyl]-N-phenylpropanamide, 14.4 parts of N,N-diethylethanamine and 270 parts of N,N-dimethylacetamide is stirred and heated for 4.50 hours at 70° C. The reaction mixture is cooled to room temperature and poured onto water. The product is extracted with methylbenzene. The extract is washed with water, dried, filtered and evaporated. The oily residue is purified by column-chromatography over silica gel using a mixture of trichloromethane and 4% of methanol as eluent. The first fraction is collected and the eluent is evaporated, yielding a first fraction of 14 parts of N- 4-(methoxymethyl)-1-[2-(4-nitrophenyl)ethyl]-4-piperidinyl -N-phenylpropanamide; mp. 98.7° C The second fraction is collected and the eluent is evaporated. The residue is purified once more by column-chromatography over silica gel using a mixture of trichloromethane and 4% of methanol as eluent. The pure fraction is collected and the eluent is evaporated, yielding a second fraction of 2.8 parts of N-{4-(methoxymethyl)-1-[2-(4-nitrophenyl)ethyl]-4-piperidinyl}-N-phenylpropanamide; mp. 98.7° C.

EXAMPLE XCVII

A mixture of 6.4 parts of 2-(2-bromoethyl)pyridine hydrobromide, 5.5 parts of N-[4-(methoxymethyl)-4-piperidinyl]-N-phenylpropanamide, 6.1 parts of N,N-diethylethanamine and 45 parts of N,N-dimethylacetamide is stirred and heated for 6 hours at 70° C. The reaction mixture is cooled to room temperature and poured onto water. The product is extracted with methylbenzene. The extract is washed with water, dried, filtered and evaporated: the oily residue solidifies after cooling to room temperature. The residue is triturated in petroleumether. The product is filtered off and crystallized from 2,2'-oxybispropane, yielding, after drying, 3.7 parts (48.6%) of N-{N- 4-(methoxymethyl)-1-[2(2-pyridinyl)ethyl]-4-piperidinyl}-N-phenylpropanamide; mp. 93.9° C.

EXAMPLE XCVIII

A mixture of 5.5 parts of ethyl 4-[(4-fluorophenyl)amino]-1-(2-phenylethyl)-4-piperidinecarboxylate and 14 parts of propanoic acid anhydride is stirred and refluxed for 6 hours. The reaction mixture is cooled to room temperature and poured onto water. The whole is alkalized with ammonium hydroxide and the product is extracted with trichloromethane. The extract is washed with water, dried, filtered and evaporated. The oily residue is purified by column-chromatography over silica gel using a mixture of trichloromethane and 2.5% of methanol as eluent. The pure fractions are collected and the eluent is evaporated. The oily residue is converted into the hydrochloride salt in 1,1'-oxybisethane and 2-propanol. The salt is filtered off and crystallized from 4-methyl-2-pentanone, yielding, after drying, 3.3 parts (47.8%) of ethyl 4-[(4-fluorophenyl) (1-oxopropyl)amino]-1-(2-phenylethyl)-4-piperidinecarboxylate hydrochloride; mp. 75.2° C.

EXAMPLE IC

A mixture of 4 parts of N-{4-(methoxymethyl)-1-[2-(phenylamino)ethyl]-4-piperidinyl}-N-phenylpropanamide and 10 parts of propanoic acid anhydride is stirred and refluxed for 8 hours. The reaction mixture is allowed to cool to room temperature while stirring. The whole is poured onto ice-water and alkalized with ammonium hydroxide. The product is extracted with trichloromethane. The extract is washed with water, dried, filtered and evaporated. The oily residue is dissolved in 1,1'-oxybisethane and the solution is stirred with activated charcoal. The latter is filtered off and the filtrate is evaporated. The residue is purified by column-chromatography over silica gel using a mixture of benzene and 10% of ethanol as eluent. The pure fractions are collected and the eluent is evaporated. The oily residue is converted into the ethanedioate salt in 2-propanol. The salt is allowed to crystallize in an ice-box. It is filtered off and dried, yielding 0.6 parts of N-[4-(methoxymethyl)-1-{2-[(1-oxopropyl)-phenylamino]ethyl}-4-piperidinyl]-4-phenylpropanamide ethanedioate; mp. 161.8° C.

EXAMPLE C

To a stirred solution of 8.4 parts of N-[1-(2-hydroxy-2-phenylethyl)-4-(methoxymethyl)-4-piperidinyl]-N-phenylpropanamide in 52.5 parts of 1,1'-oxybisethane are added 2.15 parts of propanoyl chloride and 3.8 parts of N,N-diethylethanamine. The whole is stirred for 5 hours at reflux. The reaction mixture is cooled to room temperature, poured onto water and the layers are separated. The organic phase is washed with water, dried, filtered and evaporated. The oily residue is purified by column-chromatography over silica gel using a mixture of trichloromethane and 7% of methanol as eluent. The pure fractions are collected and the eluent is evaporated. The oily residue is converted into the ethanedioate salt in 2-propanol. The solvent is evaporated. The oily residue solidifies on triturating in boiling 4-methyl-2-pentanone. The salt is filtered off and crystallized from 2-propanol. The product is filtered off and dried, yielding 4.6 parts (36.8%) of [2-{4-(methoxymethyl)-4-[(1-oxopropyl)phenylamino]-1-piperidinyl}-1-phenylethyl] propanoate sesquiethanedioate; mp. 171.2° C.

EXAMPLE CI

A mixture of 14.8 parts of N-{4-(methoxymethyl)-1-[2-(4-nitrophenyl)ethyl]-4-piperidinyl}-N-phenylpropanamide and 200 parts of methanol is hydrogenated at normal pressure and at room temperature with 3 parts of Raney-nickel catalyst. After the calculated amount of hydrogen is taken up, the catalyst is filtered off and the filtrate is evaporated. The oily residue is purified by column-chromatography over silica gel using a mixture of trichloromethane and 5% of methanol as eluent. The pure fractions are collected and the eluent is evaporated. The oily residue is triturated in petroleumether. The product is filtered off and crystallized from a small amount of 2,2'-oxybispropane. It is filtered off and dried, yielding 8.23 parts of N-{1-[2-(4-aminophenyl)ethyl]-4-(methoxymethyl)-4-piperidinyl}-N-phenylpropanamide; mp. 106.2° C.

EXAMPLE CII

A mixture of 5 parts of 1-{4-[(4-methylphenyl)amino]-1-(2-phenylethyl)-4-piperidinyl} ethanone and 14 parts of propanoic acid anhydride is stirred and refluxed for 5 hours. The reaction mixture is cooled to room temperature, poured onto ice-water and alkalized with ammonium hydroxide. The product is extracted with trichloromethane. The extract is washed with water, dried, filtered and evaporated. The oily residue is purified by column-chromatography over silica gel using a mixture of trichloromethane and 6% of methanol as eluent. The pure fractions are collected and the eluent is evaporated. The oily residue solidifies on triturating in petroleum-ether. The product is filtered off, crystallized from 2,2'-oxybispropane, filtered off again and dried in vacuo, yielding 2.5 parts (42.5%) of N-[4-acetyl-1-(2-phenylethyl)-4-piperidinyl]-N-(4-methylphenyl)-propanamide; mp. 112.8° C.

EXAMPLE CIII

A mixture of 5.1 parts of 1-{4-[(4-fluorophenyl)amino]-1-(2-phenylethyl)-4-piperidinyl}ethanone and 14 parts of propanoic acid anhydride is stirred and refluxed for 6 hours. The reaction mixture is cooled to room temperature and poured onto ice-water. The whole is alkalized with ammonium hydroxide and the product is extracted with trichloromethane. The extract is washed with water, dried, filtered and evaporated. The residue is dissolved in 2,2'-oxybispropane and the solution is treated with activated charcoal. The latter is filtered off and the filtrate is evaporated. The oily residue is purified by column-chromatography over silica gel using a mixture of trichloromethane and 7% of methanol as eluent. The pure fractions are collected and the eluent is evaporated. The oily residue is crystallized from 2,2'-oxybispropane yielding, after drying in vacuo, 2.9 parts (48.8%) of N-[4-acetyl-1-(2-phenylethyl)-4-pipe ridinyl]-N-(4-fluorophenyl)-propanamide; mp. 136.1° C.

EXAMPLE CIV

A mixture of 7.73 parts of (2-bromoethyl)benzene, 11.7 parts of methyl 4-[(ethoxycarbonyl)phenylamino]-4-piperidinecarboxylate, 6.9 parts of N,N-diethylethanamine and 171 parts of N,N-dimethylacetamide is stirred for 3 hours at 70° C. The reaction mixture is cooled to room temperature and poured onto 600 parts of water. The product is extracted with 360 parts of benzene. The extract is washed three times with water, dried, filtered and evaporated. The residue is purified twice by column-chromatography over silica gel using first trichloromethane and then a mixture of trichloromethane and methanol (95:5) as eluent. The pure fractions are collected and the eluent is evaporated. The residue is converted into the ethanedioate salt in 2-propanol. The salt is filtered off and boiled in 2-propanol. The product is filtered off and dried in vacuo at 120° C, yielding 5 parts of methyl 4-[(ethoxycarbonyl)phenylamino]-1-(2-phenylethyl)-4-piperidinecarboxylate ethanedioate; mp. 206.8° C.

EXAMPLE CV

To 57 parts of ethyl carbonochloridate are added portionwise 4.2 parts of 1-{4-[(4-fluorophenyl)amino]-1-(2-phenylethyl)-4-piperidinyl}ethanone (exothermic reaction). Upon completion, stirring is continued for 8 hours at reflux temperature. The reaction mixture is evaporated at normal pressure and the residue is dissolved in trichloromethane. The solution is washed successively twice with a 2% sodium hydroxide solution and once with water, dried, filtered and evaporated. The residue is purified by column-chromatography over silica gel using a mixture of trichloromethane and methanol (95:5) as eluent. The pure fractions are collected and the eluent is evaporated. The oil residue is converted into the ethanedioate salt in 2-propanol. The salt is filtered off and boiled in 2-propanol. After cooling, the product is filtered off and dried, yielding 3.7 parts (59.87%) of ethyl N-[4-acetyl-1-(2-phenylethyl)-4-piperidinyl]N-(4-fluorophenyl)carbamate ethanedioate; mp, 206.3° C.

EXAMPLE CVI

To a stirred and cooled solution of 28.7 parts of 4-methoxymethyl)-N-phenyl-4-piperidinamine and 14.4 parts of N,N-diethylethanamine in 540 parts of trichloromethane is added dropwise a solution of 24.4 parts of (phenylmethyl) carbonochloridate in 225 parts of trichloromethane at a temperature below 12° C (slightly exothermic reaction). Upon completion, stirring is continued for 5 hours at room temperature. The reaction mixture is washed twice with water, dried, filtered and evaporated. The residue is purified by column-chromatography over silica gel using a mixture of trichloromethane and methanol (99:1) as eluent. The pure fractions are collected and the eluent is evaporated, yielding 38.4 parts (83.47%) of (phenylmethyl) 4-(methoxymethyl)-4-(phenylamino)-1-piperidinecarboxylate as a residue.

A mixture of 14.2 parts of (phenylmethyl) 4-(methoxymethyl)-4-(phenylamino)-1-piperidinecarboxylate and 170.2 parts of ethyl carbonochloridate is stirred and refluxed for 16 hours in an oil-bath at 110° C. The reaction mixture is evaporated and the residue is dissolved in 225 parts of trichloromethane. The solution is washed twice with water, dried, filtered and evaporated. The residue is dissolved in methylbenzene and the latter is evaporated again, yielding 14.2 parts (83.5%) of (phenylmethyl) 4-[(ethoxycarbonyl)phenylamino]-4-(methoxymethyl)-1-piperidinecarboxylate as a residue.

A solution of 14.2 parts of (phenylmethyl) 4-[(ethoxycarbonyl)phenylamino]-4-(methoxymethyl)-1-piperidinecarboxylate and 1.8 parts of ammonium hydroxide in 120 parts of methanol is hydrogenated at normal pressure and at room temperature with 4 parts of palladium-on-charcoal catalyst 10%. After the calculated amount of hydrogen is taken up, the catalyst is filtered off and the filtrate is evaporated. The residue is dissolved in 75 parts of trichloromethane. The solution is washed twice with water, dried, filtered and evaporated, yielding 7.9 parts (81.4%) of ethyl [4-(methoxymethyl)-4-piperidinyl]phenylcarbamate as a residue.

A mixture of 5.5 parts of (2-bromoethyl)benzene, 7.9 parts of ethyl [4-(methoxymethyl)-4-piperidinyl]phenylcarbamate, 4.8 parts of N,N-diethylethanamine and 122 parts of N,N-dimethylacetamide is stirred for 3.50 hours at 70° C. The reaction mixture is cooled and poured onto 500 parts of ice-water. The product is extracted with benzene. The extract is washed three times with water, dried, filtered and evaporated. The residue is purified by column-chromatography over silica gel using a mixture of trichloromethane and methanol (97:3) as eluent. The pure fractions are collected and the eluent is evaporated. The oily residue is converted into the ethanedioate salt in 2-propanol. The salt is filtered off and boiled in 40 parts of 2-propanol. After cooling, it is filtered off again and dried, yielding 4.8 parts (31%) of ethyl [4-(methoxymethyl)-1-(2-phenylethyl)-4-piperidinyl]phenylcarbamate ethanedioate; mp. 190.7° C.

EXAMPLE CVII

To 194 parts of 1,1'-oxybisethane are added 9.1 parts of lithium aluminium hydride while nitrogen gas is introduced. Then there is added dropwise, during a 2 hours-period, a solution of 14.9 parts of 1-methyl-1H-pyrrole-2-acetic acid in 105 parts of 1,1'-oxybisethane (exothermic reaction). Upon completion, stirring is continued for 8 hours at reflux temperature and for 8 hours at room temperature. The reaction mixture is cooled in an ice-salt bath and decomposed by successive dropwise additions of 9.5 parts of water, 8.5 parts of a sodium hydroxide solution 20% and again 33.3 parts of water. The precipitated product is filtered off and suspended in 1,1'-oxybisethane. The combined 1,1'-oxybisethane phases are dried, filtered and evaporated. The oily residue is purified by column-chromatography over silica gel using a mixture of trichloromethane and methanol (93:7) as eluent. The pure fractions are collected and the eluent is evaporated, yielding 9.5 parts (69%) of 1-methyl-1H-pyrrole-2-ethanol as a residue.

To a stirred and cooled (±5° C) mixture of 20.7 parts of 1-methyl-1H-pyrrole-2-ethanol and 200 parts of dry pyridine are added portionwise 35.9 parts of 4-methylbenzenesulfonyl chloride. Upon completion, stirring is continued for 6 hours at about 5° C.

The reaction mixture is allowed to stand overnight at 0° C and poured onto water. The product is extracted with benzene. The extract is washed successively with a 20% hydrochloric acid solution, water, a 10% sodium carbonate solution and with water, dried, filtered and evaporated, yielding 33.4 parts (76.8%) of 2-(1-methyl-1H-pyrrol-2-yl)ethyl 4-methylbenzenesulfonate as an oily residue.

A mixture of 33.4 parts of 2-(1-methyl-1H-pyrrol-2-yl)ethyl 4-methylbenzenesulfonate, 27.6 parts of N-[4-(methoxymethyl)-4-piperidinyl]-N-phenylpropanamide, 31.8 parts of sodium carbonate and 400 parts of 4-methyl-2-pentanone is stirred and refluxed for 2.50 hours with water-separator. The reaction mixture is cooled to room temperature and washed with water. The organic phase is dried, filtered and evaporated. The oily residue is dissolved in 2,2'-oxybispropane and treated with activated charcoal. The latter is filtered off and the filtrate is evaporated. The oily residue is purified by column-chromatography over silica gel using a mixture of trichloromethane and methanol (97:3) as eluent. The pure fractions are collected and the eluent is evaporated. The oily residue is crystallized from petroleumether. The product is filtered off and recrystallized from 2,2'-oxybispropane, yielding, after drying, 2.8 parts (7.9%) of N-{4-(methoxymethyl)-1-[2-(1-methyl-1H-pyrrol-2-yl)ethyl]-4-piperidinyl}-N-phenylpropanamide; mp. 82.5° C.

EXAMPLE CVIII

Following the procedure of Example CIV and using equivalent amounts of the appropriate starting materials, the following compounds are prepared:
- methyl 4-[(ethoxycarbonyl)phenylamino]-1-(2-thienylethyl)-4-piperidinecarboxylate;
- methyl 4-[(ethoxycarbonyl)phenylamino]-1-(1-methylethyl)-4-piperidinecarboxylate;
- methyl 1-(cyclopropylmethyl)-4-[(ethoxycarbonyl)-phenylamino]-4-piperidinecarboxylate;
- methyl 1-[2-(4-chlorophenyl)ethyl]-4-[(ethoxycarbonyl)phenylamino]-4-piperidinecarboxylate;
- methyl 4-[(ethoxycarbonyl)phenylamino]-1-[2-(3-methoxyphenyl)ethyl]-4-piperidinecarboxylate;
- methyl 4-[(ethoxycarbonyl)phenylamino]-1-{2-[3-(trifluoromethyl)-phenyl]ethyl}-4-piperidinecarboxylate;
- methyl 4-[(ethoxycarbonyl)phenylamino]-1-[2-(2-methylphenyl)ethyl]-4-piperidinecarboxylate;
- methyl 4-[(ethoxycarbonyl)phenylamino]-1-(3-phenylpropyl)-4-piperidinecarboxylate; and
- methyl 4-[(ethoxycarbonyl)phenylamino]-1-(1-methyl-2-phenylethyl)-4-piperidinecarboxylate.

EXAMPLE CIX

Following the procedure of Example CV and using equivalent amounts of the appropriate starting materials, the following compounds are obtained:
- ethyl 4-[(ethoxycarbonyl)phenylamino]-1-(2-phenylethyl)-4-piperidinecarboxylate;
- methyl 4-[(methoxycarbonyl)phenylamino]-1-(2-phenylethyl)-4-piperidinecarboxylate;
- 1-methylethyl 4-[(ethoxycarbonyl)phenylamino]-1-(2-phenylethyl)-4-piperidinecarboxylate;
- 2-propenyl 4-[(ethoxycarbonyl)phenylamino]-1-(2-phenylethyl)-4-piperidinecarboxylate;
- cis-methyl 4-[(ethoxycarbonyl)phenylamino]-3-methyl-1-(2-phenylethyl)-4-piperidinecarboxylate;
- ethyl N-[4-acetyl-1-(2-phenylethyl)-4-piperidinyl] N-phenylcarbamate;
- ethyl N-[4-pentanoyl-1-(2-phenylethyl)-4-piperidinyl] N-phenylcarbamate;
- ethyl N-phenyl N-{4-propanoyl-1-[2-(2-thienyl)ethyl]-4-piperidinyl}-carbamate; and
- methyl 4-[(ethoxycarbonyl) (4-methoxyphenyl)-amino]-1-(2-phenylethyl)-4-piperidinecarboxylate.

EXAMPLE CX

Following the procedure of Example CVII and using equivalent amounts of the appropriate starting materials, the following compounds are prepared:
- methyl 1-[2-(1-methyl-1H-pyrrol-2-yl)ethyl]-4-[(1-oxopropyl)phenylamino]-4-piperidinecarboxylate;
- ethyl 1-[2-(1-methyl-1H-pyrrol-2-yl)ethyl]-4-[(1-oxopropyl)phenylamino]-4-piperidinecarboxylate;
- N-{4-(ethoxymethyl)-1-[2-(1-methyl-1H-pyrrol-2-yl)ethyl]-4-piperidinyl}-N-phenylpropanamide;
- ethyl {4-(methoxymethyl)-1-[2-(1-methyl-1H-pyrrol-2-yl)ethyl]-4-piperidinyl}phenylcarbamate; and
- methyl 4-[(ethoxycarbonyl)phenylamino]-1-[2-(1-methyl-1H-pyrrol-2-yl)ethyl]-4-piperidinecarboxylate.

We claim:

1. A chemical compound selected from the group consisting of a piperidine derivative having the formula:

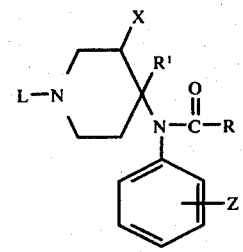

and the pharmaceutically acceptable acid addition salts and stereochemical optical isomeric forms thereof, wherein:

Z is a member selected from the group consisting of hydrogen, halo, lower alkyl, lower alkyloxy and trifluoromethyl;

L is a member selected from the group consisting of alkyl having from 3 to about 10 carbon atoms, cycloalkylmethyl wherein the cycloalkyl group has 3 to 6 carbon atoms, 2-arylethyl, 2-aryl-1-methylethyl, 2-aryl-2-hydroxyethyl, 2-aryl-2-hydroxy-1-methylethyl, 1-(arylcarbonyl)ethyl, 3-arylpropyl, 2-(arylamino)ethyl, 2-aryl-2-(lower alkylcarbonyloxy)ethyl, 2-aryl-2-(lower alkylcarbonyloxy)-1-methylethyl, 2-[aryl(lower alkylcarbonyl)amino]ethyl, 4-phenylcyclohexyl, 2,3-dihydro-1H-inden-2-yl, and lower alkenyl; said "aryl" being a member selected from the group consisting of phenyl, halophenyl, lower alkylphenyl, lower alkyloxyphenyl, (trifluoromethyl)phenyl, nitrophenyl, aminophenyl, naphthalenyl, pyridinyl, 2-furanyl, 2-thienyl, and 1-methyl-1H-pyrrol-2-yl;

X is a member selected from the group consisting of hydrogen and methyl;

R is a member selected from the group consisting of lower alkyl, lower alkyloxy and cycloalkyl having 3 to 6 carbon atoms; and $R^1$ is a member selected from the group consisting of
a. a carboxylate radical represented by the formula

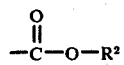

wherein $R^2$ is selected from the group consisting of lower alkyl, lower alkenyl and phenylmethyl;

b. an alkanoyl radical represented by the formula

wherein $R^3$ is lower alkyl; and c. an oxymethyl radical represented by the formula

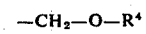

wherein $R^4$ is selected from the group consisting of hydrogen, lower alkyl, phenylmethyl and lower alkylcarbonyl;

provided that:

i. when said R² is phenylmethyl, or when said R⁴ is a member selected from the group consisting of phenylmethyl and lower alkylcarbonyl, then said L is selected from the group consisting of alkyl, cycloalkylmethyl wherein the cycloalkyl group has 3 to 6 carbon atoms, 2-arylethyl, 2-aryl-1-methylethyl, 1-(arylcarbonyl)-ethyl, 3-arylpropyl, 2-aryl-2-(lower alkylcarbonyloxy)-ethyl, 2-aryl-2-(lower alkylcarbonyloxy)-1-methylethyl, 4-phenylcyclohexyl, 2,3-dihydro-1H-inden-2-yl, and lower alkenyl; and ii. when said R⁴ is hydrogen then said L is other than 2-[aryl(lower alkylcarbonyl)amino]ethyl.

2. A compound selected from the group consisting of N- 4-(methoxymethyl)-1-[2-(2-thienyl)ethyl]-4-piperidinyl-N-phenylpropanamide and the pharmaceutically acceptable acid addition salts thereof.

3. A compound selected from the group consisting of methyl 4-[ (1-oxopropyl)phenylamino]-1-(2-phenylethyl)-4-piperidinecarboxylate and the pharmaceutically acceptable acid addition salts thereof.

4. A compound selected from the group consisting of methyl 4-[(1-oxopropyl)phenylamino]-1-[2-(2-thienyl)ethyl]-4-piperidinecarboxylate and the pharmaceutically acceptable acid addition salts thereof.

5. A compound selected from the group consisting of methyl 1-(1-methyl-2-phenylethyl)-4-[(1-oxopropyl)phenylamino]-4-piperidinecarboxylate and the pharmaceutically acceptable acid addition salts thereof.

6. A compound selected from the group consisting of methyl 3-methyl-4-[(1-oxopropyl)phenylamino]-1-(2-phenylethyl)-4-piperidinecarboxylate and the pharmaceutically acceptable acid addition salts thereof.

7. A compound selected from the group consisting of cis-methyl 3-methyl-4-[(1-oxopropyl)phenylamino]-1-(2-phenylethyl)-4-piperidinecarboxylate and the pharmaceutically acceptable acid addition salts thereof.

8. A compound selected from the group consisting of methyl 4-[(cyclopropylcarbonyl)phenylamino]-1-(2-phenylethyl)-4-piperidinecarboxylate and the pharmaceutically acceptable acid addition salts thereof.

9. a compound selected from the group consisting of N-[4-acetyl-1-(2-phenylethyl)-4-piperidinyl]-N-phenylpropanamide and the pharmaceutically acceptable acid addition salts thereof.

10. A compound selected from the group consisting of N-[4-acetyl-1-(2-phenylethyl)-4-piperidinyl]-N-phenylcyclopropanecarboxamide and the pharmaceutically acceptable acid addition salts thereof.

11. A compound selected from the group consisting of N-[4-(methoxymethyl)-1-(2-phenylethyl)-4-piperidinyl]-N-phenylpropanamide and the pharmaceutically acceptable acid addition salts thereof.

12. A compound selected from the group consisting of a piperidine derivative having the formula:

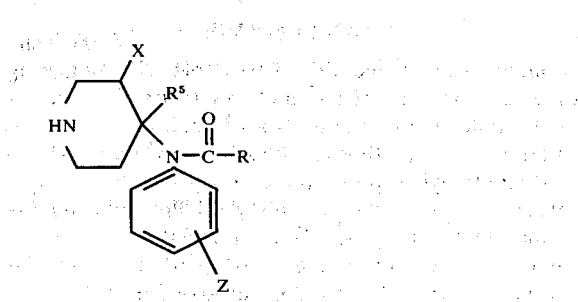

and the stereochemical optical isomeric forms thereof, wherein:

Z is a member selected from the group consisting of hydrogen, halo, lower alkyl, lower alkyloxy and trifluoromethyl;

X is a member selected from the group consisting of hydrogen and methyl;

R is a member selected from the group consisting of lower alkyl lower alkyloxy and cycloalkyl having 3 to 6 carbon atoms; and R⁵ is a member selected from the group consisting of a. a carboxylate radical represented by the formula:

wherein: R⁶ is a member selected from the group consisting of lower alkyl and lower alkenyl;

b. an alkanoyl radical represented by the formula:

wherein: R³ is lower alkyl; and c. an oxymethyl radical represented by the formula:

wherein: R⁷ is hydrogen or lower alkyl.

13. Methyl 4-[ (1-oxopropyl)phenylamino]-4-piperidinecarboxylate.

14. N-[4-(methoxymethyl)-4-piperidinyl]-N-phenylpropanamide.

15. Methyl 4-(phenylamino)-1-(2-phenylethyl)-4-piperidinecarboxylate.

16. Methyl 3-methyl-4-(phenylamino)-1-(2-phenylethyl)-4-piperidinecarboxylate.

17. Cis methyl 3-methyl-4-(phenylamino)-1-(2-phenylethyl)-4-piperidinecarboxylate.

* * * * *